US010570370B2

(12) United States Patent
Park et al.

(10) Patent No.: US 10,570,370 B2
(45) Date of Patent: Feb. 25, 2020

(54) METHOD FOR DIFFERENTIATION INTO RETINAL GANGLION CELLS FROM STEM CELLS

(71) Applicants: SEOUL NATIONAL UNIVERSITY R&DB FOUNDATION, Seoul (KR); SEOUL NATIONAL UNIVERSITY HOSPITAL, Seoul (KR)

(72) Inventors: Sung Sup Park, Seoul (KR); Ji Yeon Kim, Seoul (KR)

(73) Assignees: Seoul National University R&DB Foundation, Seoul (KR); Seoul National University Hospital, Seoul (KR)

( * ) Notice: Subject to any disclaimer, the term of this patent is extended or adjusted under 35 U.S.C. 154(b) by 0 days.

(21) Appl. No.: 15/506,736

(22) PCT Filed: Aug. 27, 2015

(86) PCT No.: PCT/KR2015/009004
§ 371 (c)(1),
(2) Date: Feb. 25, 2017

(87) PCT Pub. No.: WO2016/032263
PCT Pub. Date: Mar. 3, 2016

(65) Prior Publication Data
US 2018/0016552 A1    Jan. 18, 2018

(30) Foreign Application Priority Data
Aug. 27, 2014 (KR) ........................ 10-2014-0112638

(51) Int. Cl.
C12N 5/079 (2010.01)
A61K 35/30 (2015.01)
G01N 33/50 (2006.01)

(52) U.S. Cl.
CPC ............ *C12N 5/0621* (2013.01); *A61K 35/30* (2013.01); *G01N 33/5058* (2013.01); *C12N 2501/115* (2013.01); *C12N 2501/155* (2013.01); *C12N 2501/385* (2013.01); *C12N 2501/41* (2013.01); *C12N 2501/415* (2013.01); *C12N 2501/599* (2013.01); *C12N 2506/02* (2013.01); *C12N 2506/45* (2013.01)

(58) Field of Classification Search
CPC ............ C12N 5/0621; C12N 2501/115; C12N 2501/155; C12N 2501/385; C12N 2501/41; C12N 2501/415; C12N 2501/599; C12N 2506/02; C12N 2506/45; A61K 35/30; G01N 33/5058
USPC ....................................................... 424/93.7
See application file for complete search history.

(56) References Cited

U.S. PATENT DOCUMENTS 7,541,186 B2    6/2009  Reh et al.
2011/0223140 A1*  9/2011  Park ..................... C12N 5/0621
424/93.7

FOREIGN PATENT DOCUMENTS

KR    10-1268741 B1    4/2011
WO    2011043591 A2    4/2011
WO    2011043592 A2    4/2011

OTHER PUBLICATIONS

Chen et al., "Generation of retinal ganglion-like cells from reprogrammed mouse fibroblasts" IOVS Nov. 2010, vol. 51, No. 11, p. 5970-5978.
Japanese Office Action for 2017-531436 dated Feb. 27, 2018.
Loubradou-Bourges, Supplementary European Search Report for EP 15836684, dated Feb. 15, 2018.
Jagatha et al., "In vitro differentiation of retinal ganglion-like cells from embryonic stem cell derived neural progenitors" Biochemical and Biophysical Research Communications, 2009, vol. 380, p. 230-235.
Tucker et al., "Use of a synthetic xeno-free culture substrate for induced pluripotent stem cell induction and retinal differentiation" Stem Cells Translational Medicine, 2013, vol. 2, p. 16-24.
Gill et al., "Methods of retinal ganglion cell differentiation from pluripotent stem cells" Transnational Vision Science and Technology, 2014, vol. 3, No. 4, p. 1-13.
Barres, Barbara, A., et al., "Immunological, Morphological, and Electrophysiological Variation among Retinal Ganglion Cells Purified by Panning", Neron, vol. 1, (Nov. 1988), pp. 791-803.
Bull, Natalie, D., et al., "Use of Adult Rat Retinal Explant Model for Screening of Potential Retinal Ganglion Cell Neuroprotective Therapies", Investigative Opthalmology & Visual Science, vol. 52, No. 6, (May 2011), pp. 3309-3320.
Connors, B.W., et al., "Electrophysiological Properties of Neocortical Neurons in Vitro", Journal of Neurophysiology, vol. 48, No. 6, (Dec. 1982), pp. 1302-1320.
Jagatha, B., et al., "In vitro differentiation of retinal ganglion-like cells from embryonic stem cell derived neural progenitors", Biochem Biophys Res Commun, vol. 380, No. 2, Mar. 6, 2009, pp. 230-235.
McCormick, David, A., et al., "Post-Natal Development of Electrophysiological Properties of Rat Cerebral Cortical Pyramidal Neurones", J. Physiol., vol. 393, (1987), pp. 743-762.
Osakada, Fumitaka, et al., "Stepwise differentiation of pluripotent stem cells into retinal cells", Nature Protocols, vol. 4, No. 6, (2009), pp. 811-824.

(Continued)

*Primary Examiner* — Jennifer M. H. Tichy
(74) *Attorney, Agent, or Firm* — Greer, Burns, and Crain, Ltd.; Gregory P. Einhorn

(57) ABSTRACT

Provided are a method of preparing retinal ganglion cells by differentiation of stem into retinal ganglion cells, retinal ganglion cells differentiated by the method, a method of screening for a death inhibitor or a proliferation promoter of retinal ganglion cells using the retinal ganglion cells differentiated by the method, a kit of screening for the death inhibitor or the proliferation promoter of retinal ganglion cells including the retinal ganglion cells differentiated by the method, a pharmaceutical composition for treating glaucoma or optic neuropathy including the retinal ganglion cells, a method of treating glaucoma or optic neuropathy including the step of administering the retinal ganglion cells to a subject suspected of having glaucoma or optic neuropathy, and a method of preparing a mature retinal ganglion cell line.

33 Claims, 25 Drawing Sheets

(56) References Cited

OTHER PUBLICATIONS

Parameswaran, Sowmya, et al., "Induced Pluripotent Stem Cells Generate Both Retinal Ganglion Cells and Photoreceptors: Therapeutic Implications in Degenerative Changes in Glaucoma and Age-Related Macular Degeneration", Stem Cells, vol. 28, No. 4, (Apr. 2010), pp. 695-703.

Zuber, Michael, E., et al., "Specification of the vertebrate eye by a network of eye field transcription factors", Development, vol. 130, No. 21, (Nov. 2003), pp. 5155-5167.

* cited by examiner

FIG. 1B  FIG. 1D  FIG. 1F
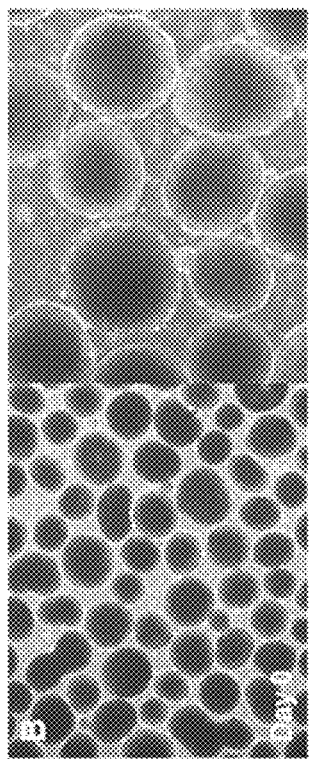 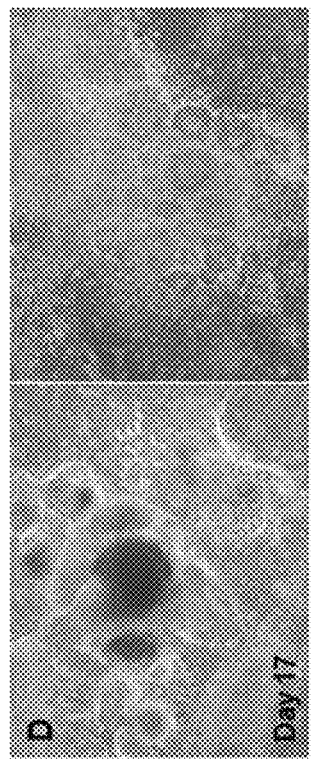 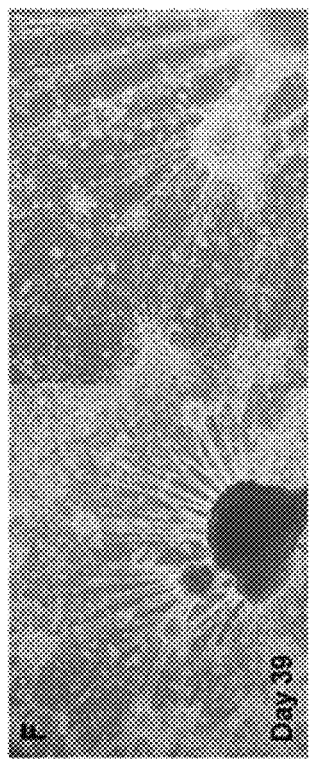
 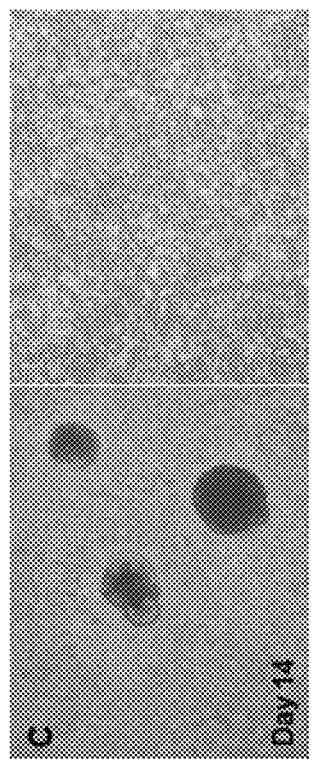 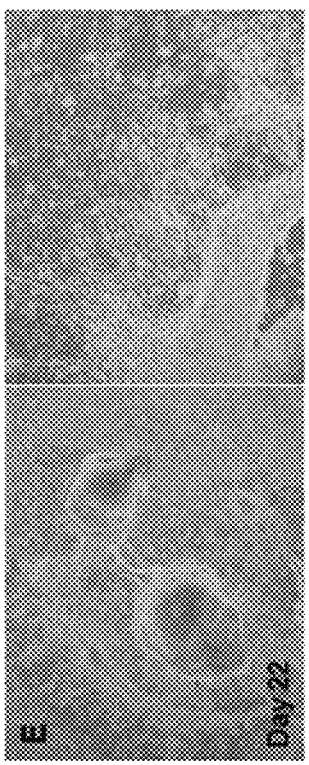
FIG. 1A  FIG. 1C  FIG. 1E

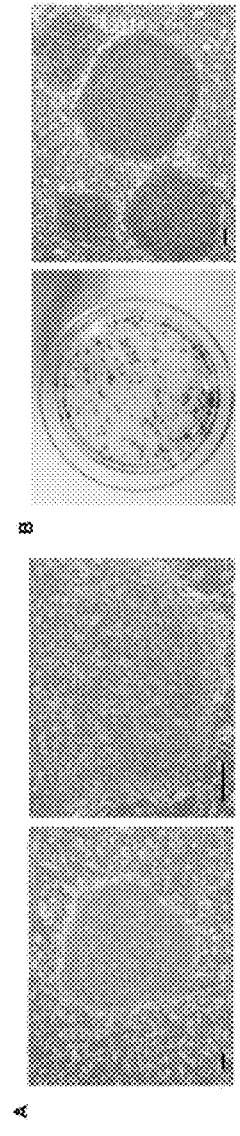
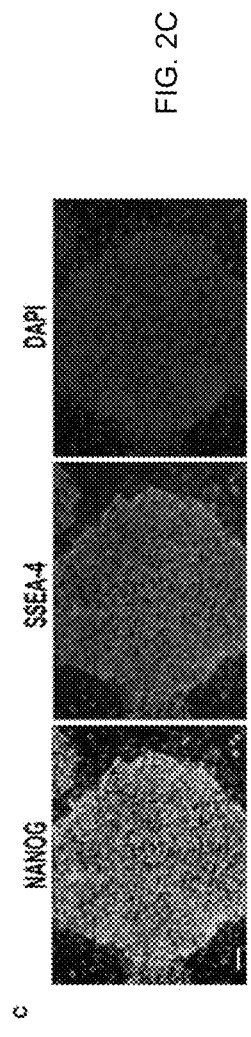
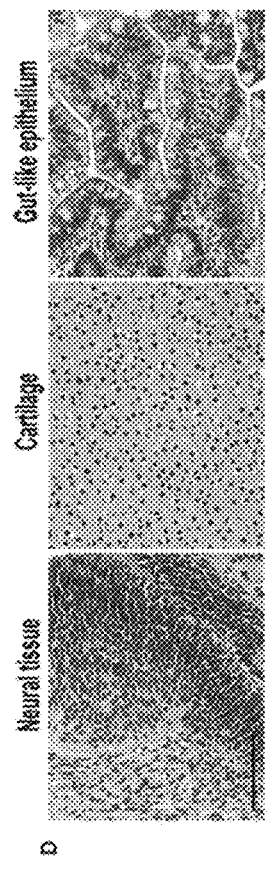
FIG. 2A
FIG. 2B
FIG. 2C
FIG. 2D

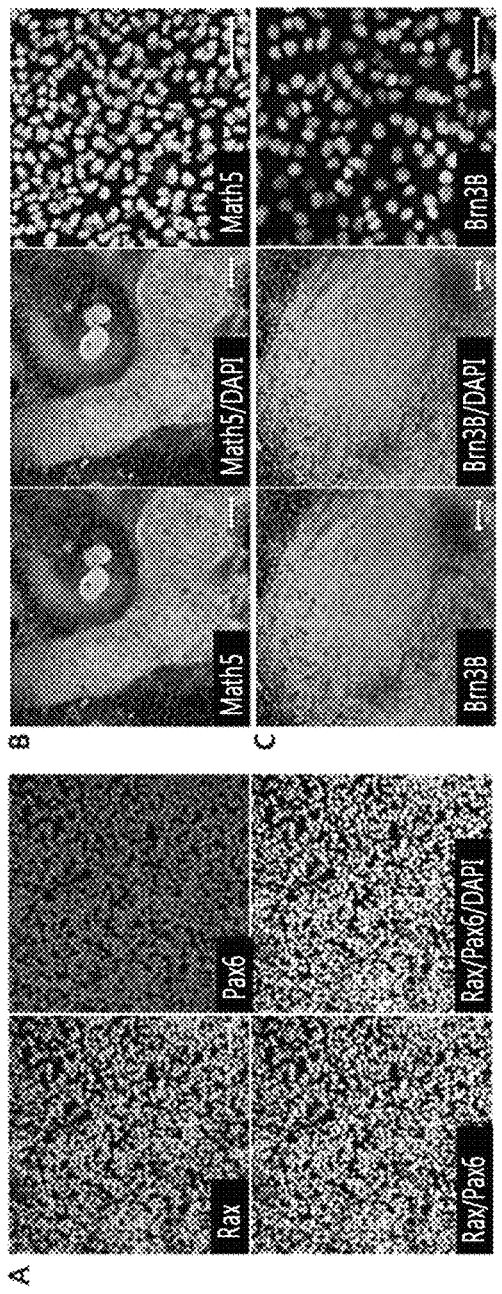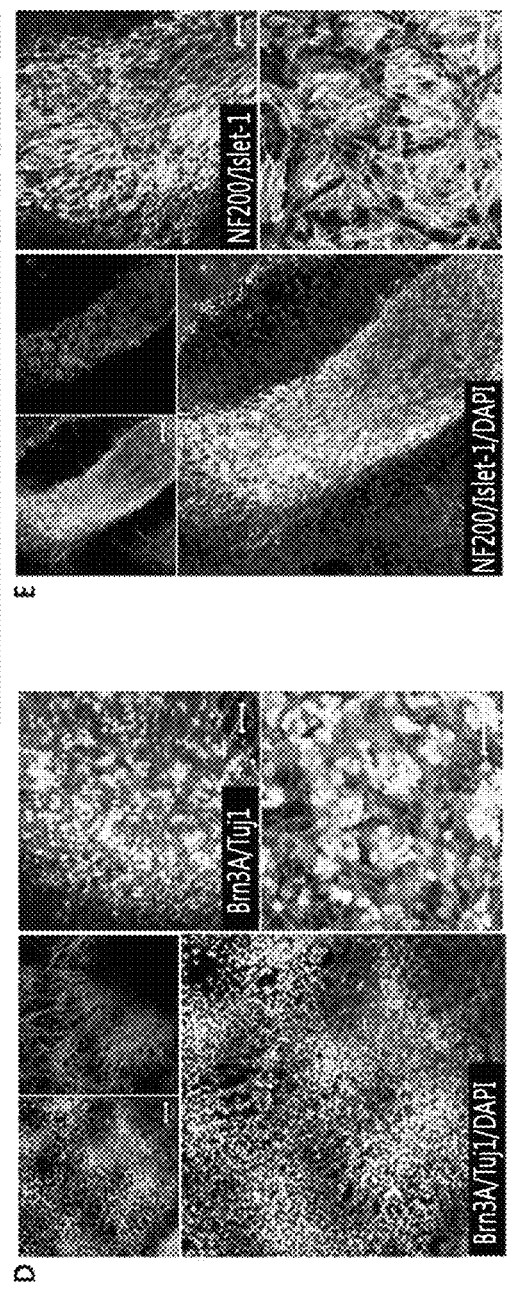
FIG. 7A  FIG. 7B  FIG. 7C  FIG. 7D  FIG. 7E

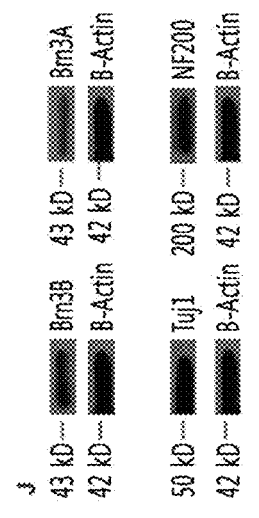
FIG. 9A
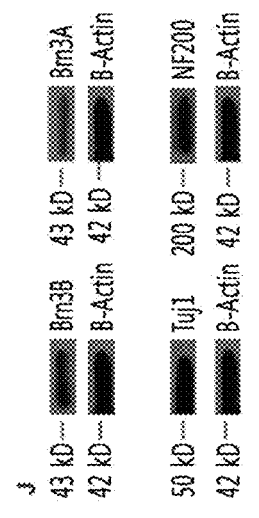
FIG. 9B
FIG. 9C
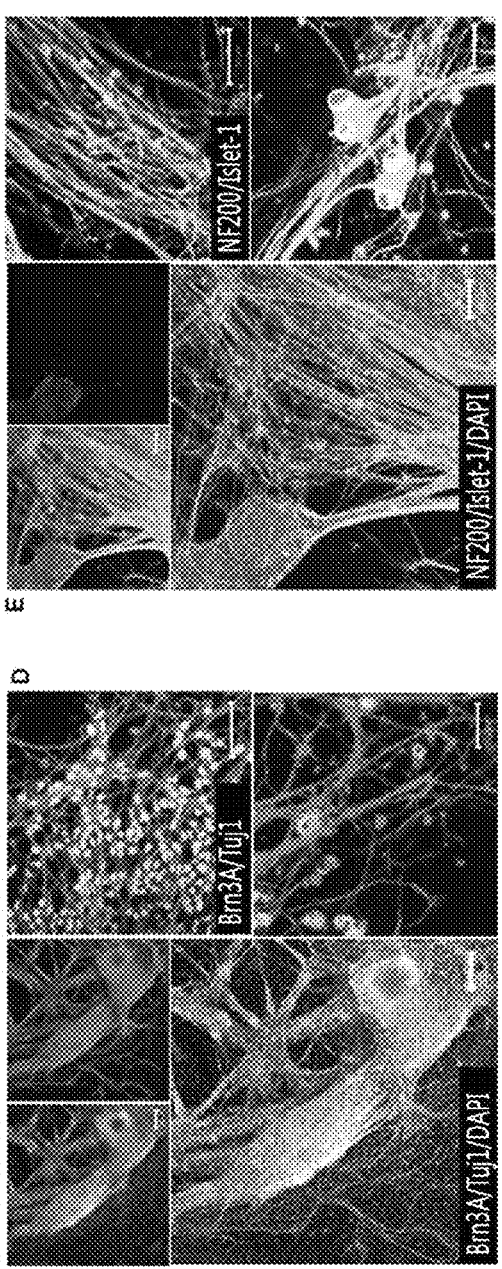
FIG. 9D
FIG. 9E
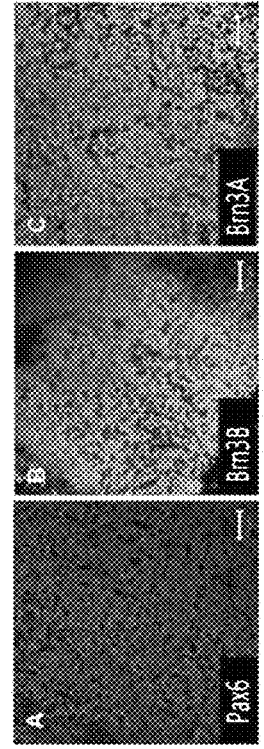
FIG. 9F
FIG. 9G
FIG. 9H
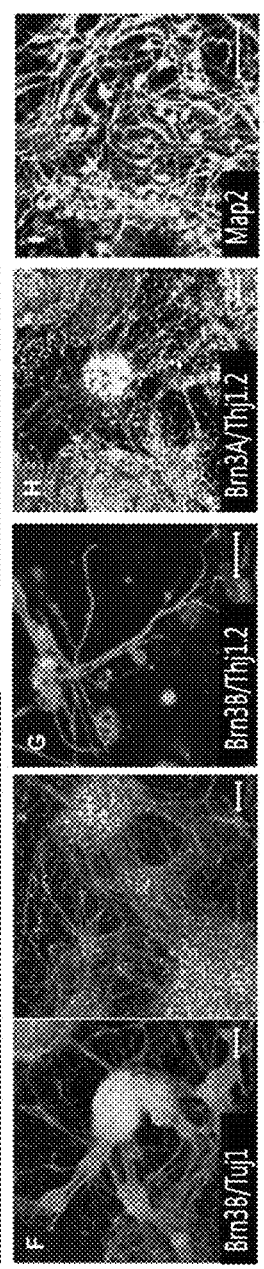
FIG. 9I
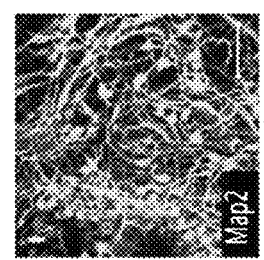
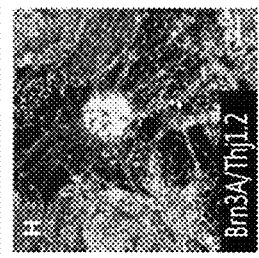
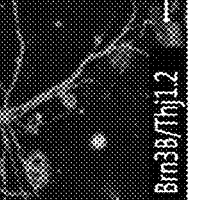
FIG. 9J

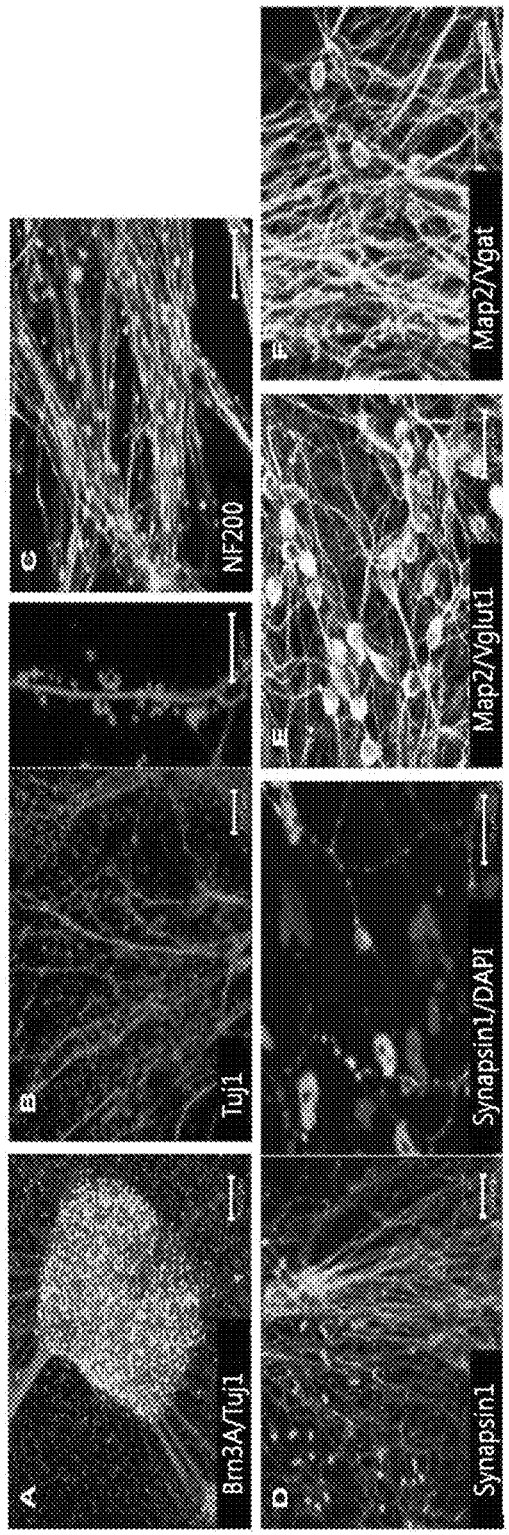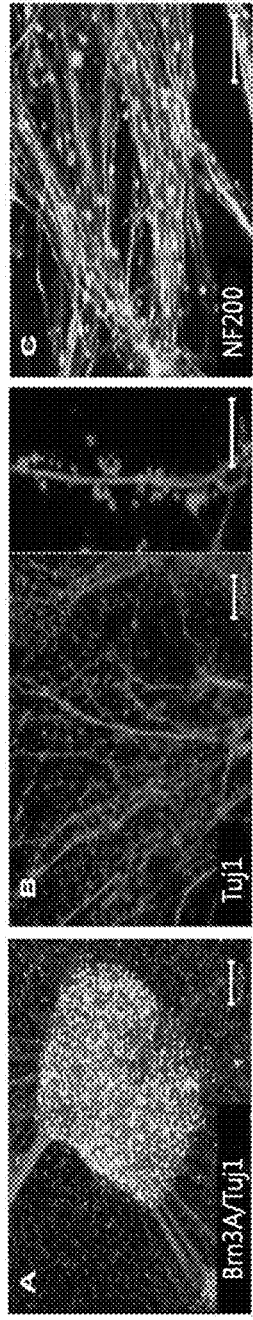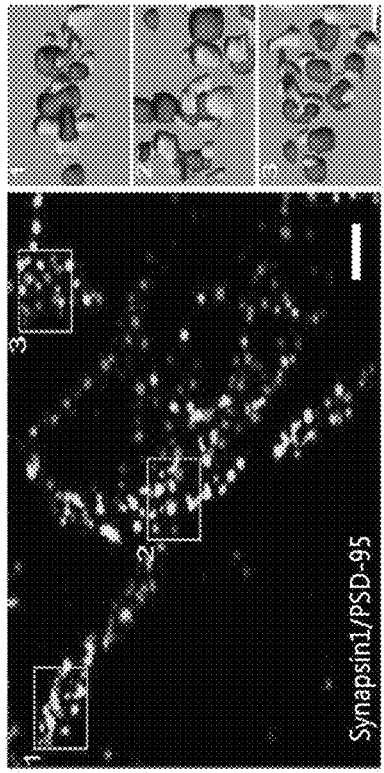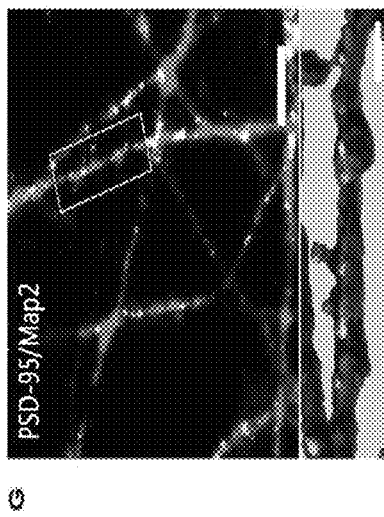

FIG. 11A
FIG. 11B
FIG. 11C
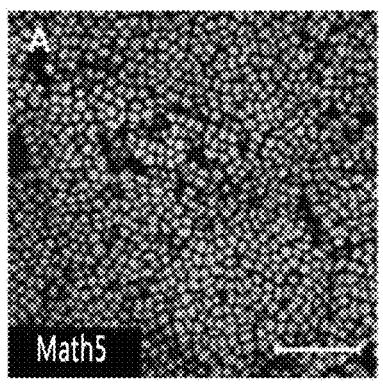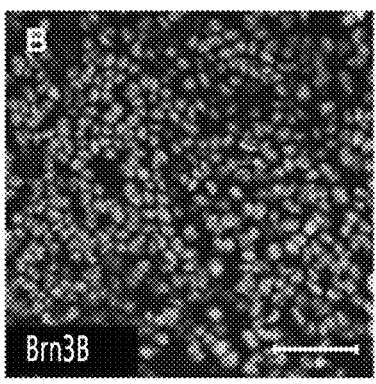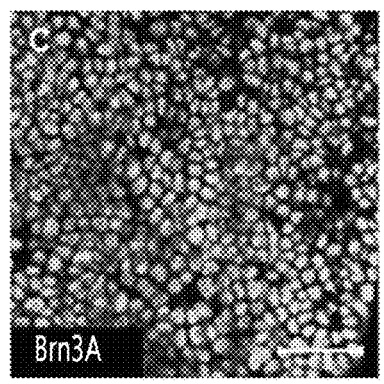
FIG. 11D
FIG. 11E
FIG. 11F
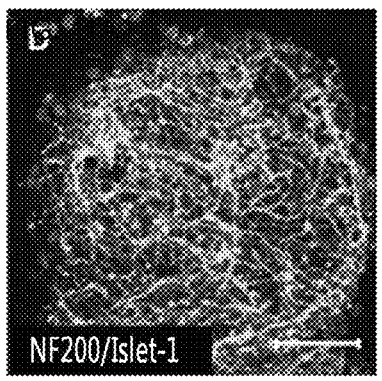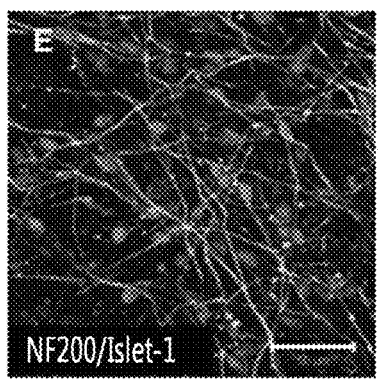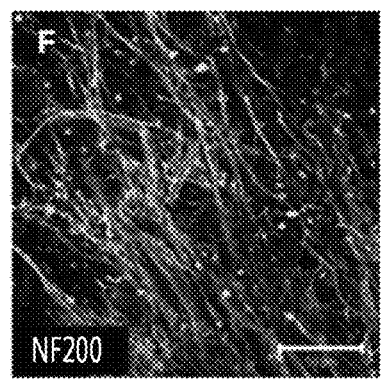
FIG. 11G
FIG. 11H
FIG. 11I
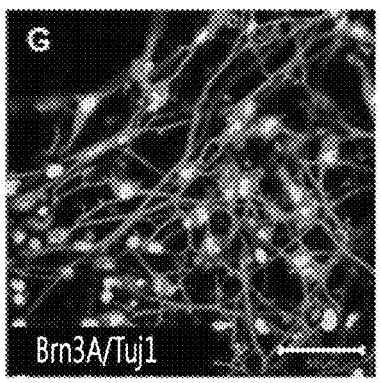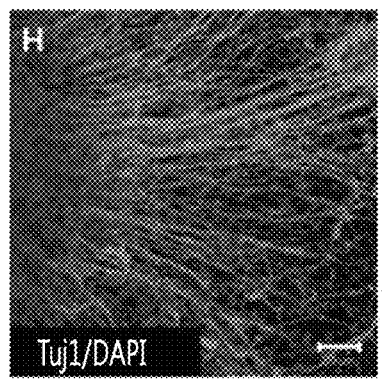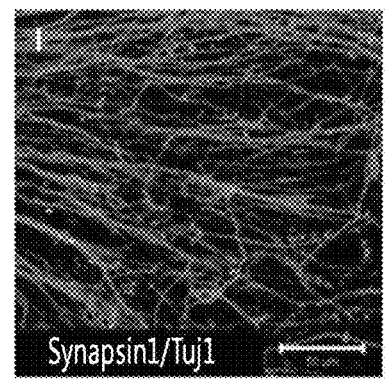

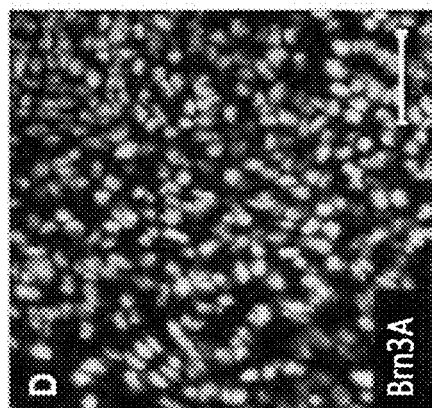
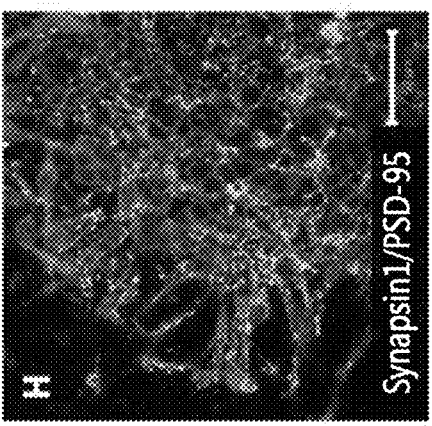
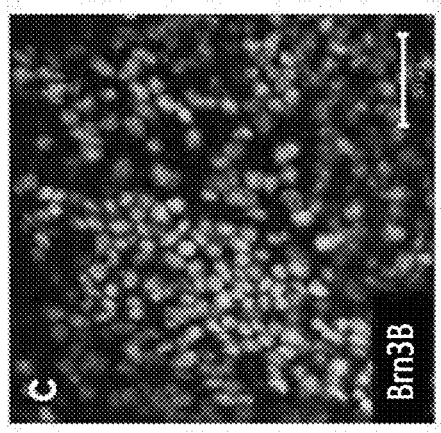
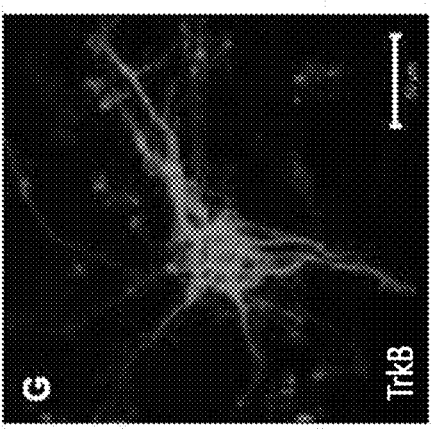
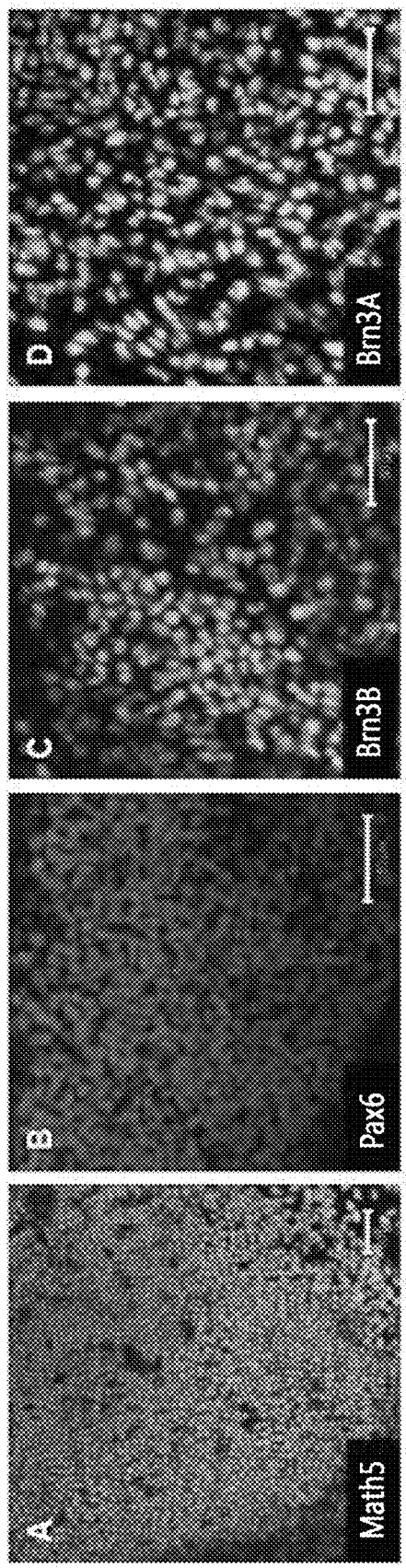
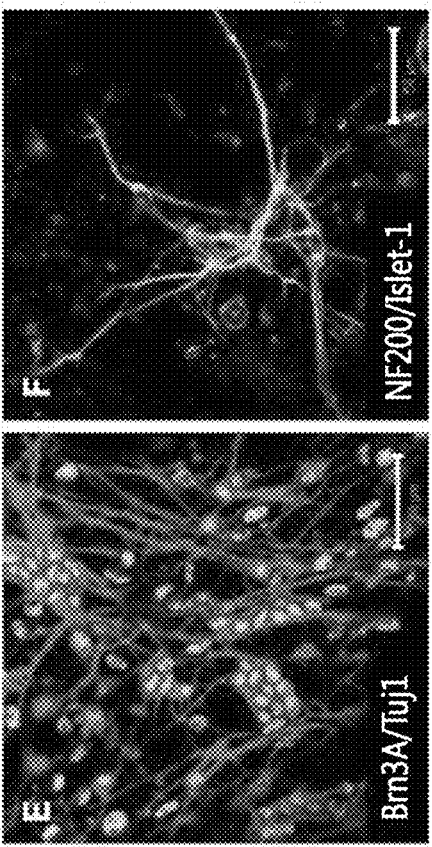

FIG. 13A  FIG. 13B  FIG. 13C
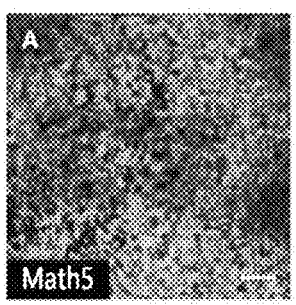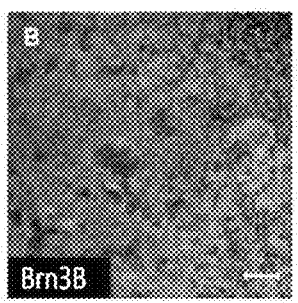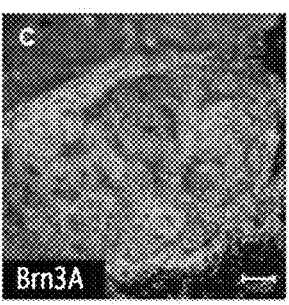
FIG. 13D
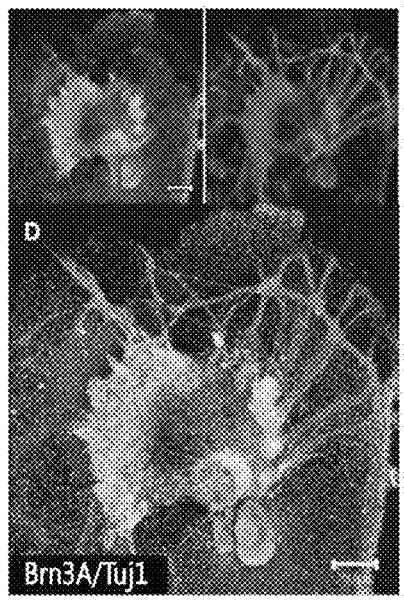
FIG. 13E  FIG. 13F
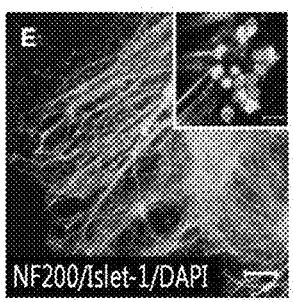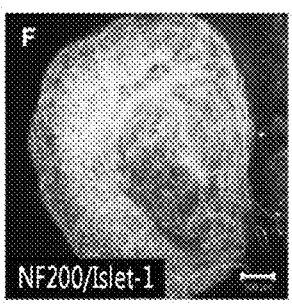
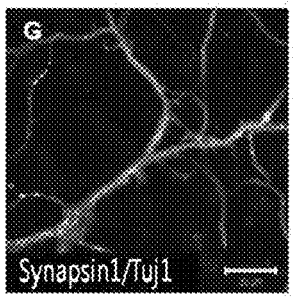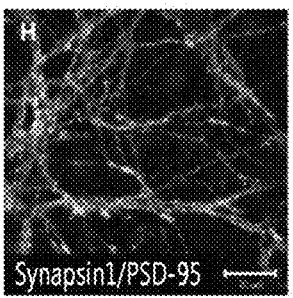
FIG. 13G  FIG. 13H

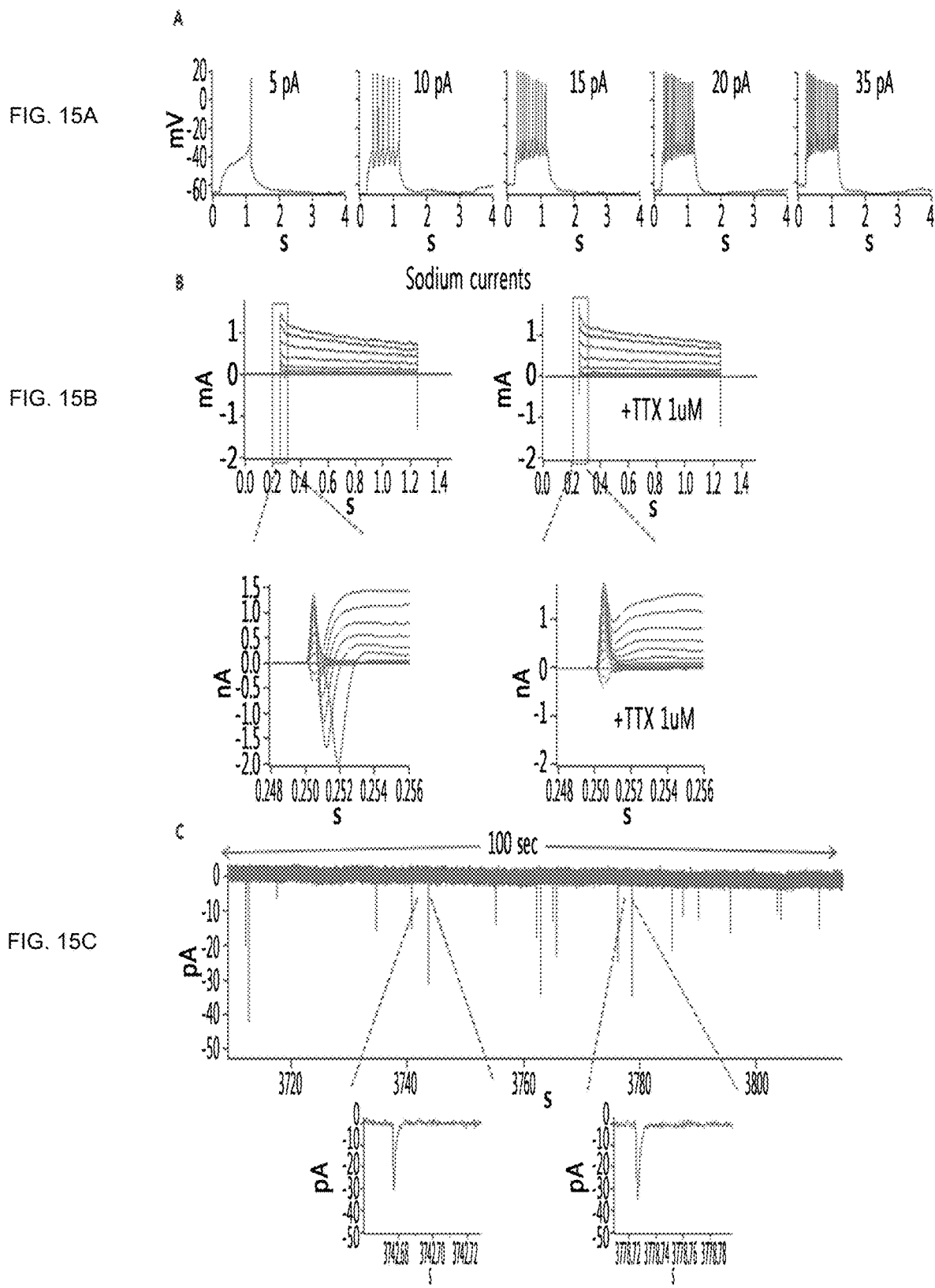

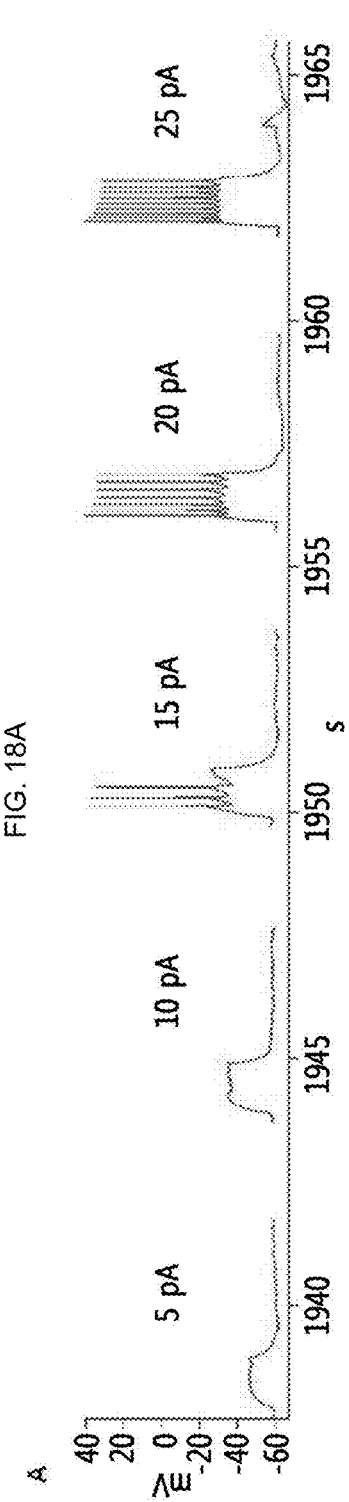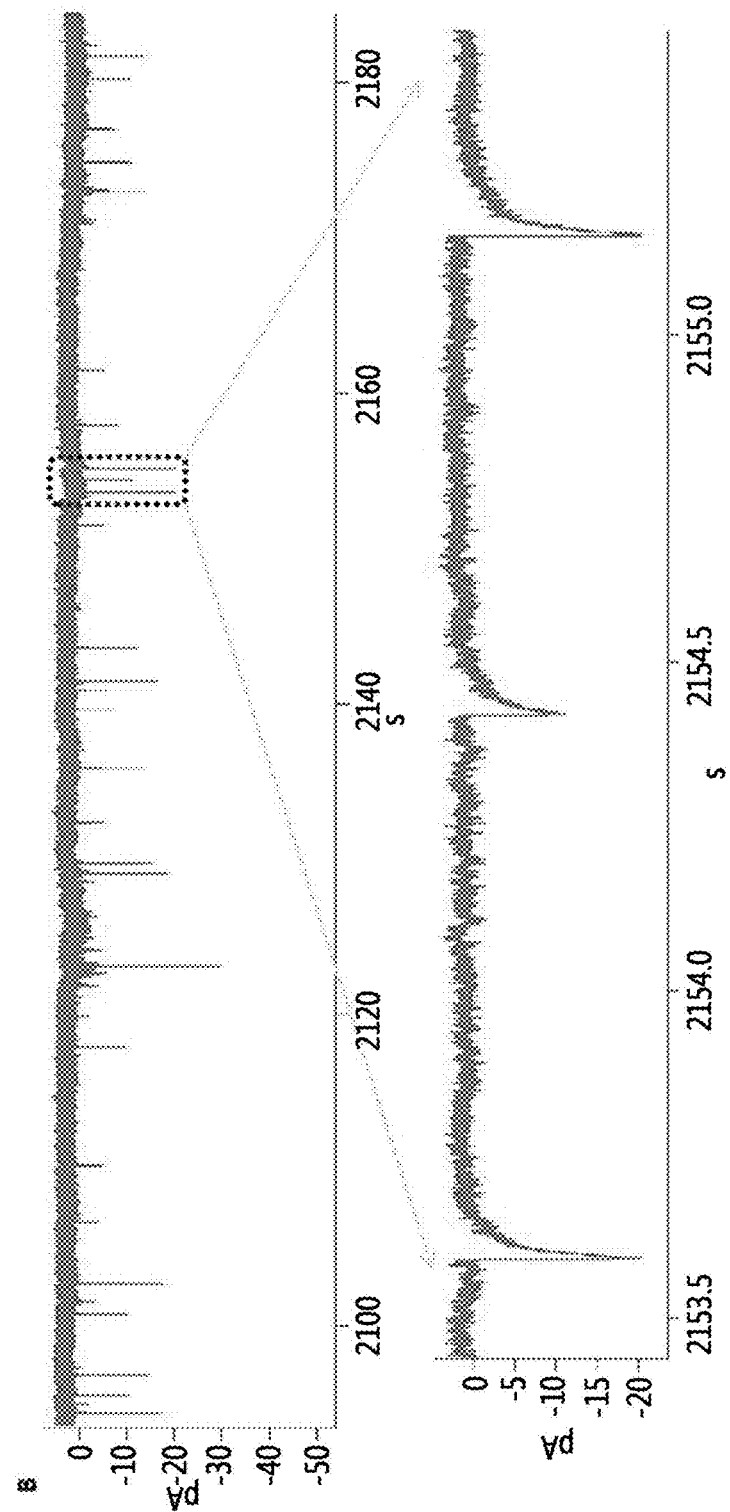
FIG. 18A
FIG. 18B

FIG. 22

| Factor/Figure | A | B | C | D | E |
|---|---|---|---|---|---|
| Wnt3a | Dkk1+ | - | + | + | + |
| Shh | + | + | - | + | - |
| RA | + | + | - | - | + |

FIG. 24A
FIG. 24B
FIG. 24C
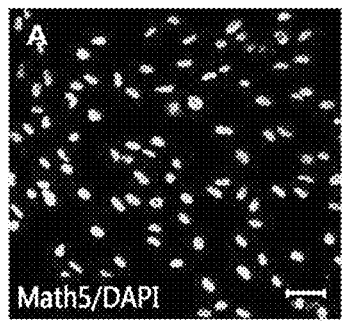
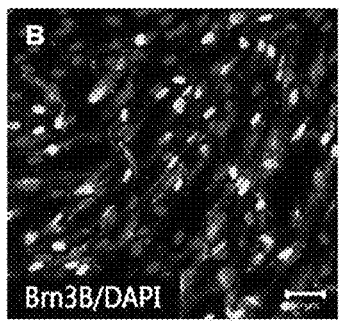
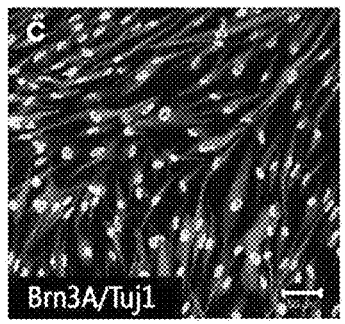
FIG. 24D
FIG. 24E
FIG. 24F
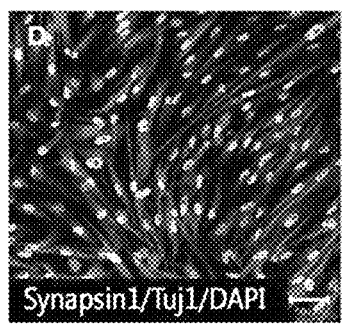
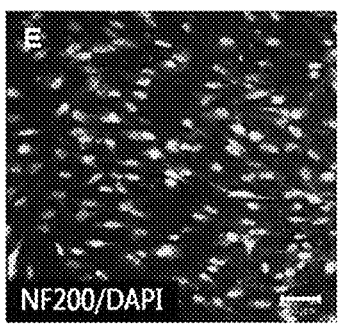
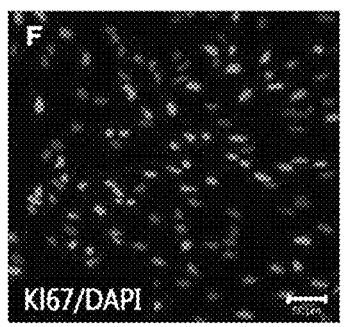
FIG. 24G
FIG. 24H
FIG. 24I
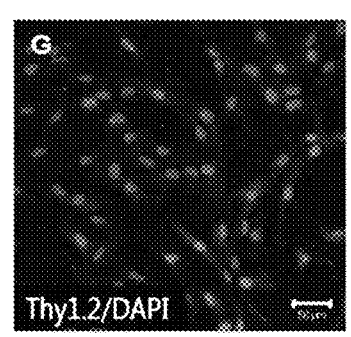
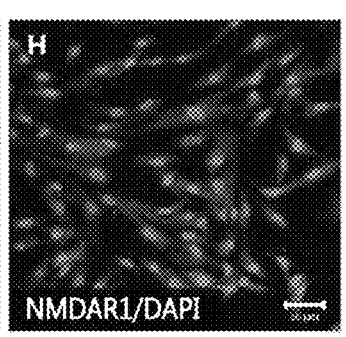
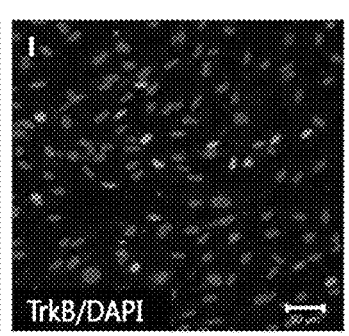

METHOD FOR DIFFERENTIATION INTO RETINAL GANGLION CELLS FROM STEM CELLS

RELATED APPLICATIONS

This application is a national phase application claiming benefit of priority under 35 U.S.C. § 371 to International (PCT) Patent Application serial number PCT/KR2015/009004, filed Aug. 27, 2015, which claims benefit of priority to Korean Application 10-2014-0112638, filed Aug. 27, 2014. The aforementioned applications are expressly incorporated herein by reference in their entirety and for all purposes.

TECHNICAL FIELD

The present invention relates to a method of preparing retinal ganglion cells by differentiation of stem cells into retinal ganglion cells, retinal ganglion cells differentiated by the method, a method of screening for a death inhibitor or a proliferation promoter of retinal ganglion cells using the retinal ganglion cells differentiated by the method, a kit of screening for the death inhibitor or the proliferation promoter of retinal ganglion cells including the retinal ganglion cells differentiated by the method, a pharmaceutical composition for treating glaucoma or optic neuropathy including the retinal ganglion cells, a method of treating glaucoma or optic neuropathy including the step of administering the retinal ganglion cells to a subject suspected of having glaucoma or optic neuropathy, and a method of preparing a mature retinal ganglion cell line.

BACKGROUND

Blindness is the medical condition of lacking visual perception. As many as tens of millions of people, which account for 0.2% to 0.5% of the population of the world, are affected by blindness, and suffer from great losses in personal, social and economical respects. Retinal glaucoma or optic neuropathy is one of the leading causes of blindness worldwide. Glaucoma is the most common progressive optic neuropathy, leading to irreversible blindness. The global prevalence of glaucoma for people over 40 is as high as about 2% to 3%. Globally, there were an estimated 60 million people with glaucoma in 2010. The prevalence of glaucoma is expected to increase to 80 million by 2020 (Quigley H A and Broman A T, Br J Ophthalmol 2006; 90: 262-267). The prevalence of glaucoma in the socially active middle-aged generation is 2% to 3%, and it is expected that the number of patients will greatly increase as the population ages, which will become a social and economic burden. Currently, reduction of intraocular pressure is the only method that is clinically applied for glaucoma treatment, but it is known that a significant proportion of glaucoma patients still progress to blindness. It is known that reduction of intraocular pressure is a conservative method capable of merely inhibiting glaucoma progression, and treatment of the underlying glaucoma is impossible.

Meanwhile, optic neuropathy generally describes optic nerve abnormalities caused by different factors, and includes optic neuritis, ischemic optic neuropathy, toxic or deficiency optic neuropathy, hereditary optic neuropathy, optic atrophy, etc. Among them, the diseases caused by optic nerve degeneration and damage can be helped by stem cell therapy.

Specifically, glaucoma is caused by degeneration and loss of retinal ganglion cells (RGCs). After passing through the eye, light is converted to electric signals in photoreceptor cells, and retinal ganglion cells transmit these electric signals to the central optic nerve of the brain.

On the other hand, stem cell/regenerative therapy may be the best therapy for glaucoma and optic neuropathy. A disease caused by degeneration and loss of a single cell type is a strong target of stem cell therapy. In particular, because the eye is very easily accessible for surgical manipulation, and various surgical procedures have been established, there are no difficulties in the application of stem cells to lesions, and the eye can be a model for the development of therapeutic drugs.

The goals of stem cell therapy in glaucoma and optic neuropathy are 1) to replace degenerative and damaged RGCs with new RGCs (cell replacement therapy, neuro-regeneration), 2) to induce therapeutic effects of anti-inflammation, anti-cell death, neuroprotection, and vascular protection on degenerative and damaged RGCs as paracrine effects of stem cell therapy, and 3) to select and develop new drugs using stem cells for the treatment of glaucoma, for which direct therapeutic agents have not yet been developed. This therapy may lead to a personalized stem cell therapy using patient-derived pluripotent stem cells. Highly efficient production of retinal ganglion cells is essential in the development of therapeutic compositions or models for therapeutic drugs. In particular, there is a problem in that retinal ganglion cells degenerated or damaged by diseases cannot be prepared in vitro, and therefore, it is impossible to develop new drugs for glaucoma and optic neuropathy using normal or abnormal retinal ganglion cells. Therefore, if a large amount of retinal ganglion cells are produced from stem cells, it is possible to create disease models for retinal ganglion cell-associated diseases such as glaucoma and optic neuropathy, and therefore, drugs for the diseases can be easily developed. Especially, production of RGCs differentiated from patient-derived induced pluripotent stem cells (iPSC-RGCs) makes it possible to develop new drugs capable of preventing and inhibiting optic nerve degeneration. In addition, the present inventors disclosed a method of differentiating retinal cells from stem cells in the previous patents (Korean Patent NO. 10-1268741 (2013 May 22) and WO2011/043591 (2011 Apr. 14)). However, according to the methods disclosed in the above documents, only about 6% of retinal progenitor cells are differentiated into retinal ganglion cells. Accordingly, there is still a need to develop a differentiation method capable of maximizing differentiation into retinal ganglion cells.

DISCLOSURE

Technical Problem

The present inventors have tried to produce retinal ganglion cells which are differentiated from human embryonic stem cells, but they showed poor differentiation. Accordingly, the present inventors have made many efforts to develop a new method capable of producing retinal ganglion cells from stem cells. As a result, they developed a method of differentiating human embryonic stem cells into retinal ganglion cells with a high yield for a short period of time of 5 weeks under chemically defined culture conditions without gene implantation or co-culture with retinal tissues. They found that the retinal ganglion cells developed according to the method of the present invention are about 200-fold higher in population than the starting human embryonic stem cells, and the retinal ganglion cells exhibit excellent neurophysiological functions, thereby completing the present invention.

Technical Solution

An object of the present invention is to provide a method of preparing mature retinal ganglion cells by differentiation of stem cells into mature retinal ganglion cells, comprising (a) culturing retinal progenitor cells in a medium containing an IGF1R (insulin-like growth factor-1 receptor) activator and a Wnt signaling pathway activator to differentiate them into immature retinal ganglion cells; and (b) culturing the immature retinal ganglion cells in a medium prepared by removing the Wnt signaling pathway activator from the medium of step (a) and adding the IGF1R activator thereto.

Another object of the present invention is to provide a method of preparing mature retinal ganglion cells by differentiation of immature retinal ganglion cells into mature retinal ganglion cells, including the step of culturing immature retinal ganglion cells in a medium containing an IGF1R activator and an Shh (sonic hedgehog) signaling pathway activator.

Still another object of the present invention is to provide a method of screening for a death inhibitor or a proliferation promoter of mature retinal ganglion cells, comprising (a) treating the mature retinal ganglion cells obtained and isolated by the above method with a death inhibitor candidate or a proliferation promoter candidate; and (b) determining that the candidate is a death inhibitor or a proliferation promoter of mature retinal ganglion cells when the candidate inhibits death of the mature retinal ganglion cells or promotes proliferation of the mature retinal ganglion cells, compared to a non-candidate-treated group.

Still another object of the present invention is to provide immature retinal ganglion cells and mature retinal ganglion cells prepared according to the above-described method of the present invention.

Still another object of the present invention is to provide a kit of screening for a death inhibitor or a proliferation promoter of mature retinal ganglion cells, including the mature retinal ganglion cells.

Still another object of the present invention is to provide a pharmaceutical composition for treating glaucoma or optic neuropathy, including the mature retinal ganglion cells.

Still another object of the present invention is to provide a method of treating glaucoma or optic neuropathy including the step of administering the mature retinal ganglion cells to a subject suspected of having glaucoma or optic neuropathy.

Still another object of the present invention is to provide a method of preparing a mature retinal ganglion cell line, comprising (a) culturing retinal progenitor cells in a medium containing an IGF1R activator and a Wnt signaling pathway activator to differentiate them into immature retinal ganglion cells; and (b) culturing the immature retinal ganglion cells in a medium prepared by removing the Wnt signaling pathway activator from the medium of step (a) and adding the IGF1R activator thereto.

Advantageous Effects

According to the method of the present invention, retinal ganglion cells can be differentiated from stem cells with a high yield, and the retinal ganglion cells obtained by the method can be used in a selection test of therapeutic agents for diseases such as glaucoma or optic neuropathy and also used in cell therapy.

DESCRIPTION OF DRAWINGS

FIG. 1A-1B shows cytomorphological microphotographs.

FIG. 1A shows cell floc of human embryonic stem cells in an undifferentiated state (30 passages): after being cultured for 5 days from cells of passage number 29. The cells are typical cell floc of human embryonic stem cells in an undifferentiated state, characterized by definite separation from adjacent mouse embryonic fibroblast feeder cells and having a plain surface and uniform morphology.

FIG. 1B shows floating aggregates, in which the floating aggregates were cultured for 4 days in ultra-low attachment plates after being isolated from the undifferentiated human embryonic stem cell floc of FIG. 1(A). The floating aggregates have spherical morphology, and one floating aggregate consists of about 292±53 cells.

FIG. 1C-1F shows cytomorphological microphotographs of cells differentiating into retinal ganglion cells.

FIG. 1C shows cells on day 14 after induction of the differentiation: Cell morphology after transferring the floating aggregates to poly-D-lysine/laminin-coated plates and culturing them for 10 days therein, that is, on day 14 after induction of the differentiation of the undifferentiated human embryonic stem cells. It was observed that the cells were separated from the floating aggregates and underwent differentiation, and had a morphological character of the early stage of differentiation, with meager cytoplasm and round, large nuclei.

FIG. 1D shows cells on day 17 after induction of the differentiation: Cell morphology on day 17 after induction of the differentiation of the undifferentiated human embryonic stem cells. The cells differentiated with concomitant active proliferation, and cell flocs under active proliferation and differentiation formed a round flower-shaped rosette configuration.

FIG. 1E shows cells on day 22 after induction of the differentiation: The cells became richer in cytoplasm and their nuclei were smaller than those of FIG. 1(D) as the differentiation progressed. It was observed that cell flocs differentiated into neurons with short or long neuronal axons.

FIG. 1F shows cells on day 39 after induction of the differentiation: Most cells differentiated into neurons. With the progress of differentiation into neurons, the cells showed the same cellularity, but had a mature neuronal shape, compared to those on day 22 after induction of the differentiation in FIG. 1(E). The nerve cell bodies formed a plurality of clusters, which were connected with each other by long neuronal axons.

*Microscopic field: FIG. 1A-1F (left: 40× magnification; right: 100× magnification).

FIG. 2A-D shows characteristics of induced pluripotent stem cells reprogrammed from human neonatal foreskin BJ-1 fibroblasts.

FIG. 2A shows phase-contrast microscopic images of human induced pluripotent stem cells: Cell line after being cultured for 6 days from cells of passage number 6. The stem cells are characterized by definite separation from adjacent mouse embryonic body cells as feeder cells and having a plain surface and uniform morphology.

FIGS. 2B and 2C are alkaline phosphatase, Nanog, and SSEA-4 staining results showing the characteristics of human embryonic stem cells of induced pluripotent stem cells.

FIG. 2D is the result of teratoma assay for evaluating pluripotency of induced pluripotent stem cells generated from fibroblasts. At 10 weeks after transplantation of induced pluripotent stem cells generated from fibroblasts into the dorsal surface of immunosuppressed SCID mouse, induced pluripotent stem cells developed teratomas with three germ layers of ectoderm (left: neural tissues), mesoderm (middle: cartilage), and endoderm (right: digestive system), indicating pluripotency.

*Scale bar: FIG. 2A-2C: 200 μm.

FIG. 7A-7E shows the results of examining cell marker expressions on day 17 after induction of the differentiation of a human embryonic stem cell line H9 according to Protocol A.

FIG. 7A shows cells positive to both of the retinal progenitor cell markers, Rax and Pax6, are observed. Retinal progenitor cells have the characteristic of being positive to both the markers.

FIG. 7B shows Math5, a marker for immature retinal ganglion cells, is observed. Compared to the whole cell (DAPI-stained), almost 100% cells are Math5-positive.

FIG. 7C shows Brn3B, a retinal ganglion cell-specific marker, is observed in almost all cells. It is indicated that fate of the cells to retinal ganglion cells is determined by Math5, and then they begin to differentiate into retinal ganglion cells.

FIG. 7D shows all cells are positive to both of Brn3A (green staining: nuclear staining) which is one of the retinal ganglion cell-specific markers, and Tuj1 (red staining: also called β-tubulin III) which is specific to the cytoplasm of the neuronal cell.

FIG. 7E shows about 20% of the cells are positive to both of Islet-1 (red: nuclear staining), which is a marker of the subtype of retinal ganglion cells, and NF200 (green), which is a neural axon-specific marker.

*Scale bar: FIG. 7A: 50 μm; FIG. 7B: 200 μm & 50 μm; FIG. 7C to FIG. 7E: 100 μm & 50 μm.

Nuclear staining of the whole cell: DAPI (blue staining).

Figure 8:
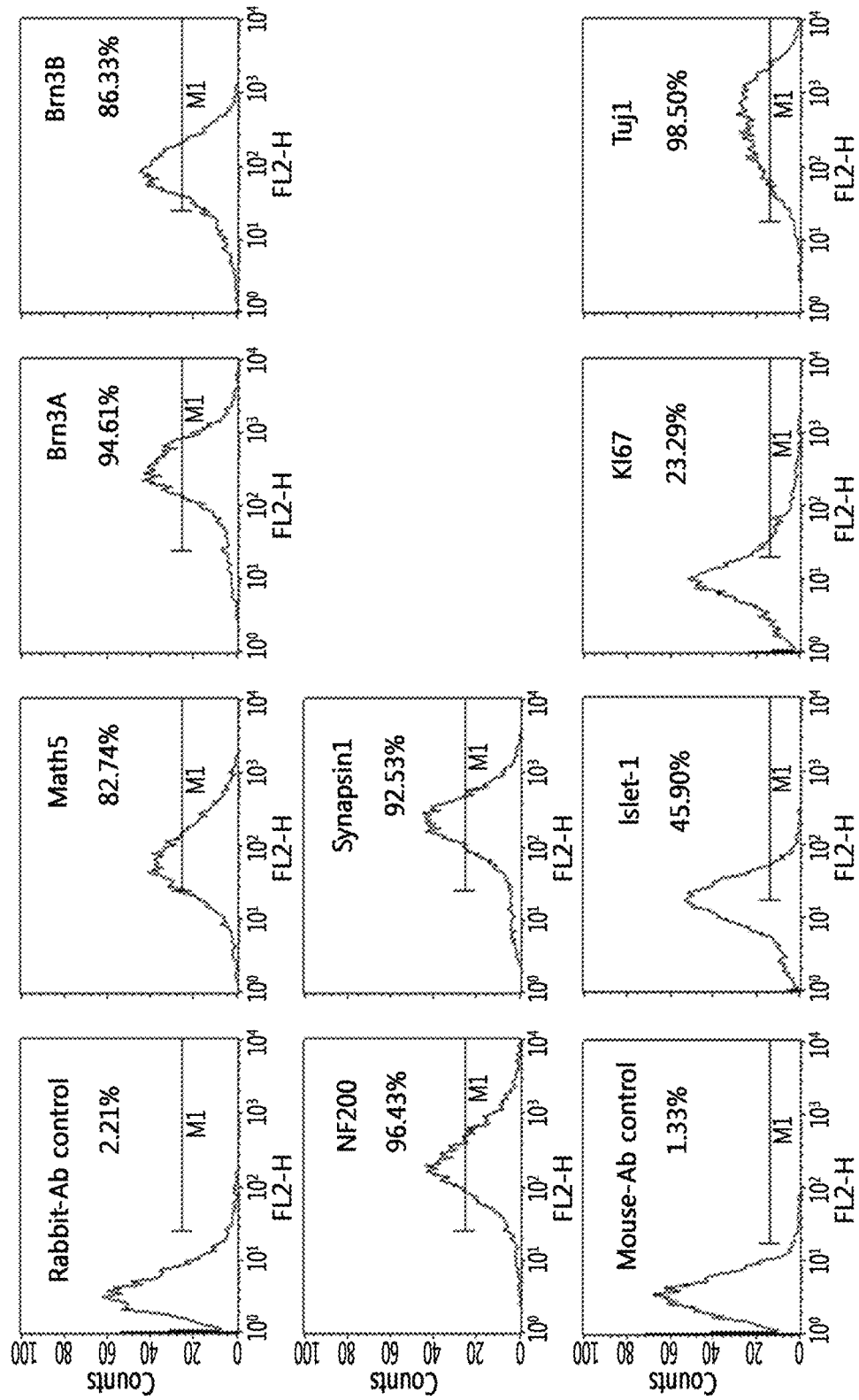

FIG. 8 shows the results of flow cytometry to examine marker expressions on day 39 after induction of the differentiation of a human embryonic stem cell line H9 according to Protocol A (experimental results).

FIG. 9A-FIG. 9J shows the results of examining cell marker expressions on day 39 after induction of the differentiation of a human embryonic stem cell line H9 according to Protocol A.

FIG. 9A-9C shows the retinal ganglion cell-specific markers, FIG. 9A Pax6, FIG. 9B Brn3B, and FIG. 9C Brn3A observed in FIG. 7A-7E are still observed.

FIG. 9D shows almost all cells are positive to both of Brn3A (green: nucleus) and Tuj1 (red: cytoplasmic staining, both axons and dendrites are stained). The number and thickness of neuronal axons and dendrites are increased, compared to the cells on day 17 of FIG. 7A-7E. Axonal spiny process and ring, synaptic interaction between cells, and dendritic arbor and spiny process are observed.

FIG. 9E shows cells positive to both of Islet-1 (red: nucleus) and NF200 (green: axon) are observed. The number of axons is increased and a mature form is observed, compared to the cells on day 17 of FIG. 7A-FIG. 7E.

FIG. 9F shows Brn3B (green) and Tuj1 (red): The majority of cell flocs are positive to both Brn3B and Tuj1, which is retinal ganglion cell-specific staining.

FIG. 9G shows Brn3B (green) and Thy1.2 (red): Nuclear staining for Brn3B and cytoplasmic staining for Thy1.2 are observed, which are characteristics of retinal ganglion cells.

FIG. 9H shows Brn3A (green) and Thy1.2 (red): Nuclear staining for Brn3B and cytoplasmic staining for Thy1.2 are observed, which are characteristics of retinal ganglion cells.

FIG. 9I shows Map2 (green): Staining of cytoplasm including dendrites is observed.

FIG. 9J shows results of Western blotting, obtained by reacting antibodies with the lysate of human embryonic stem cell-derived retinal ganglion cells on day 39 after induction of differentiation, indicating retinal ganglion cell-specific proteins.

*Scale bar: FIG. 9A to FIG. 9C: 50 μm; FIG. 9D: 200 μm, 50 μm & 20 μm; FIG. 9E: 100 μm, 50 μm & 20 μm; FIG. 9F: 200 μm & 100 μm; FIG. 9G: 20 μm; FIG. 9H: 100 μm; FIG. 9I: 50 μm.

Nuclear staining of the whole cell: DAPI (blue).

FIG. 10A-10H shows the results of examining cell marker expressions on day 59 after induction of the differentiation of a human embryonic stem cell line H9 according to Protocol A.

FIG. 10A shows cells positive to both of Brn3A (green: nucleus) and Tuj1 (red: cytoplasmic staining, both axons and dendrites are stained) are observed. The number and thickness of axons and dendrites are increased, compared to the cells on day 39 of FIG. 8.

FIG. 10B shows Tuj1: Axonal spiny process and ring, synaptic interaction between cells, and dendritic arbor and spiny process are observed.

FIG. 10C shows NF200: Dendritic spiny process and axon rings are observed.

FIG. 10D shows Synapsin1: Synapsin1, which is a representative protein involved in neurotransmitter release, is observed in the form of functionally mature puncta along dendrites in presynaptic vesicles, indicating that synapse interaction with other neurons occurs to transmit neural electric stimuli between cells.

FIG. 10E shows Map2/Vglut1: The majority of presynaptic vesicles indicated by Synapsin1 of FIG. 10D is glutamatergic vesicles (Vglut1: red). Presence of Vglut1 along Map2-positive dendrites (green) is observed. Glutamatergic excitatory neurons are produced.

FIG. 10F shows Map2/Vgat: The minority of presynaptic vesicles indicated by Synapsin1 of FIG. 10D is GABAergic vesicles (Vgat: red). Presence of Vgat along Map2-positive dendrites (green) is observed.

FIG. 10 G shows PSD-95/Map2: Protein formation is observed in postsynaptic vesicles, and an excitatory synaptic marker PSD-95 is distributed along dendrites (Map2).

FIG. 10H shows Synapsin1/PSD-95: physical synapses by super resolution microscopy: Synapses between presynaptic Synapsin1 and postsynaptic excitatory PSD-95 are observed. The physical synapses can be identified by juxtaposition of presynaptic and postsynaptic vesicle complexes. There are neurotransmitters causing spontaneous excitatory postsynaptic currents (sEPSCs), which are the electrophysiological characteristic of "mature retinal ganglion cells", indicating functional maturation of retinal ganglion cells.

*Scale bar: FIG. 10A: 100 μm; FIG. 10B: 100 μm & 20 μm; FIG. 10C: 20 μm; FIG. 10D: 50 μm & 20 μm; FIG. 10E: 20 μm; FIG. 10F: 20 μm; FIG. 10G: 50 μm & 1 μm; FIG. 10H: 2 μm & 0.5 μm.

Nuclear staining of cells: DAPI (blue).

FIG. 11A-11I shows the results of examining cell marker expressions on day 39 after induction of the differentiation of a human embryonic stem cell line H9 according to Protocol B.

FIG. 11A shows Math5
FIG. 11B shows Brn3B
FIG. 11C shows Brn3A
FIG. 11D shows, FIG. 11E shows Islet-1 (red: nucleus) and NF200 (green: axon)
FIG. 11F shows NF200
FIG. 11G shows Brn3A, Tuj1
FIG. 11H shows Tuj1
FIG. 11I shows Synapsin1/Tuj1

*Scale bar: FIG. 11A to FIG. 11I: 50 μm. Nuclear staining of FIG. 11H: DAPI (blue).

FIG. 12A-12H shows the results of examining cell marker expressions on day 39 after induction of the differentiation of a human embryonic stem cell line H9 according to Protocol C.

FIG. 12A shows Math5
FIG. 12B shows Pax6
FIG. 12C shows Brn3B
FIG. 12D shows Brn3A
FIG. 12E shows Brn3A, Tuj1
FIG. 12E shows Islet-1 (red: nucleus) and NF200 (green: axon)
FIG. 12G shows TrkB: Expression of TrkB, which is a neurotrophin receptor marker of mature retinal ganglion cells is observed.
FIG. 12H shows Synapsin1/PSD-95

*Scale bar: FIG. 12A to FIG. 12H: 50 μm.

FIG. 13A-FIG. H shows the results of examining cell marker expressions on day 39 after induction of the differentiation of a human embryonic stem cell line H7 according to Protocol A.

FIG. 13A shows Math5
FIG. 13B shows Brn3B
FIG. 13C shows Brn3A

Characteristic markers of retinal ganglion cells are observed in almost all cells.

FIG. 13D shows Brn3A (green: nucleus) and Tuj1 (red: cytoplasmic staining, both axons and dendrites are stained).

FIG. 13E and FIG. 13F show Islet-1 (red: nucleus) and NF200 (green: axon)

FIG. 13G shows Synapsin1 (green), Tuj1 (red): A presynaptic marker Synapsin1 is distributed along Tuj1-positive axons.

FIG. 13H shows Synapsin1/PSD-95: The presynaptic marker Synapsin1 and postsynaptic marker PSD-95 are close to each other, indicating differentiation of H7 cell line into "mature retinal ganglion cells" having mature electrophysiological functions by Protocol A, like H9 cell line.

*Scale bar: FIG. 13A: 50 μm; FIG. 13B and FIG. 13C: 100 μm; FIG. 13D: 200 μm; FIG. 13E: 200 μm & 20 μm; FIG. 13F: 100 μm; FIG. 13G: 20 μm; FIG. 13H: 20 μm.

Nuclear staining of FIG. 13E: DAPI (blue).

FIG. 14A-FIG. 14L shows the results of examining cell marker expressions on day 39 after induction of the differentiation of human induced pluripotent stem cells according to Protocol A.

Figure 14A:
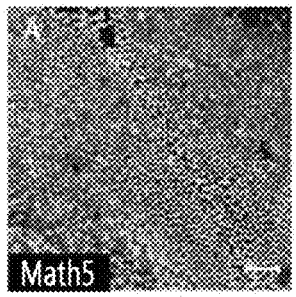
Figure 14B:
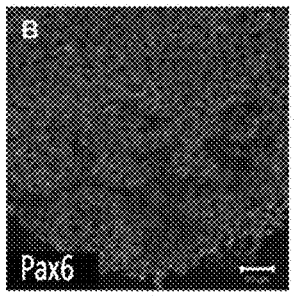
Figure 14C:
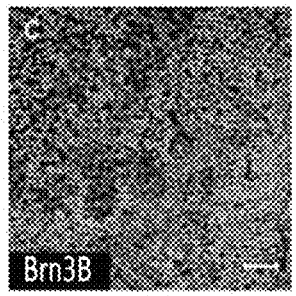
Figure 14D:
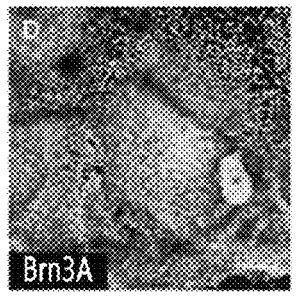
Figure 14E:
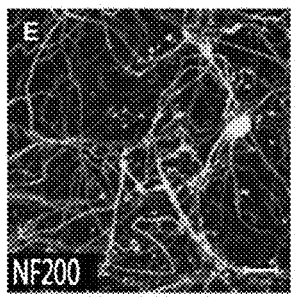
Figure 14F:
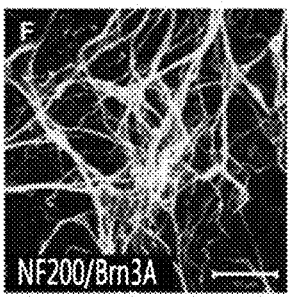
Figure 14G:
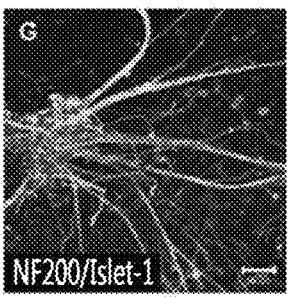
Figure 14H:
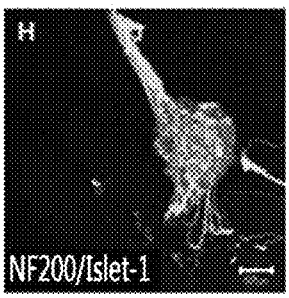
Figure 14I:
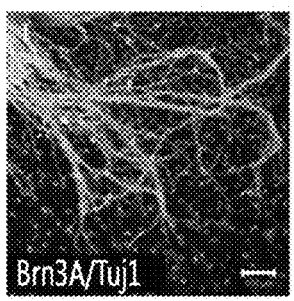
Figure 14J:
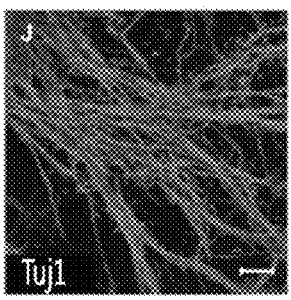
Figure 14K:
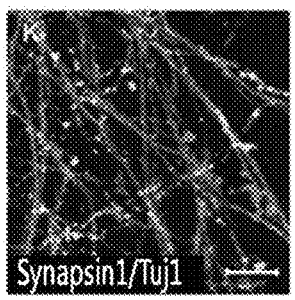
Figure 14L:
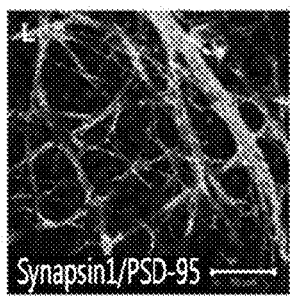

FIG. 14A shows Math5
FIG. 14B shows Pax6
FIG. 14C shows Brn3B
FIG. 14D shows Brn3A
FIG. 14E shows NF200
FIG. 14F shows Brn3A (red: nucleus) and NF200 (green: axon)
FIG. 14G shows Islet-1 (red: nucleus) and NF200 (green: axon): One of the subtypes of retinal ganglion cells is observed.
FIG. 14H shows NF200, Islet-1
FIG. 14I shows Brn3A, Tuj1
FIG. 14I shows Tuj1: Differentiation of axons of mature neurons is observed.
FIG. 14K shows Synapsin1 (green), Tuj1 (red): A presynaptic marker Synapsin1 is distributed along Tuj1-positive axons.
FIG. 14L shows Synapsin1/PSD-95: The presynaptic marker Synapsin1 and postsynaptic marker PSD-95 are close to each other, indicating differentiation of human induced pluripotent stem cell line into "mature retinal ganglion cells" having mature electrophysiological functions by Protocol A, like H9 cell line.

*Scale bar: FIG. 14A to FIG. 14C, FIG. 14E to FIG. 14H, FIG. 14J, FIG. 14L: 50 μm; FIG. 14D, FIG. 14I: 100 μm; FIG. 14K: 20 μm.

FIG. 15A-FIG. 15C shows the results of electrophysiological analysis on day 39 after induction of the differentiation of human embryonic stem cell line H9 according to Protocol A.

FIG. 15A shows a robust regular-spiking train of action potentials is observed in response to step current injection (pA) in human embryonic stem cell-derived retinal ganglion cells, indicating that the produced retinal ganglion cells acquired mature electrophysiological characteristics. In general, as neurons mature, action potentials change from a single short spiking to multiple lasting spikings in response to current injection.

FIG. 15B shows voltage-gated sodium channel of human embryonic stem cell-derived retinal ganglion cells: Current responses to step depolarizations from a holding potential of −80 mV to +40 mV are superimposed. Fast-activating and inactivating inward sodium currents were completely blocked by applying tetrodotoxin (TTX).

FIG. 15C shows spontaneous excitatory postsynaptic currents (sEPSCs) were detected in human embryonic stem cell-derived retinal ganglion cells without co-culture with other retinal tissues on day 39 after induction of the differentiation, indicating that functional excitatory synapses are formed between human embryonic stem cell-derived retinal ganglion cells.

FIG. 16A-FIG. 16E shows the results of electrophysiological analysis on day 59 after induction of the differentiation of human embryonic stem cell line H9 according to Protocol A.

Figures 16A, 16B, 16C, 16D, 16E:
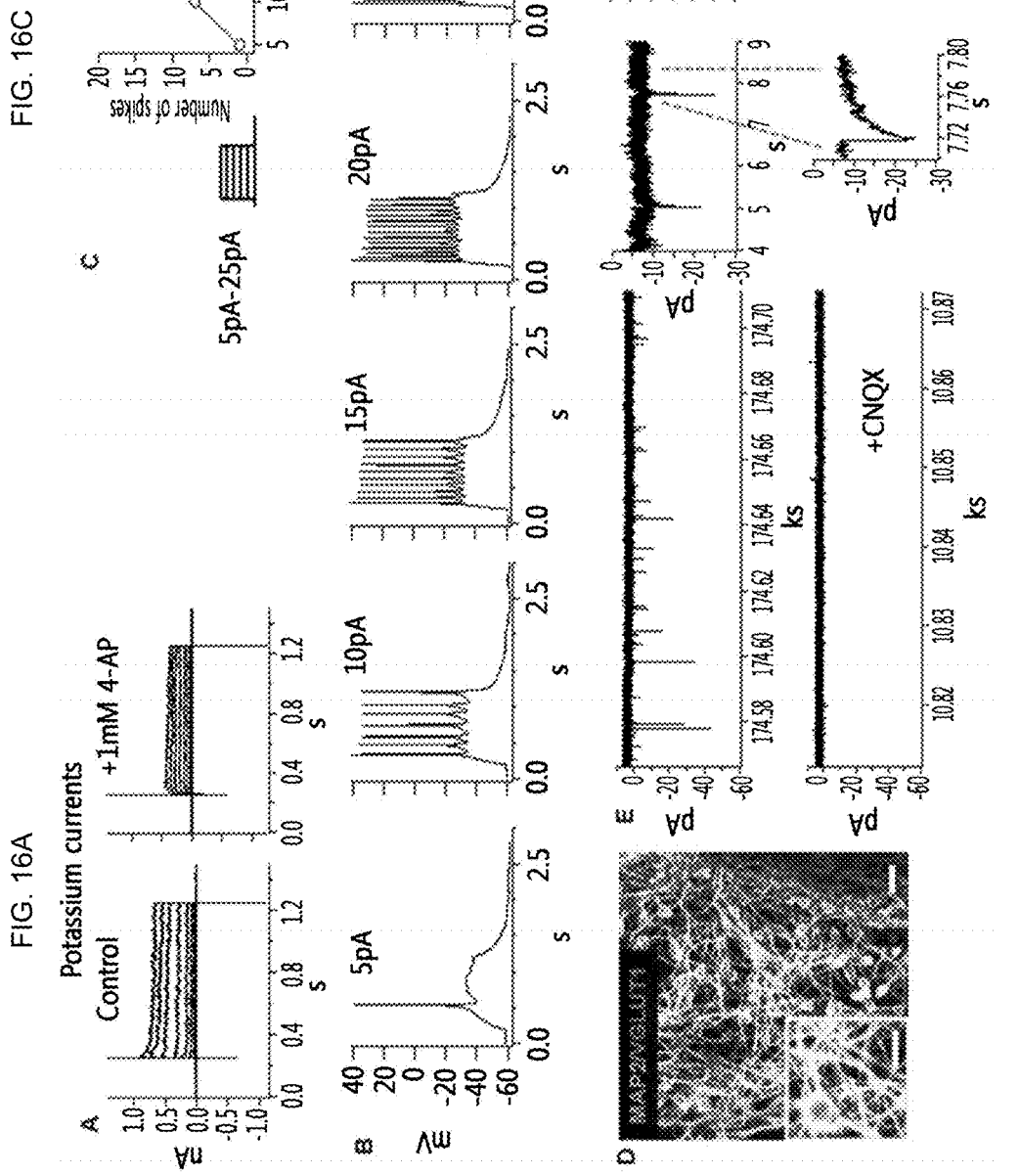

FIG. 16A shows Potassium current: 4-Aminopyridine (4-AP) blocked a fast-activating fraction of outward potassium current.

FIG. 16B shows a robust regular-spiking train of action potentials is observed in response to step current injection (pA) in human embryonic stem cell-derived retinal ganglion cells. The number of spike was increased, compared to those on day 39 after induction of the differentiation.

FIG. 16C shows a graph for the number of spikes evoked by step current injections (pA): The number of spikes increases in proportion to strength of the current injected.

FIG. 16D shows a staining image of glutamatergic presynaptic vesicles (Vglut1) distributed in dendrites (Map2-positive).

FIG. 16E shows spontaneous excitatory postsynaptic current (sEPSCs): An AMPA receptor antagonist CNQX blocked the appearance of sEPSCs. Glutamatergic excitatory synapses are formed.

Figures 17A, 17B:
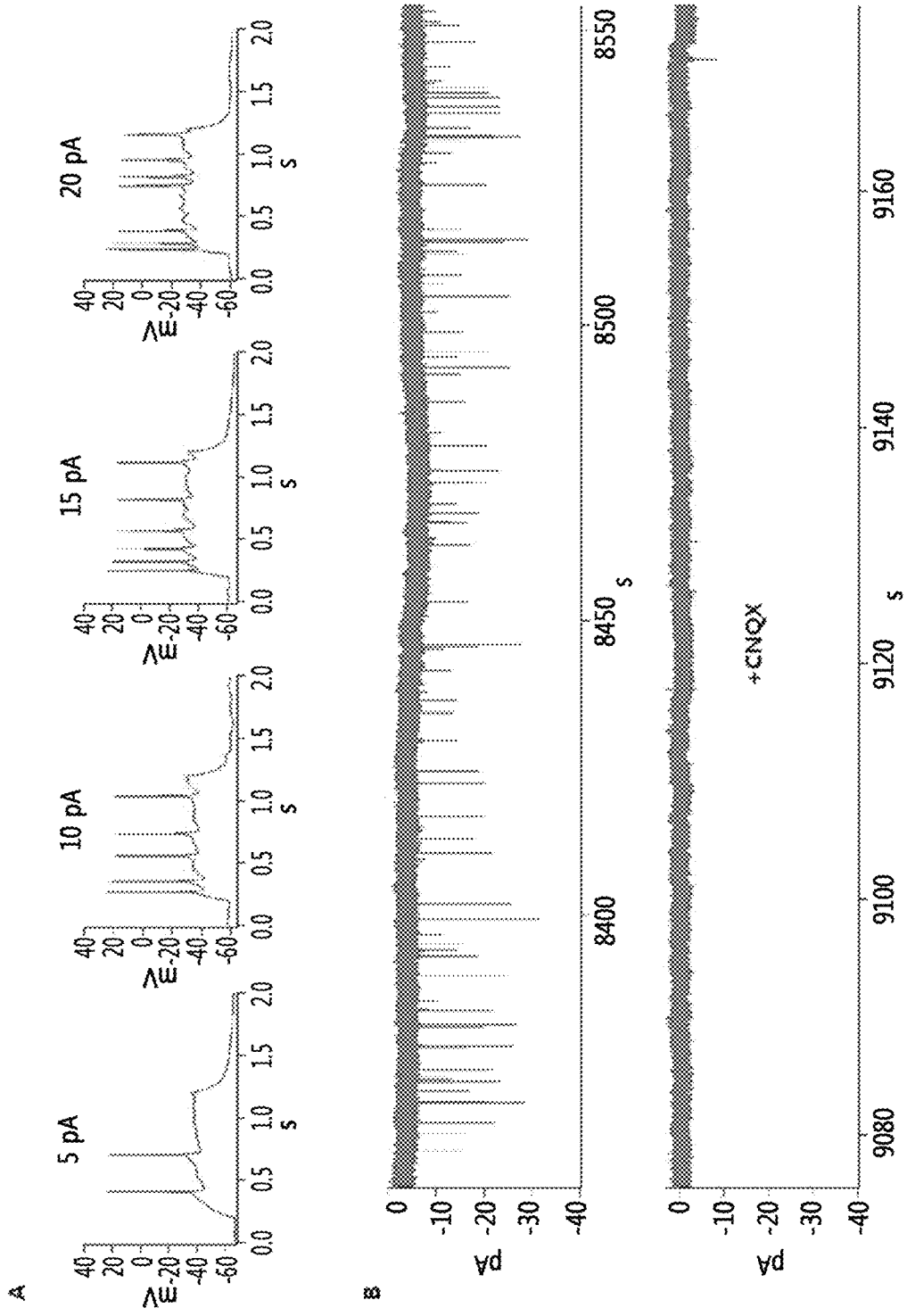

FIG. 17A-FIG. 17B shows the results of electrophysiological analysis on day 96 after induction of the differentiation of human embryonic stem cell line H9 according to Protocol B.

FIG. 17A shows a spiking train of action potentials is observed in response to step current injection (pA).

FIG. 17B shows spontaneous excitatory postsynaptic currents (sEPSCs) are observed. An AMPA receptor antagonist CNQX blocked the appearance of sEPSCs. Glutamatergic excitatory synapses are formed.

FIG. 18A-FIG. 18B shows the results of electrophysiological analysis on day 66 after induction of the differentiation of human embryonic stem cell line H9 according to Protocol C.

FIG. 18A shows a spiking train of action potentials is observed in response to step current injection (pA).

FIG. 18B shows spontaneous excitatory postsynaptic currents (sEPSCs) are observed. Glutamatergic excitatory synapses are formed.

Figures 19A, 19B:
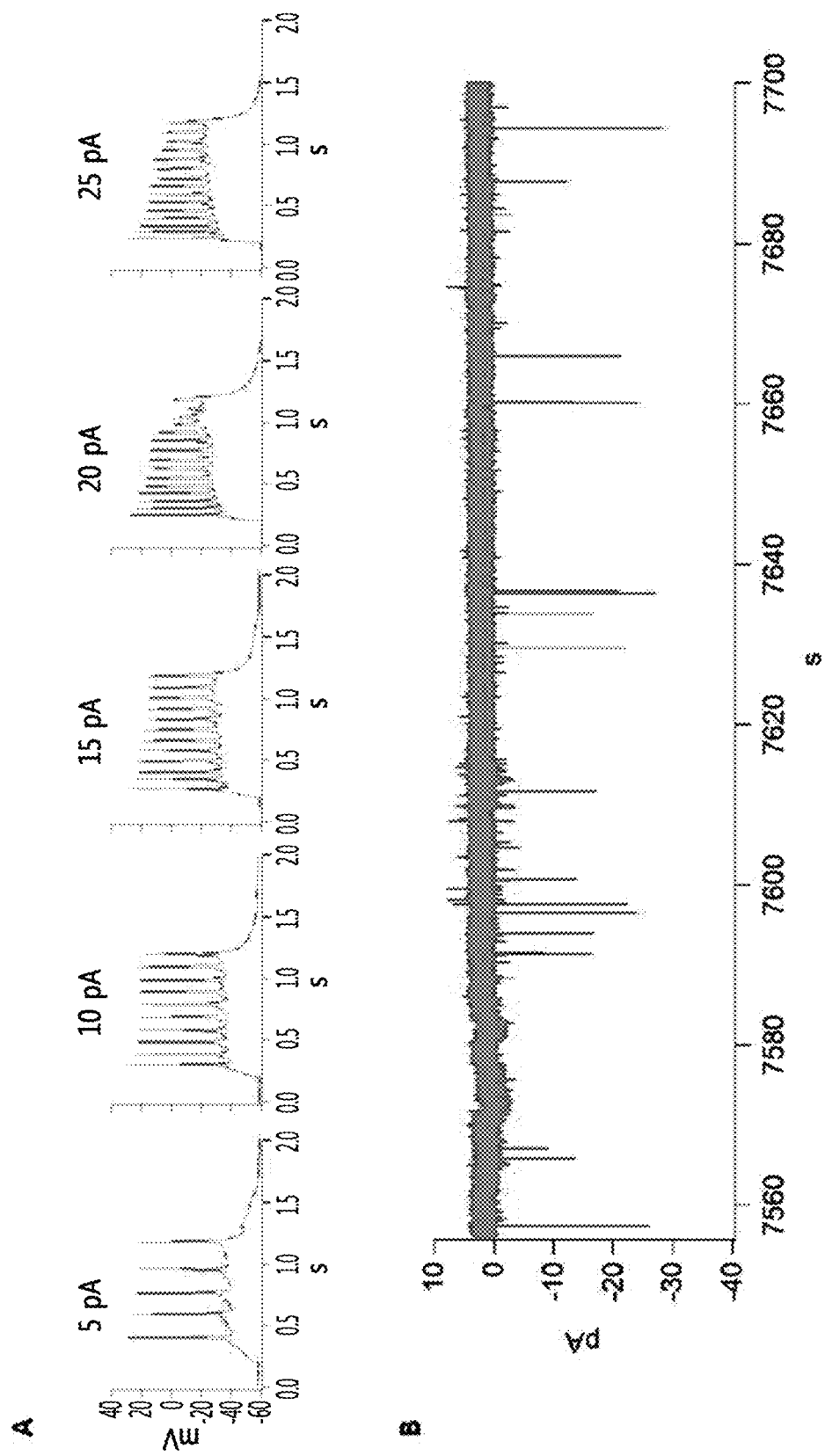

FIG. 19A-FIG. B shows the results of electrophysiological analysis of retinal ganglion cells which were matured while supplying a differentiation medium depleted of IGF-1, Shh, and RA (Retinoic acid) on day 39 after induction of the differentiation of human embryonic stem cell line H9 according to Protocol B.

FIG. 19A shows a robust regular-spiking train of action potentials is observed in response to step current injection (pA) in human embryonic stem cell-derived retinal ganglion cells on day 96 after induction of the differentiation.

FIG. 19B shows a spontaneous excitatory postsynaptic currents (sEPSCs) are observed in human embryonic stem cell-derived retinal ganglion cells on day 96 after induction of the differentiation. Glutamatergic excitatory synapses are formed.

Figure 20A:
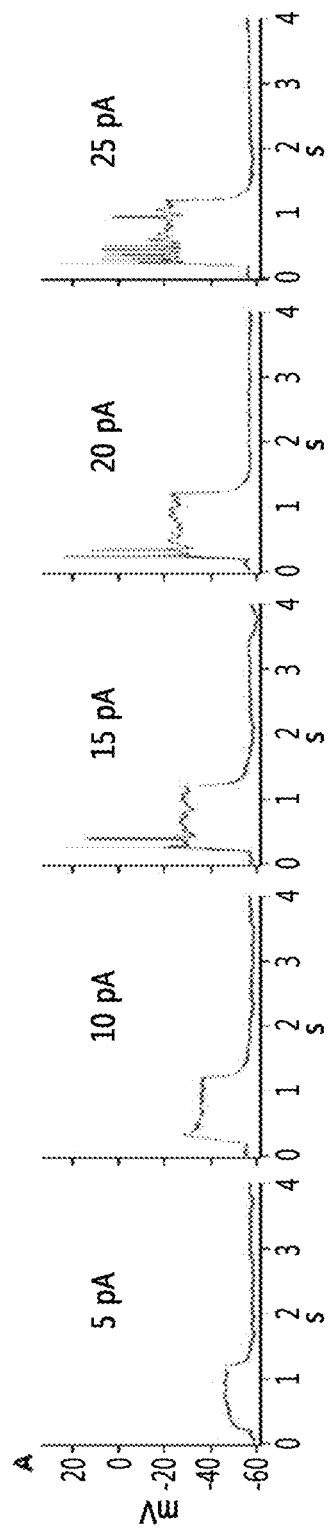
Figure 20B:
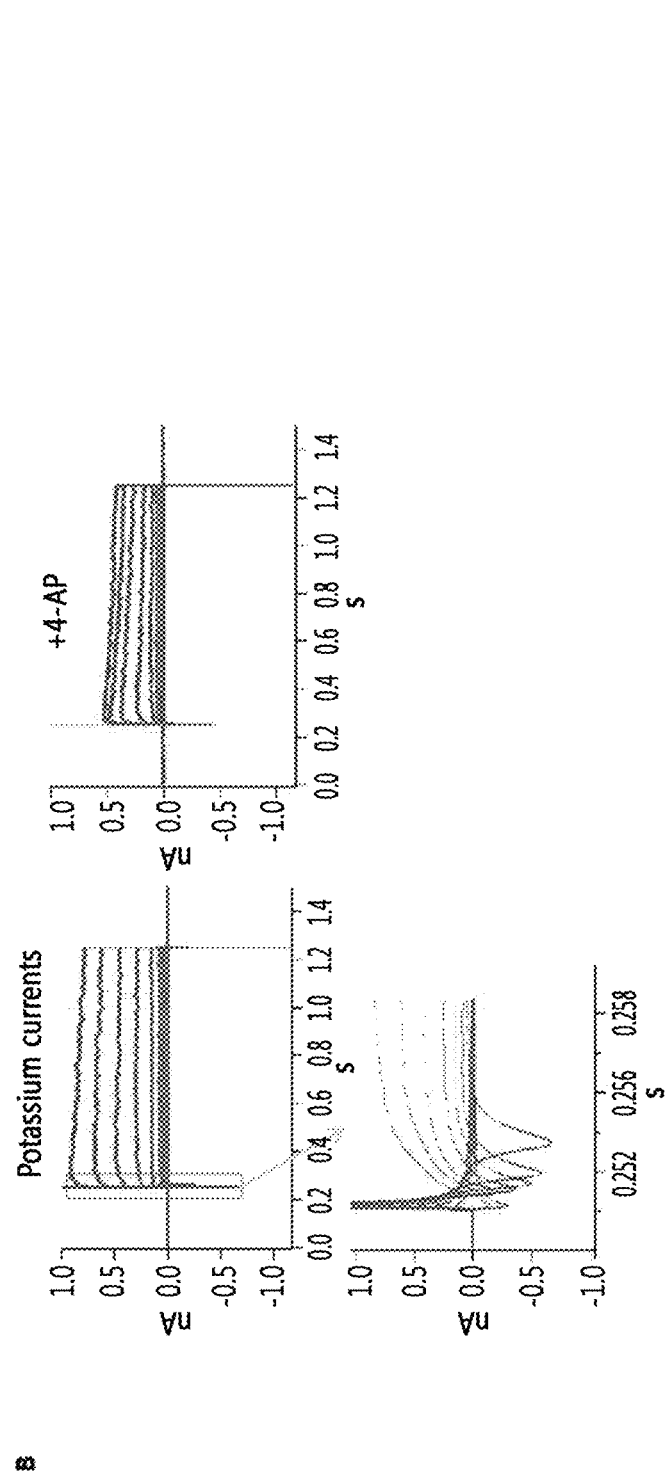

FIG. 20A-FIG. 20B shows the results of electrophysiological analysis on day 39 after induction of the differentiation of human induced pluripotent stem cells according to Protocol A.

FIG. 20A shows a robust regular-spiking train of action potentials is observed in response to step current injection (pA) in human induced pluripotent stem cell-derived retinal ganglion cells, indicating that the produced retinal ganglion cells acquired mature electrophysiological characteristics.

FIG. 20B shows Potassium current: 4-Aminopyridine (4-AP) blocked a fast-activating fraction of outward potassium current.

FIG. 21A-FIG. 21D shows differentiation of human embryonic stem cell-derived retinal ganglion cells by other Wnt signaling pathway and Shh receptor activators.

Differentiation was induced according to the time schedule of Protocol A using 2 μM of a Wnt signaling pathway activator BIO (6-bromoindirubin-3'-oxime), 50 ng/mL of Norrin, 1 μM of an Shh receptor activator purmorphamine, and 500 nM of retinoic acid (RA), in addition to Wnt3a used in the above differentiation method. Immunofluorescence staining results of the retinal ganglion cell markers, Islet-1 (red: nucleus) and NF200 (green: axon) in the cells on day 39 after induction of differentiation are consistent with the immunofluorescence staining results of Wnt3a and Shh.

Figures 21A, 21B, 21C, 21D:
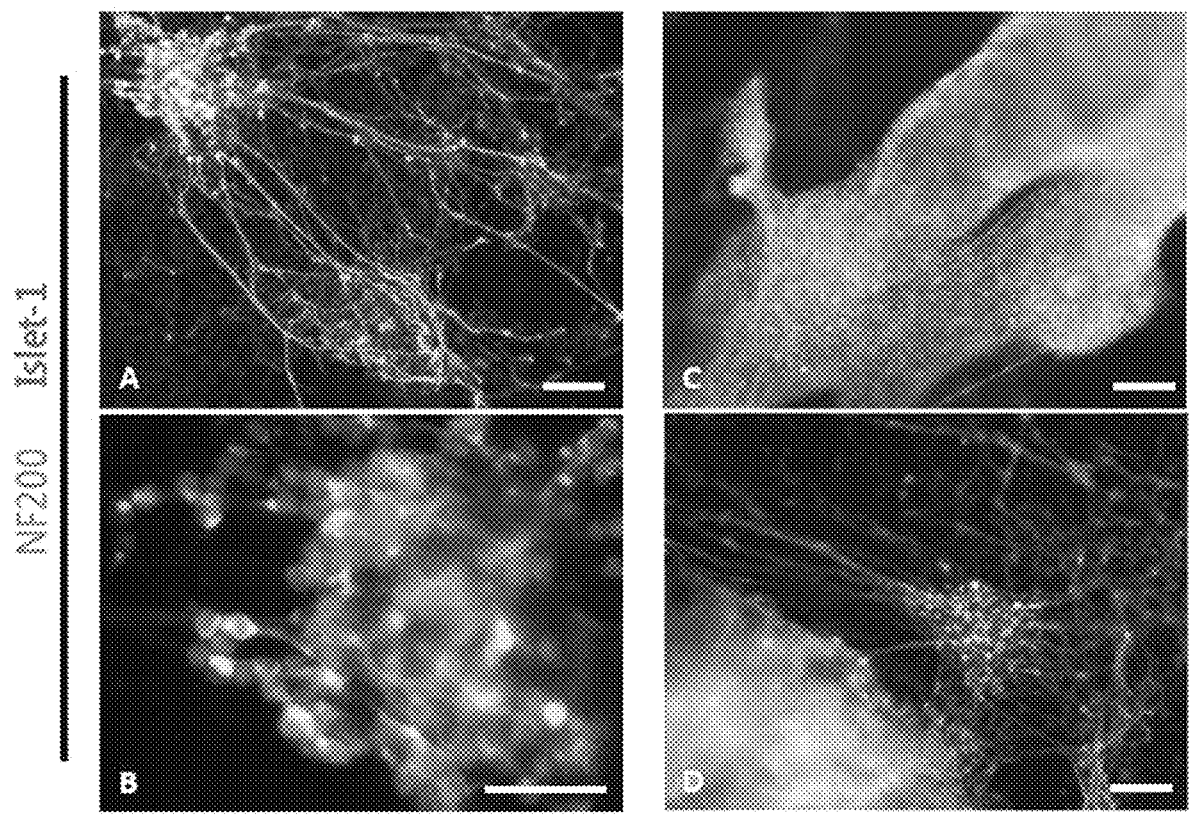

*Scale bar: FIG. 21A, FIG. 21C, FIG. 21D: 100 μm; FIG. 21B: 50 μm.

Figure 22:
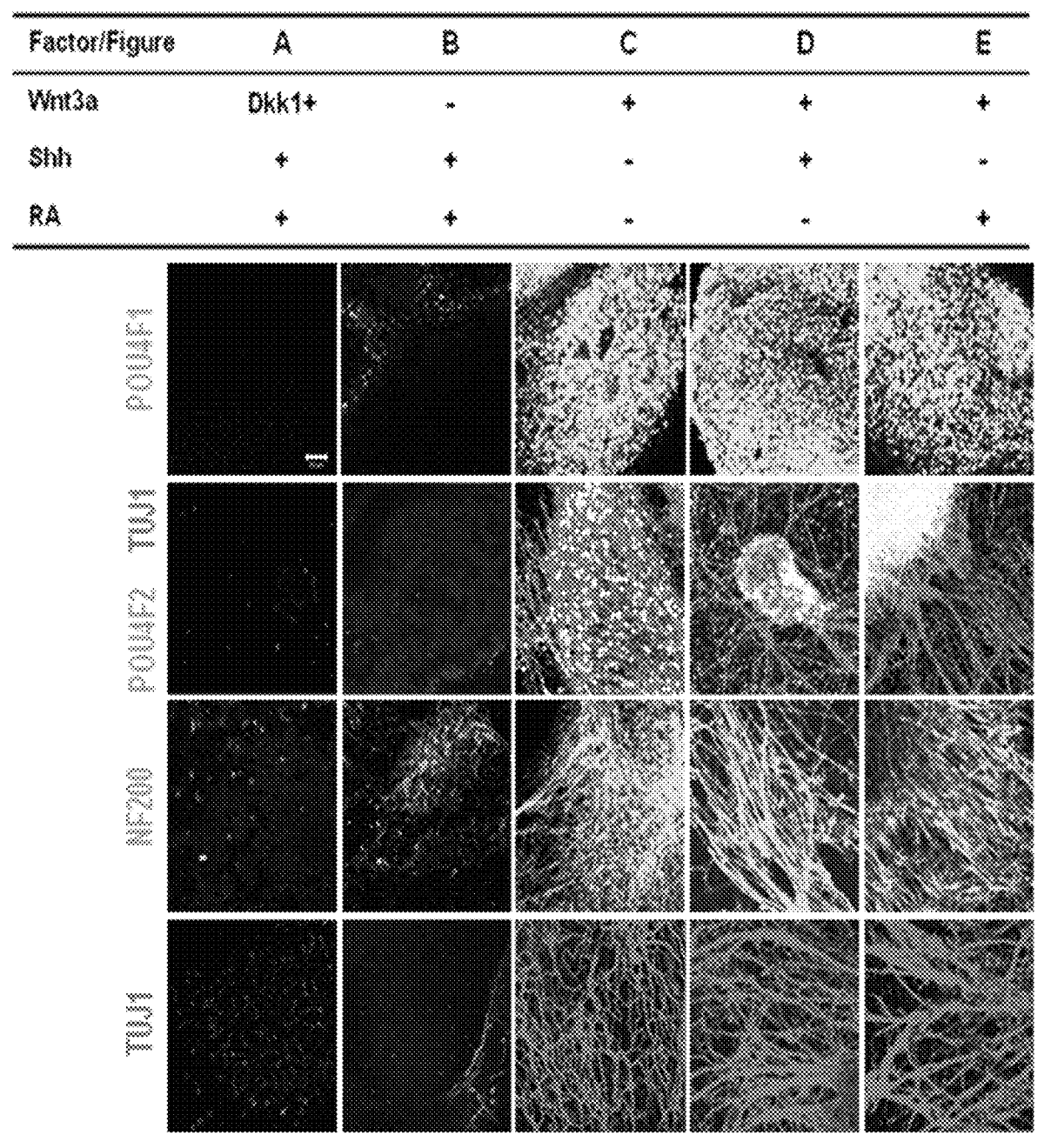

FIG. 22 shows the results of analyzing effects of Wnt3a, Shh and RA used in the Protocol A differentiation method for production of retinal ganglion cells. Respective factors were treated according to a differentiation schedule, and on day 39 after induction of differentiation, an immunofluorescence assay was performed using retinal ganglion cell-specific markers.

*Scale bar: 50 μm.

Figure 23A:
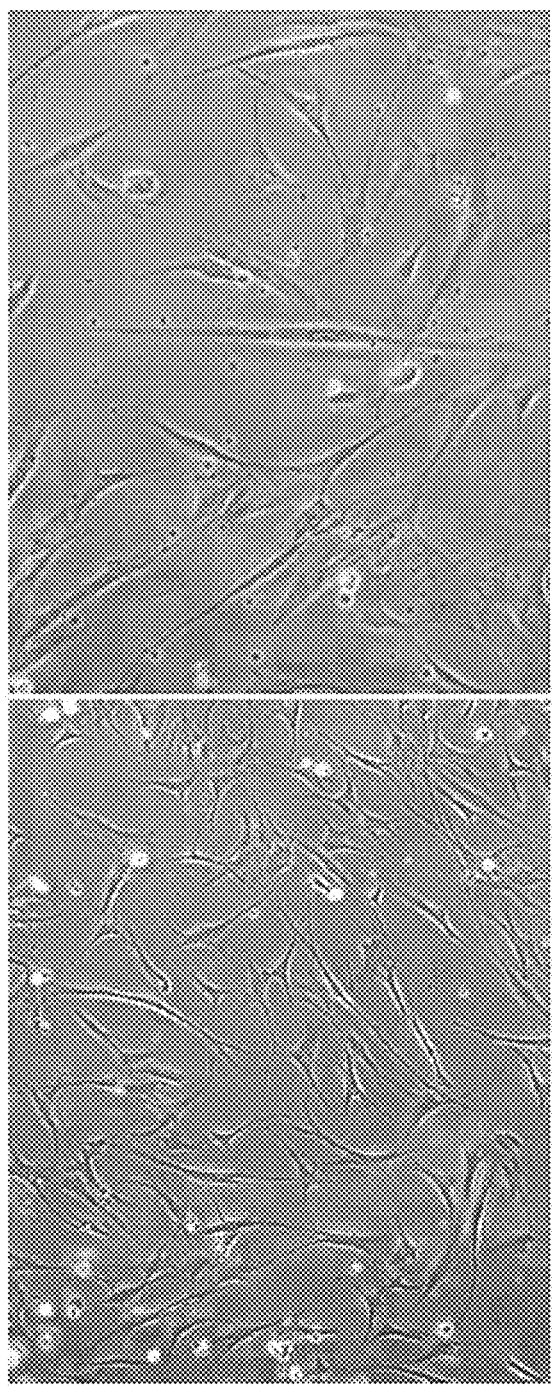
Figure 23B:
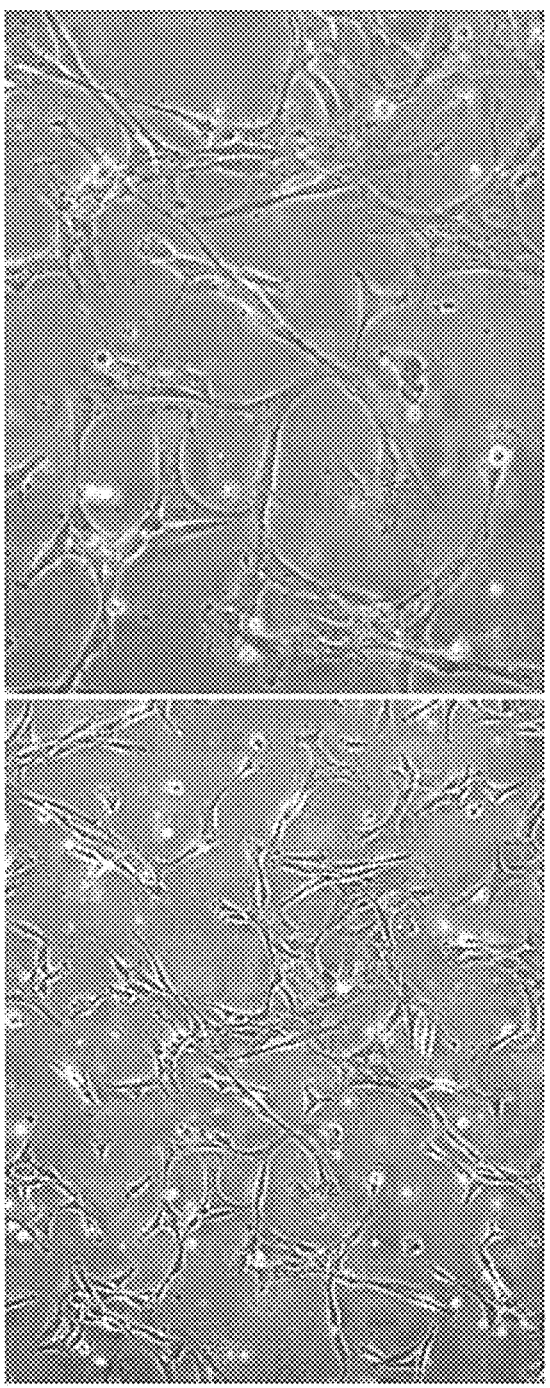

FIG. 23A-FIG. 23B shows cytomorphological microphotographs of human pluripotent stem cell-derived retinal ganglion cell line after subculture. The cells are those of passage number 16 after cell line establishment, that is, being cultured for 3 days from cells of passage number 15. The subcultured cells of the retinal ganglion cell line show neuronal morphology in vitro.

FIG. 23A shows a morphology of cells subcultured with Medium 1

FIG. 23B shows a morphology of cells subcultured with Medium 2

Both of the cells subcultured with Medium 1 and Medium 2 show a distinct neuronal morphology characterized by cytoplasmic elongation, long neuritis, and phase bright soma.

*left: phase-contrast microscope, 100× magnification; right: 200× magnification.

FIG. 24A-FIG. 24I shows the results of examining cell marker expressions of human pluripotent stem cell-derived retinal ganglion cell line. The cells are those of passage number 17 after cell line establishment, and immunofluorescence staining was performed at 3 days after passaging the cells of passage number 16. The characteristic markers of retinal ganglion cells are observed in almost all cells.

FIG. 24A shows Math5
FIG. 24B shows Brn3B
FIG. 24C shows Brn3A/Tuj1
FIG. 24D shows Synapsin1/Tuj1
FIG. 24E shows NF200
FIG. 24F shows KI67
FIG. 24G shows Thy1.2
FIG. 24H shows NMDAR1
FIG. 24I shows TrkB

*Scale bar: FIG. 24A to FIG. 24I: 50 μm. Nuclear staining: DAPI (blue).

Figure 25:
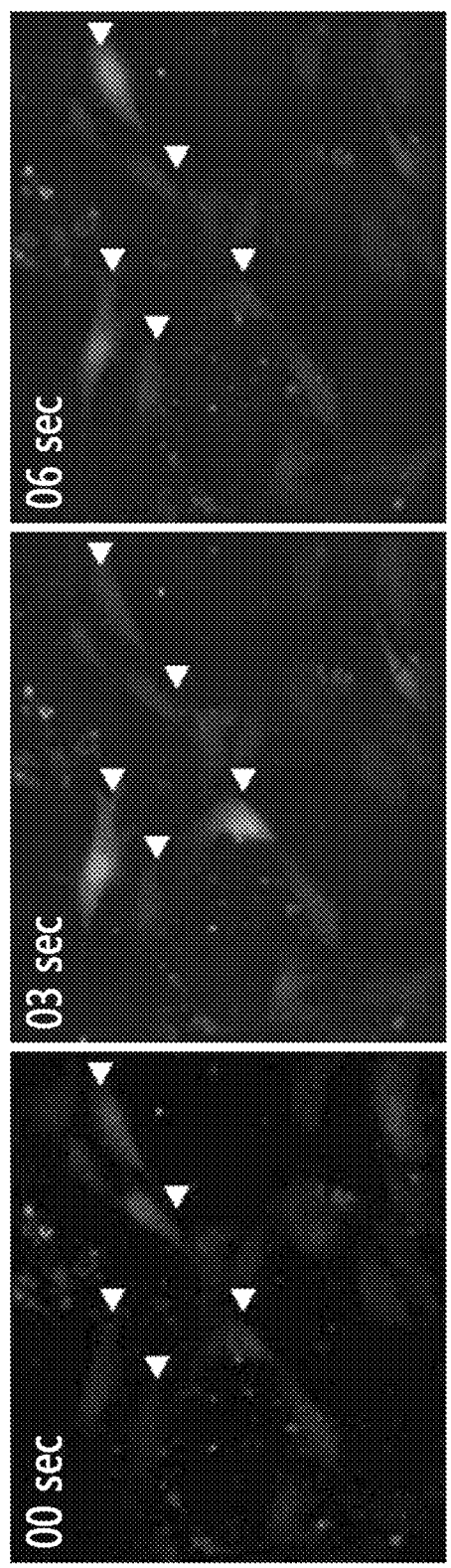

FIG. 25 shows microscopic imaging of intracellular calcium in human pluripotent stem cell-derived retinal ganglion cell line, indicating that the cells have neuronal functions. The human embryonic stem cell-derived retinal ganglion cells of passage number 15 were cultured for 3 days. The cells were treated with 1 μM of fluor-4 and stimulated with 1 mM glutamate, and then time differential images were obtained. As a result, calcium was detected in many live cells. A serial image spectrum from black (lowest) to white (highest) represents calcium concentration. In human embryonic stem cell-derived retinal ganglion cells, cytoplasmic calcium is considerably increased in response to glutamate stimulation (head of arrow).

BEST MODE

In order to achieve the above objects, an aspect of the present invention provides a method of preparing mature retinal ganglion cells by differentiation of stem cells into mature retinal ganglion cells, comprising (a) culturing retinal progenitor cells in a medium containing an IGF1R (insulin-like growth factor-1 receptor) activator and a Wnt signaling pathway activator to differentiate them into immature retinal ganglion cells; and (b) culturing the immature retinal ganglion cells in a medium prepared by removing the Wnt signaling pathway activator from the medium of step (a) and adding the IGF1R activator thereto.

Retina is one of the most well-studied organs in the central nervous system of vertebrates, and detailed morphology, synaptic connections of neurons, and physiological phenomena of retinal neurons have been investigated for decades. On the contrary, structural development of retinal neurons and various functional mechanisms thereof have not yet been clarified.

Of them, "retinal ganglion cells (RGCs)" are the output neurons present in the retina of vertebrate, and their axons form the optic nerve and send an image to the brain. A retinal ganglion cell is a neuron, that is, a nerve cell as the basic unit of the nervous system, and has a plurality of dendrites and a single long fibrous axon. The dendrites form synapses with one another to regulate electrical activity of neurons and to transmit electrical stimuli that flow into the cell body. The axon has many branching terminals containing granules or vesicles which release neurotransmitters in response to nerve stimulation. A synapse is a point of impulse transmission between neurons. Chemicals, called neurotransmitters, pass through a synaptic gap, and nerve impulse is maintained. During development, retinal ganglion cells are produced from multipotent retinal progenitor cells. For example, in mice, development of retinal ganglion cells begins at embryonic day (E) 11.5 and continues until postnatal day (P) 0, and reaches a peak at E14.5. A major expansion period is known to be between E14.5 and E17.5, which is variable depending on animals, but is not limited thereto.

The retinal ganglion cells function to transmit visual information from various cells of the retina to the optic nerve center of the brain. Light passed through the eye is converted to electrical signals in photoreceptor cells, and the electrical signals produced are transmitted to retinal ganglion cells via various neurons of the retina. Retinal ganglion cells function to receive these signals and to transmit them to the optic nerve center of the brain.

Development of retinal ganglion cells is regulated by a hierarchical gene regulatory network, and development and differentiation are mediated by major transcription factors.

The retinal ganglion cells may be divided into immature retinal ganglion cells and mature retinal ganglion cells according to differentiation degree.

The "immature retinal ganglion cells" refer to cells that acquire cytomorphological characteristics and protein and genetic marker characteristics of retinal ganglion cells (Barres, et al., Neuron. 1988; 1: 791-803.). The "mature retinal ganglion cells" refer to cells that are in the mature state as neurons after acquiring the above characteristics of the "immature retinal ganglion cells". That is, they have the morphological characteristics of axonal growth, arbor, and ring; dendritic arbor, stratification, and ring; dendritic spiny process; synaptic bouton; etc., and the protein and genetic marker characteristics of presynaptic or postsynaptic protein morphology and various receptor characteristics as excitatory nerves. The electrophysiological characteristics of the "mature retinal ganglion cells" are formation of spontaneous excitatory postsynaptic currents (sEPSCs), indicating functional maturation capable of forming synaptic connections between retinal ganglion cells (Pfrieger Barres, Science. 1997; 277: 1684-7.).

The "immature retinal ganglion cells" refer to cells at an early stage of differentiation from retinal progenitor cells into retinal ganglion cells. These immature retinal ganglion cells are cells that are fated to be retinal ganglion cells from retinal progenitor cells or cells that are fated to be retinal ganglion cells, but lack morphological and physiological characteristics of mature retinal ganglion cells. In the present invention, the immature retinal ganglion cells and early retinal ganglion cells are used interchangeably.

The "mature retinal ganglion cells" refer to retinal ganglion cells at a late stage of differentiation from retinal progenitor cells into retinal ganglion cells or retinal ganglion cells which have already differentiated. The mature retinal ganglion cells have a physiological characteristic of producing a high-frequency action potential and a morphological characteristic of having long axons, but are not limited thereto.

Whether retinal ganglion cells are immature retinal ganglion cells or mature retinal ganglion cells can be determined by identifying the expression levels of markers specific to respective cells, and morphological and physiological characteristics thereof (e.g., electrochemical characteristics).

First, transcription factors playing an important role in development and differentiation of retinal ganglion cells are as follows: transcription factors involved in the development of retinal ganglion cells are ATOH7 (Math5), Brn3 family (Brn3A, Brn3B, and Brn3C), and Isl1 (Islet-1).

ATOH7, also called Math5, is a factor involved in determining the fate of retinal progenitor cells to retinal ganglion cells, and is essential for formation of retinal ganglion cells. Therefore, Math5 is preferably expressed in the immature retinal ganglion cells.

Further, POU4F2 and POU4F1 (also called Brn3B and Brn3A, respectively) and Isl1 (Islet-1) downstream of ATOH7 in the gene network are known not to be required for the birth of RGC, but are known to be required for RGC differentiation and survival. They are known to be expressed at an early stage of differentiation of retinal ganglion cells and also expressed in mature retinal ganglion cells.

In detail, the Brn3 family is involved in regulation of RGC differentiation, dendritic stratification of RGCs, and axonal projection of RGCs during development. Of the Brn3 family, Brn3B is a factor expressed early during RGC development, and is one of the earliest RGC markers, and acts as an important factor in axon growth and survival of RGCs.

In mice, expression of Brn3A begins at embryonic day (E) 12.5, and in rats, Brn3A is expressed in 92.2% of the RGC population. Brn3B is known to act in axon formation of RGCs, whereas Brn3A is known to be involved in dendrite formation.

Isl1 is a homeodomain LIM protein expressed during retina development. Isl1 gene is activated immediately after the birth of RGCs, and its expression is identical with that of POU4F2 before the embryonic day (E) 14.5. Further, Isl1 is a factor required for RGC differentiation and survival, and its expression is governed by ATOH7. Isl1 expression is initiated at mouse embryonic day (E) 11.5 in completely divided cells, and Isl1 is known to be co-expressed with Brn3B in some of Brn3B-positive RGC cells.

The above transcription factors play an important role in generation of retinal ganglion cells, and thus immature retinal ganglion cells may express (1) Math5 and/or (2) one, specifically two, and more specifically three selected from the group consisting of Brn3B, Brn3A and Islet1. Further, expressions of these marker genes may be increased, compared to those in retinal progenitor cells, but are not limited thereto.

Further, the immature retinal ganglion cells may be those expressing NF200 or/and Tuj1. NF200 is a protein called neurofilament 200 kDa, and expressed at an early stage of differentiation of retinal ganglion cells. Tuj1 is also known to be expressed at an early stage of differentiation of retinal ganglion cells. Therefore, these two genes may be used to distinguish retinal ganglion cells, specifically, between immature retinal ganglion cells and mature retinal ganglion cells, but are not limited thereto. Additionally, marker genes specific to mature retinal ganglion cells are Thy1.2, TrkB, NMDAR1, Map2, Vglut1, PSD-95, synaptophysin, and synapsin1. These genes are marker genes known to be expressed in mature retinal ganglion cells.

Therefore, mature retinal ganglion cells may express one, specifically two, and more specifically 4, 5, 6, 7, 8, 9 and 10 marker genes selected from the group consisting of Brn3B, Brn3A, Islet-1, NF200, Tuj1, Thy1.2, TrkB, NMDAR1, Map2, Vglut1, PSD-95, synaptophysin and synapsin1, but are not limited thereto. Further, mature retinal ganglion cells may show high expressions of these genes, compared to retinal progenitor cells or immature retinal ganglion cells, but are not limited thereto.

The method of the present invention is a method capable of differentiating retinal progenitor cells into mature retinal ganglion cells via immature retinal ganglion cells in a high yield, characterized by culturing retinal progenitor cells in a medium containing a Wnt signaling pathway activator to differentiate them into immature retinal ganglion cells, and then culturing the immature retinal ganglion cells in a medium without the Wnt signaling pathway activator to differentiate them into mature retinal ganglion cells. That is, technical features of the present invention are to determine the fate of stem cells to retinal ganglion cells by treatment of stem cells at a specific differentiation stage with the Wnt signaling pathway activator and to differentiate 60% to 95% or more of various retinal cell populations into mature retinal ganglion cells by removing the Wnt signaling pathway activator. This method of inducing highly efficient differentiation into mature retinal ganglion cells was developed by the present invention for the first time.

A detailed description of the method of the present invention will be given below.

In the method of the present invention, step (a) is a step of culturing retinal progenitor cells in a medium containing an IGF1R activator and a Wnt signaling pathway activator to differentiate them into immature retinal ganglion cells. Step (a) may be performed for 1 day to 10 days, but is not limited thereto.

As used herein, the term "retinal progenitor cell" refers to a multipotent progenitor cell which can differentiate into cells present in the retina or retinal pigmented epithelial cells. The retinal progenitor cells are characterized by expressing one, two, or three or more markers selected from the group consisting of Rax, Pax6, Chx10, Otx2, Sox2, Lhx2, Six3, Six6 and Mitf, and in particular, by expressing one or two of Rax and Pax6, but are not limited thereto.

In connection with retinal development, as mentioned above, retinal progenitor cells are able to differentiate into various types of intraretinal cells (rod and cone photoreceptor cells, retinal ganglion cell, horizontal cells, bipolar cells, amacrine cells, Muller glial cells, etc.) and retinal pigmented epithelium, featuring positive expression of markers such as Crx, recoverin, rhodopsin, red/green opsin, blue opsin, peripherin2, PDE6B, SAG, Islet1/NF200, Prox1, PKC-a, Hu C/D, GFAP, ZO-1, and RPE65. However, the expression level and positive rate of these markers become weaker in retinal progenitor cells than in mature retinal cells or retinal pigmented epithelium, but are not limited thereto.

A medium for differentiation of retinal progenitor cells into immature retinal ganglion cells is characterized by containing all of the IGF1R activator and Wnt signaling pathway activator. Further, the medium for differentiation of retinal progenitor cells into immature retinal ganglion cells may contain, but is not limited to, a BMP (bone morphogenetic protein) signaling pathway inhibitor and an FGF (fibroblast growth factor) signaling pathway activator, in addition to the IGF1R activator and Wnt signaling pathway activator. Further, the medium may be a DMEM/F12 medium containing 1% B27 supplement and 1% N2 supplement in addition to the above-described materials, but is not limited thereto.

As used herein, the term "IGF1R activator" refers to a substance which activates IGF-1 (insulin-like growth factor-1) receptor (IGF1R), a member of the tyrosine kinase receptor family. Activated IGF1R interacts with insulin receptor substrates (IRS). In turn, IRS activated by IGF1R acts as an activator of one pathway consisting of PI3K, Akt, and mTOR, and the other pathway consisting of Raf, MEK, and ERK (Ryan & Goss, Oncologist. 2008; 13: 16-24). IGF-1 and IGF-2 fall within the range of the IGF1R activator. IGF-1, having a molecular structure similar to insulin, is implicated in cell growth, cell proliferation, differentiation, and cell death, but is not limited thereto.

Any IGF1R activator may be used without limitation in the present invention, as long as it activates IGF1R. It is exemplified by IGF-1 or IGF-2, and specifically, IGF-1, but is not limited thereto.

The medium used for differentiation of retinal progenitor cells into immature retinal ganglion cells contains the IGF1R activator in an amount of specifically 0.01 ng/mL to 100 ng/mL, more specifically 0.1 ng/mL to 50 ng/mL, much more specifically 1 ng/mL to 20 ng/mL, and most specifically 10 ng/mL, but is not limited thereto.

As used herein, the term "Wnt signaling pathway activator" refers to a substance activating the Wnt signaling pathway which is known to regulate various processes during embryogenesis, including cell fate determination, reconstruction of organization, polarity, morphology, adhesion and growth, and the maintenance and proliferation of undifferentiated cells. Any activator may be included within the Wnt signaling pathway without limitation, as long as it transduces Wnt-mediated or β-catenin-mediated signals. The Wnt signaling pathway is a series of processes that are initiated by the binding of a first trigger of the Wnt signaling pathway, Wnt, to its receptor or mediated by the stabilization of β-catenin, which is a downstream target in the intracellular Wnt signaling pathway. The Wnt signaling pathway activator is, but is not particularly limited to, as follows.

1) By directly adding a Wnt protein: Wnt, a first trigger of the Wnt signaling pathway, is a family of secreted glycoproteins. 19 Wnts have been identified: Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16b.

2) By increasing the level of β-catenin: Most cells respond to Wnt signaling pathway by an increase in the level of β-catenin. That is, an increase in dephosphorylated β-catenin level (or the stabilization) means the translocation of β-catenin into the nucleus.

3) By phosphorylation of dishevelled or phosphorylation of a Wnt-associated receptor, LRP tail.

4) By using GSK3 (glycogen synthase kinase 3) inhibitors: Lithium (Li), LiCl, bivalent Zn, BIO (6-bromoindirubin-3'-oxime), SB216763, SB415286, QS11 hydrate, TWS119, Kenpaullone, alsterpaullone, indirubin-3'-oxime, TDZD-8, and Ro 31-8220 methanesulfonate salt.

5) By blocking negative regulators of the Wnt signaling pathway, such as Axin and APC, or by using RNAi.

6) With activators of the Wnt pathway, such as norrin and R-spondin2: Norrin binds to Frizzled4 receptor while R-spondin2 interacts with Frizzled8 and LRP6.

7) By gene transfer, including transfection: Either Wnt overexpression constructs or β-catenin overexpression constructs may be used.

In the present invention, the Wnt signaling pathway activators may be employed without limitation as long as it is able to activate the Wnt signaling pathway. They are specifically Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; substances increasing β-catenin levels; GSK3 inhibitors such as lithium, LiCl, bivalent zinc, BIO, SB216763, SB415286, CHIR99021, QS11 hydrate, TWS119, Kenpaullone, alsterpaullone, indirubin-3'-oxime, TDZD-8 or Ro 31-8220 methanesulfonate salt; Axin inhibitors, APC inhibitors, norrin or R-spondin 2, and more specifically, Wnt3a, Wnt1, Wnt5a, Wnt11, Norrin, LiCl, BIO or SB415286, but are not particularly limited thereto.

The Wnt signaling pathway activator used for inducing differentiation of retinal progenitor cells into immature retinal ganglion cells may be used in an amount of 0.01 ng/mL to 500 ng/mL, specifically in an amount of 0.1 ng/mL to 200 ng/mL, and more specifically in an amount of 1 ng/mL to 100 ng/mL, except for LiCl, BIO and SB415286. Among the Wnt signaling pathway activators, the content of LiCl in the medium is 0.1 mM to 50 mM, specifically 0.5 mM to 10 mM, and more specifically 1 mM to 10 mM; the content of BIO in the medium is 0.1 µM to 50 µM, specifically 0.1 µM to 10 µM, and more specifically 0.5 µM to 5 µM; the content of SB415286 in the medium is 0.1 µM to 500 µM, specifically 1 µM to 100 µM, and more specifically 5 µM to 50 µM.

As used herein, the term "BMP signaling pathway inhibitor" means a group of substances capable of inhibiting BMP signaling pathway. BMPs belong to a signaling pathway protein belonging to the TGF-β (transforming growth factor-β) superfamily and are involved in early-prenatal differentiation, prenatal tissue formation, and homeostasis of adult tissues. Extracellular secreted BMPs bind to Type I and Type II serine/threonine kinase receptors, initiating the BMP signaling pathway. A Type II receptor phosphorylates a Type I receptor. The phosphorylated Type I receptor then phosphorylates the intracellular substrate Smad protein, mediating the intracellular signal transduction pathway. Smad proteins regulated by receptors are called R-Smads (Receptor regulated Smad), and Smad-1, 2, 3, 5 and 8 belong to R-Smads. They can bind the intracellular common partner Smad (Co-Smad) Smad-4. They migrate into and accumulate in the nucleus where they act as transcription factors and participate in the regulation of target gene expression (Yamamoto & Oelgeschlager, Naturwissenschaften. 2004; 91: 519-34). A BMP signaling pathway inhibitor refers to a substance which blocks the binding of extracellular BMP to cell-surface receptors. Examples of BMP signal pathway inhibitors include Noggin, chordin, twisted gastrulation (Tsg), cerberus, coco, gremlin, PRDC (protein related to DAN and Cerberus), DAN (differential screening-selected gene aberrative in neuroblastoma), dante, follistatin, USAG-1 (uterine sensitization-associated gene 1), dorsomorphin and sclerostin. By inhibiting BMP signal transduction, Noggin plays a key role in neural induction and in ventralizing dorsal neuroectoderm or mesoderm. Also, Noggin binds to the BMPs, BMP-2, BMP-4 and BMP-7, and blocks these BMPs from binding to their receptors (Yanagita, Cytokine Growth Factor Rev. 2005; 16: 309-17).

In the present invention, any BMP signaling pathway inhibitor may be employed, as long as it is able to inhibit BMP signal transduction. Examples thereof may include Noggin, chordin, twisted gastrulation, cerberus, coco, gremlin, PRDC, DAN, dante, follistatin, USAG-1 (uterine sensitization-associated gene 1), dorsomorphin and sclerostin, but are not limited thereto. In an embodiment of the present invention, Noggin was used.

In the present invention, the content of the BMP signaling pathway inhibitor in the medium for inducing differentiation of the retinal progenitor cells into immature retinal ganglion cells is 0.01 ng/mL to 100 ng/mL, specifically 0.1 ng/mL to 50 ng/mL, more specifically 0.5 ng/mL to 20 ng/mL, and most specifically 10 ng/mL, but is not limited thereto.

As used herein, the term "FGF signaling pathway activator" refers to a substance capable of inducing or promoting FGF signal transduction. FGF is a factor involved in mitogenesis including cell proliferation and cell differentiation, angiogenesis, bone morphogenesis and neural induction. Twenty-two members of the FGF family have been identified so far. There are four members of the FGF receptor family (FGFR). Their mRNAs bind to alternatively spliced receptor variants to activate the FGF receptors. Activated FGFR mediates the signal through a Ras/Raf/MeK pathway in the cytoplasm to activate MAP kinase, which in turn induces signal transduction (Bottcher & Niehrs, Endocr Rev. 2005; 26: 63-77). Of the FGF family, FGF2, also known as basic FGF (bFGF), binds mainly to FGFR 1b, FGFR 1c, FGFR 2c, FGFR 3c, and FGFR 44, and strongly activates FGFR 1c and FGFR 3c. Activators of FGFR 1c and FGFR 3c as well as FGF1, FGF4, FGF8, FGF9, FGF17, and FGF19 may be used as substitutes, but are not limited thereto.

In the present invention, any FGF signaling pathway activator may be used without limitation, as long as it is able to stimulate FGF signal transduction. Examples thereof may include an FGFR 1c or FGFR 3c activator, FGF1, FGF2, FGF4, FGF8, FGF9, FGF17 or FGF19, but are not limited thereto. In an embodiment of the present invention, FGF2 was used.

In the present invention, the content of the FGF signaling pathway activator in the medium for inducing differentiation of the retinal progenitor cells into immature retinal ganglion cells is 0.01 ng/mL to 100 ng/mL, specifically 0.1 ng/mL to 50 ng/mL, more specifically 1 ng/mL to 20 ng/mL, and most specifically 5 ng/mL, but is not particularly limited thereto.

Further, the retinal progenitor cells of step (a) may be obtained by (a') culturing stem cells in a medium containing an IGF1R activator, a Wnt signaling pathway inhibitor, and a BMP signaling pathway inhibitor to differentiate them into eye field precursors in the form of floating aggregates; and (b') culturing the eye field precursors of step (a') in the form of floating aggregates in a medium prepared by supplementing the medium of step (a') with an FGF signaling pathway activator to differentiate them into retinal progenitor cells.

Any stem cells may be used without particular limitation, as long as they are able to differentiate into retinal progenitor cells, and the stem cells may be selected from the group consisting of bone marrow stem cells (BMS), cord blood stem cells, amniotic fluid stem cells, fat stem cells, retinal stem cells (RSCs), intraretinal Muller glial cells, embryonic stem cells (ESCs), induced pluipotent stem cells (iPSCs), and somatic cell nuclear transfer cells (SCNTCs).

These stem cells may be differentiated into eye field precursors by culturing them in a medium containing an IGF1R activator, a Wnt signaling pathway inhibitor, and a BMP signaling pathway inhibitor. In this regard, the IGF1R activator, the BMP signaling pathway inhibitor, and concentrations thereof are the same as in the above medium used for inducing differentiation into immature retinal ganglion cells As used herein, the term "Wnt signaling pathway inhibitor" refers to a factor which interrupts interaction between the extracellular Wnt protein and the membrane protein Frizzled receptor or a co-receptor LRP, or inhibits intracellular Wnt-mediated signal transduction. In the present invention, any Wnt signaling pathway inhibitor may be used without particular limitation, as long as it inhibits Wnt-mediated signal transduction. Examples of the Wnt signaling pathway inhibitors may include the Dkk (Dickkopf) family (Dkk-1, Dkk-2, Dkk-3 and Dkk-4), which are antagonists of the co-receptor LRP, Wise, Wnt antagonists (sFRP: secreted Frizzled-related protein) family, a Frizzled-CRD domain, WIF-1 (Wnt inhibitory factor-1), IWP-2, IWP-3, IWP-4, cerberus, Wnt antibodies, dominant negative Wnt proteins, overexpression of Axin, overexpression of GSK (glycogen synthase kinase), dominant negative TCF, dominant negative dishevelled or casein kinase inhibitors (CKI-7, D4476 etc.), but are not limited thereto. In an embodiment of the present invention, Dkk-1 was used.

Further, Wnt signal transduction may be inhibited by suppressing each component involved in the Wnt pathway, such as RNAi, in addition to the Wnt signaling pathway inhibitor.

In the medium, the content of the Wnt signaling pathway inhibitor used for differentiating the stem cells into retinal progenitor cells via eye field precursors may be 0.01 ng/mL to 10,000 ng/mL, but is not particularly limited thereto.

As used herein, the term "eye field precursor" refers to a cell expressing specific markers (eye field transcription factors; Zuber, et al., Development, 2003; 130: 5155-67) found in a progenitor for the eye field of the forebrain neural plate during embryonic development. The eye field precursors are characterized by expressing one, two, or three or more markers selected from the group consisting of Six3, Rax, Pax6, Otx2, Lhx2 and Six6, but are not limited thereto.

The eye field precursors have a morphology of floating aggregates. In this regard, the floating aggregate refers to a cell mass floating in a medium which is generated when a floc of embryonic stem cells is cultured for at least one day in a non-adhesive plate without feeding mouse embryonic fibroblasts (MEF) and sera. Depending on the composition of the medium supplied, the eye field precursors may express eye field transcription factors.

Further, step (a') may be performed for 1 day to 30 days, and step (b') may be performed for 5 days to 15 days, but are not limited thereto.

In the present invention, the floating aggregates of eye field precursors of step (b') may be grown adhering to a plate which is coated with an extracellular matrix selected from the group consisting of poly-D-lysine, laminin, poly-L-lysine, matrigel, agar, polyornithine, gelatin, collagen, fibronectin and vitronectin.

The cell population per floating aggregate which adheres to the plate is the number of cells which is the most highly efficient. A floating aggregate of eye field precursors may consist of 200 cells to 400 cells, but is not limited thereto.

Further, the medium of step (a') may be a DMEM/F12 medium further containing 10% knockout serum replacement and 1% B27 supplement, in addition to an IGF1R activator, a Wnt signaling pathway inhibitor, and a BMP signaling pathway inhibitor.

Meanwhile, the medium of step (b') may be a DMEM/F12 medium further containing 1% B27 supplement and 1% N2 supplement, in addition to the above-described IGF1R activator, Wnt signaling pathway inhibitor, BMP signaling pathway inhibitor, and FGF signaling pathway activator.

In the method of the present invention, step (b) is a step of culturing immature retinal ganglion cells which are differentiated in step (a). Immature retinal ganglion cells may be differentiated into mature retinal ganglion cells by step (b).

For highly efficient differentiation into mature retinal ganglion cells, the medium used in step (b) is characterized by containing no Wnt signaling pathway activator which is contained in the medium of step (a).

More specifically, step (b) may be a step of culturing the cells of step (a) in a medium prepared by removing the BMP signaling pathway inhibitor, the FGF signaling pathway activator, and the Wnt signaling pathway activator from the medium of step (a), and more specifically, in a medium prepared by removing the BMP signaling pathway inhibitor, the FGF signaling pathway activator, and the Wnt signaling pathway activator from the medium of step (a) and adding an Shh (sonic hedgehog) signaling pathway activator thereto.

Further, step (b) may comprise (i) culturing immature retinal ganglion cells in a medium containing the IGF1R activator, the BMP signaling pathway inhibitor, and the FGF signaling pathway activator by removing the Wnt signaling pathway activator from the medium of step (a); and (ii) culturing immature retinal ganglion cells in a medium prepared by removing the BMP signaling pathway inhibitor and the FGF signaling pathway activator from the medium of step (i) and adding an Shh (sonic hedgehog) signaling pathway activator thereto.

Meanwhile, as used herein, the term "removing" may be interpreted as using a medium that does not contain a subject to be removed. Also, the term "a medium whose composition does not comprise X" means all of the medium that does not contain X.

Further, the medium may be a DMEM/F12 medium containing 1% B27 supplement and 1% N2 supplement, in addition to the above-described substances, but is not limited thereto.

As used herein, the term "Shh (sonic hedgehog) signaling pathway activator" refers to a substance that induces or activates the Shh signal transduction. Shh is known as a signal transducer associated with the regulation of various processes during embryogenesis, including cell fate determination, polarity, morphology, proliferation, and differentiation (Bertrand & Dahmane, Trends Cell Biol. 2006; 16: 597-605). The Shh signaling pathway involves two transmembrane proteins, Ptc (Patched) and Smo (Smoothened). In the absence of Shh, Ptc interacts with and inhibits Smo. On the contrary, in the presence of shh, Shh binds to Ptc, and Smo is no longer inhibited, leading to Ci/Gli protein in the cytoplasm entering the nucleus and acting as a transcriptional activator for target genes. No particular limitations are imparted to the Shh signaling pathway activator if it is able to enhance the Shh-mediated signaling pathway. Examples of the Shh signaling pathway activators may include proteins belonging to the hedgehog family (e.g., Shh), inhibitors of inhibitory function of Ptc on Smo, Smo receptor activators, Shh receptor activators (e.g. Hg—Ag, purmorphamine, etc.), substances increasing Ci/Gli family levels, inhibitors of the intracellular degradation of Ci/Gli proteins, and Shh overexpression constructs or Ci/Gli overexpression constructs resulting from transfection.

In the present invention, any Shh signaling pathway activator may be used, as long as it is able to activate the Shh signaling pathway. Examples thereof may include Shh, Smo receptor activators, inhibitors of inhibitory function of Ptc on Smo, substances increasing Ci/Gli family levels, inhibitors of the intracellular degradation of Ci/Gli factors, and an Shh receptor activator, Hg—Ag or purmorphamine, but are not limited thereto. More specific examples of the Shh signaling pathway activator may include Shh and purmorphamine.

In the present invention, the content of the Shh signaling pathway activator in the medium used for differentiating immature retinal ganglion cells into mature retinal ganglion cells is 0.1 ng/mL to 5,000 ng/mL, specifically 1 ng/mL to 2,500 ng/mL, more specifically 10 ng/mL to 1,000 ng/mL, and most specifically 250 ng/mL, but is not particularly limited thereto.

Step (b) may be performed for 1 day to 200 days.

For highly efficient differentiation into mature retinal ganglion cells, the method may further include the step of (c) culturing the cells cultured in step (b) in a medium prepared by adding RA (retinoic acid) to the medium of step (b).

As used herein, the term "RA (retinoic acid)" refers to a metabolite of vitamin A, which is a lipophilic molecule. There are two types of RA: all-trans retinoic acid and 9-cis retinoic acid. RA is translocated into the nucleus where it binds to RARs (retinoic acid receptors) and RXR (retinoid X receptors) respectively and participates in the regulation of target gene transcription, but is not limited thereto.

RA used in the method of the present invention may be trans-retinoic acid and cis-retinoic acid, and the concentration of RA to be used may be 0.5 nM to 10,000 nM, specifically 5 nM to 5,000 nM, more specifically 50 nM to 2,000 nM, and much more specifically 500 nM, but is not particularly limited thereto.

Step (c) may be performed for 1 day to 120 days, but is not limited thereto.

The method of the present invention may further include the step of (d) culturing immature retinal ganglion cells or mature retinal ganglion cells in a medium prepared by removing one or more, two or more, or three selected from the group consisting of an IGF1R activator, Shh signaling pathway activator, and RA, more specifically, by removing all of the IGF1R activator, Shh signaling pathway activator and RA from the medium of step (c).

According to embodiments of the present invention, although immature retinal ganglion cells undergoing maturation were cultured in a medium free of all of the IGF1R activator, Shh signaling pathway activator, and RA, they showed maturity equivalent to those cultured in a medium containing all of the components.

Further, the method of the present invention may include the step of determining whether the desired cells after the above-described step, for example, immature retinal ganglion cells after step (a), are differentiated or not, or determining whether mature retinal ganglion cells after step (b), (c) or (d) are differentiated or not.

Differentiation of the desired cells, specifically, immature retinal ganglion cells and mature retinal ganglion cells, may be determined by measuring expressions of marker genes specific to the cells, and/or by identifying morphological characteristics and/or physiological characteristics.

The measurement of the marker gene expression may be performed by measuring the expression level of mRNA or protein of the marker gene, and measurement of the expression level may be performed by using various methods known in the art.

Any technique of analyzing the marker gene expression at an mRNA level may be used in the present invention without limitations, as long as it is a method of analyzing mRNA well-known in the art. Examples thereof may include reverse transcriptase polymerase chain reaction, competitive reverse transcriptase polymerase chain reaction, real-time polymerase chain reaction, Rnase Protection Assay, Northern blotting, and DNA chip assay.

Further, any technique of analyzing the marker gene expression at a protein level may be used in the present invention without limitations, as long as it is a method of analyzing a protein well-known in the art. Examples thereof may include Western blotting, ELISA, radioimmunoassay, radioimmunodiffusion, Ouchterlony immunodiffusion, rocket immunoelectrophoresis, immunohistostaining, immunoprecipitation assay, complement fixation assay, FACS, and protein chip assay.

Compared to the pre-differentiative retinal progenitor cells, the mature retinal ganglion cells differentiated according to the present invention exhibit one or more of the following features: (1) an increased expression level of Brn3B; (2) an increased expression level of Brn3A; (3) an increased expression level of Islet1; (4) an increased expression level of NF200; (5) an increased expression level of Tu1l; (6) an increased expression level of Thy1.2; (7) an increased expression level of TrkB; (8) an increased expression level of NMDAR1; (9) an increased expression level of Map2; (10) an increased expression level of Vglut1; (11) an increased expression level of PSD-95; (12) an increased expression level of Synaptophysin; and (13) an increased expression level of Synapsin1.

An increase or decrease in the expression levels of the genes may be identified using antibodies against the proteins encoded by the genes or using methods well-known to those skilled in the art, such as RT-PCR. As they show more of the features, the differentiated cells are defined as being closer to the mature retinal ganglion cells. Preferably, the mature retinal ganglion cells show one or more, specifically 2 or more, more specifically 3 or more, much more specifically 4 or more, and most specifically 5 or more of the features. Preferably, more than approximately 40%, 60%, 80%, 90%, 95% or 98% of the population of the cells after differentiation according to the method of the present invention have the desired features. Higher ratios are more preferable, but are not limited thereto.

Another aspect of the present invention provides a method of differentiating immature retinal ganglion cells into mature retinal ganglion cells, including the step of culturing the immature retinal ganglion cells in a medium containing the IGF1R activator and the Shh signaling pathway activator.

The immature retinal ganglion cells, IGF1R activator, Shh signaling pathway activator, and mature retinal ganglion cells are the same as described above.

The medium which is not applied to the method of differentiating immature retinal ganglion cells into mature retinal ganglion cells is characterized by containing no Wnt signaling pathway activator.

In the method, the IGF1R activator may be used specifically in an amount of 0.01 ng/mL to 100 ng/mL, more specifically in an amount of 0.1 ng/mL to 50 ng/mL, much more specifically in an amount of 1 ng/mL to 20 ng/mL, and most specifically in an amount of 10 ng/mL, but is not particularly limited thereto.

In the method, the Shh signaling pathway activator may be used in an amount of 0.1 ng/mL to 5,000 ng/mL, specifically in an amount of 1 ng/mL to 2,500 ng/mL, more specifically in an amount of 10 ng/mL to 1,000 ng/mL, and most specifically in an amount of 250 ng/mL, but is not particularly limited thereto.

Further, the medium may be a DMEM/F12 medium containing 1% B27 supplement and 1% N2 supplement in addition to the above-described substances, but is not limited thereto.

The method may further include the step of culturing immature retinal ganglion cells in a medium prepared by adding RA (retinoic acid) to the medium containing the IGF1R activator and the Shh signaling pathway activator. Herein, "adding" may be interpreted as replacing the previous medium with a fresh medium containing the above substance together with the previous medium composition, as well as adding the substance to the medium.

Herein, RA is the same as described above, and the concentration of RA to be used may be 0.5 nM to 10,000 nM, specifically 5 nM to 5,000 nM, more specifically 50 nM to 2,000 nM, and much more specifically 500 nM, but is not particularly limited thereto.

The method may further include the step of culturing immature retinal ganglion cells or mature retinal ganglion cells in a medium prepared by removing one or more selected from the group consisting of an IGF1R activator, Shh signaling pathway activator, and RA, and more specifically, all of the IGF1R activator, Shh signaling pathway activator, and RA from the above-described medium.

Still another aspect of the present invention provides immature retinal ganglion cells and mature retinal ganglion cells prepared according to the above-described method of the present invention.

The method, the immature retinal ganglion cells, and the mature retinal ganglion cells are the same as described above.

Still another aspect of the present invention provides a method of screening for a death inhibitor or a proliferation promoter of mature retinal ganglion cells, comprising (a) treating the mature retinal ganglion cells obtained and isolated by the above method of differentiating into mature retinal ganglion cells with a death inhibitor candidate or a proliferation promoter candidate of mature retinal ganglion cells; and (b) determining that the candidate is a death inhibitor or a proliferation promoter of mature retinal ganglion cells when the candidate inhibits death of the mature retinal ganglion cells or promotes proliferation of the mature retinal ganglion cells, compared to a non-candidate-treated group.

The method of differentiating into mature retinal ganglion, and the mature retinal ganglion cells are the same as described above.

Step (a) is a step of treating the mature retinal ganglion cells obtained and isolated by the above method of differentiating into mature retinal ganglion cells according to the present invention with a death inhibitor candidate or a proliferation promoter candidate of mature retinal ganglion cells.

The mature retinal ganglion cells to be treated with the candidate may be, but is not particularly limited to, mature retinal ganglion cells which are differentiated by applying the method of the present invention to stem cells derived from a healthy person or a patient.

As used herein, the term "death inhibitor of mature retinal ganglion cells" refers to a substance capable of inhibiting death of mature retinal ganglion cells. Specifically, the death inhibitor may include a substance capable of reducing death of mature retinal ganglion cells, to which death induction conditions of mature retinal ganglion cells are applied, compared to those to which the death induction conditions are not applied. The type of the death inhibitor is not particularly limited, and the death inhibitor includes compounds, proteins, peptides, and nucleic acids.

As used herein, the term "proliferation promoter of mature retinal ganglion cells" refers to a substance capable of inducing or promoting proliferation of mature retinal ganglion cells. Specifically, the proliferation promoter may include a substance capable of increasing proliferation of mature retinal ganglion cells, to which the proliferation promoter is applied, compared to those to which the proliferation promoter is not applied. The type of the proliferation promoter is not particularly limited, and the proliferation promoter includes compounds, proteins, peptides, and nucleic acids.

The method of the present invention may include the step of (b) determining that the candidate is a death inhibitor or a proliferation promoter of mature retinal ganglion cells when the candidate inhibits death of the mature retinal ganglion cells or promotes proliferation of the mature retinal ganglion cells, compared to a non-candidate-treated group. Further, the death inhibitor or proliferation promoter of mature retinal ganglion cells may be a therapeutic agent for glaucoma or optic neuropathy.

As used herein, the term "glaucoma" refers to a disease having optic nerve damage accompanied by loss of retinal ganglion cells.

As used herein, the term "optic neuropathy" refers to a disease resulting from visual disorders caused by gradual loss of the retinal ganglion cells and their axons which constitute the retina. The optic neuropathy includes optic neuritis, ischemic optic neuropathy, toxic or deficiency optic neuropathy, hereditary optic neuropathy, and optic atrophy.

As described above, glaucoma and optic neuropathy are diseases accompanied by loss of retinal ganglion cells, and thus a substance capable of inhibiting death of retinal ganglion cells or promoting proliferation thereof may be used as a therapeutic agent for glaucoma or optic neuropathy.

Still another aspect of the present invention provides a kit of screening for the death inhibitor or the proliferation promoter of mature retinal ganglion cells, including the mature retinal ganglion cells prepared by the above-described method of the present invention. Further, the kit may be used for screening of the therapeutic agent for glaucoma or optic neuropathy.

The mature retinal ganglion cells, the death inhibitor, and the proliferation promoter are the same as described above.

The kit may include various tools and/or reagents capable of screening the death inhibitor or proliferation promoter of retinal ganglion cells in addition to mature retinal ganglion cells, which are known in the art. If necessary, the kit may further include a tube for mixing each component, a well plate, and an instruction manual describing use thereof.

Experimental procedures, reagents, and reaction conditions that may be used in the methods may be those commonly known in the art and will be obvious to those skilled in the art.

Still another aspect of the present invention provides a pharmaceutical composition for treating glaucoma or optic neuropathy, including the mature retinal ganglion cells prepared by the above-described method of the present invention.

The mature retinal ganglion cells, glaucoma and optic neuropathy are the same as described above.

For use in the therapeutic composition of the present invention, differentiation of mature retinal ganglion cells from stem cells, for example, human embryonic stem cells or induced pluripotent stem cells, is induced in vitro, mature retinal ganglion cells are proliferated and differentiated in a large amount and then administered to a patient having the above disease. The therapeutic composition may be formulated into dosage forms general in the art, for example, injectable formulations. The composition may be directly transplanted into a retinal site using a surgical procedure or may be intravenously injected and migrate to a retinal site. The therapeutic composition of the present invention may further include an immunosuppressant to suppress immune rejection responses to grafts. The composition may further include a pharmaceutically acceptable carrier. The administration dose of the therapeutic composition of the present invention may vary depending on the severity of the patient, the route, method, and frequency of administration, the time period of treatment, the patient's age, sex, and disease severity, and may be easily determined by those skilled in the art according to various factors well-known in the medical art.

Still another aspect of the present invention provides a method of treating glaucoma or optic neuropathy, including the step of administering the mature retinal ganglion cells prepared by the method of the present invention to a subject suspected of having glaucoma or optic neuropathy.

The method, mature retinal ganglion cells, glaucoma and optic neuropathy are the same as described above.

The mature retinal ganglion cells of the present invention may be administered to any animal, and the animal may include livestock, such as cows, pigs, sheep, horses, dogs, mice, rats, cats, etc., as well as humans and primates.

As used herein, the term "administration" refers to the introduction of the composition of the present invention into a subject suspected of having glaucoma or optic neuropathy by a suitable route, including the transplantation of the differentiated cells. Any administration route by which the composition of the present invention reaches a tissue of interest may be employed in the present invention. Intraretinal injection is preferred.

Still another aspect of the present invention provides a method of preparing a mature retinal ganglion cell line, comprising (a) culturing retinal progenitor cells in a medium containing the IGF1R (insulin-like growth factor-1 receptor) activator and the Wnt signaling pathway activator to differentiate them into immature retinal ganglion cells; and (b) culturing the immature retinal ganglion cells in a medium prepared by removing the Wnt signaling pathway activator from the medium of step (a) and adding the IGF1R activator thereto.

The medium may further include the Shh signaling pathway activator or RA (retinoic acid), or both.

Further, the method may further comprise separating the cells that are cultured in the medium containing the IGF1R activator and the Shh signaling pathway activator, and then culturing the cells in (i) a medium containing L-glutamine, mercaptoethanol, and insulin/transferrin/selenium-X, or (ii) a medium containing L-glutamine, mercaptoethanol, FGF2, IGF-1 and EGF. The medium may specifically be an IMDM medium containing L-glutamine, mercaptoethanol, and insulin/transferrin/selenium-X, or an IMDM medium containing L-glutamine, mercaptoethanol, FGF2, IGF-1 and EGF. In an embodiment of the present invention, Medium 1 containing IMDM, 15% FBS, 1 mM L-glutamine, 0.1 mM mercaptoethanol, and 1% insulin/transferrin/selenium-X, and Medium 2 containing IMDM, 15% FBS, 1 mM L-glutamine, 0.1 mM mercaptoethanol, 5 ng/mL of FGF2, 10 ng/mL of IGF-1, and 5 ng/mL of human recombinant EGF were used.

MODE FOR INVENTION

Hereinafter, the present invention will be described in detail with reference to Examples. However, these Examples are for illustrative purposes only, and the invention is not intended to be limited by these Examples.

EXAMPLE 1

Culture of Stem Cells

<1-1> Culture of Human Embryonic Stem Cells

Human embryonic stem cell (hESC) lines H9 (WA09, normal karyotype XX) and H7 (WA07, normal karyotype, XX) were purchased from the WiCell Research Institute (Madison, Wis.).

The human embryonic stem cells were allowed to proliferate undifferentiated (H9 cells: passages 26 to 41; H7 cells: passages 23 to 32) by culturing them over feeder cells, such as irradiated mouse embryonic fibroblasts (MEF, Global Stem, Gaithersburg, Md.) or mitomycin-treated mouse embryonic fibroblasts (EmbryoMax Primary Mouse Embryo Fibroblasts, Millipore, Billerica, Mass.) in the following medium: embryonic stem cell medium [DMEM/F12 (Invitrogen, Grand Island, N.Y.) liquid, 20% (v/v) KnockOut serum replacement (Invitrogen, Carlsbad, Calif.), 1 mM L-glutamine (Invitrogen), 0.1 mM nonessential amino acids (Invitrogen), 0.1 mM mercaptoethanol (Sigma-Aldrich, St. Louis, Mo.), 4 ng/mL human recombinant FGF2 (human recombinant basic fibroblast growth factor, Invitrogen)].

While the medium was replaced every day, the undifferentiated stem cells (FIG. 1A) were passaged at a ratio of 1:15 to 1:18 every six or seven days manually or with collagenase V (collagenase IV, Invitrogen), and then transferred onto fresh mouse embryonic fibroblast feeder cells. During the passage of the human embryonic stem cells, immunochemical staining with OCT-4 and SSEA-4 (Chemicon, Temecula, Calif.), which are antigens specific to undifferentiated human embryonic stem cells, was conducted at regular intervals of time to monitor the degree of differentiation. Cells that were found to have undergone differentiation were removed. Meanwhile, the presence of mycoplasma contamination in the embryonic stem cell line, which could have an undesirable effect on the differentiation of human embryonic stem cells, was regularly monitored using a MycoAlert mycoplasma detection kit (Lonza, Rockland, Me.).

<1-2> Generation and Culture of Human Induced Pluripotent Stem Cell (iPSC)

Human induced pluripotent stem cells were prepared by transfecting stem cell genes (SOX2, KLF4, OCT4, L-MYC, LIN28, and small hairpin RNA for p53) into BJ1 fibroblasts (neonatal foreskin fibroblast, ATCC) using episomal plasmid vectors (Okita, Nat method 2011; 8: 409). The human induced pluripotent stem cells were allowed to proliferate undifferentiated (passages 5 to 9) by culturing them over feeder cells, such as irradiated mouse embryonic fibroblasts (MEF, Global Stem, Gaithersburg, Md., USA) or mitomycin-treated mouse SNL cells (SNL 76/7 cell line, ECACC, Porton Down, UK) in the following medium: embryonic stem cell medium [DMEM/F12 (Invitrogen, Grand Island, N.Y., USA) liquid, 20% (v/v) KnockOut serum replacement (Invitrogen, Carlsbad, Calif., USA), 1 mM L-glutamine (Invitrogen), 0.1 mM nonessential amino acids (Invitrogen), 0.1 mM mercaptoethanol (Sigma-Aldrich, St. Louis, Mo.), and 4 ng/mL human recombinant FGF2 (Invitrogen)].

While the medium was replaced every day, the undifferentiated stem cells (FIG. 2A) were passaged at a ratio of 1:12 to 1:15 every six or seven days manually or with collagenase IV (Invitrogen), and then transferred onto fresh mouse embryonic fibroblast feeder cells. During the passage of the human induced pluripotent stem cells, immunochemical staining (FIGS. 2B and 2C) with alkaline phosphatase (Sigma-Aldrich), NANOG (Abcam, Cambridge, Mass.) and SSEA-4 (Chemicon, Temecula, Calif.), which are antigens specific to undifferentiated human induced pluripotent stem cells, was conducted at regular intervals of time to monitor the degree of differentiation. Cells that were identified to have undergone differentiation were removed. To evaluate pluripotency of the undifferentiated human induced pluripotent stem cells, a teratoma assay was performed. 10 weeks after transplantation of $1 \times 10^7$ of human induced pluripotent stem cells into the dorsal surface of an immunosuppressed model, rd/SCID mouse, teratomas thus formed were removed, followed by H&E staining (FIG. 2D).

The presence of mycoplasma contamination in the human induced pluripotent stem cells, which could have an undesirable effect on the differentiation of human induced pluripotent stem cells, was regularly monitored using a MycoAlert mycoplasma detection kit (Lonza, Rockland, Me.).

EXAMPLE 2

Differentiation from Human Embryonic Stem Cells or Human Induced Pluripotent Stem Cells into Eye Field Precursors First, human embryonic stem cells or human induced pluripotent stem cells cultured by the method of Example 1 were separated from the mouse embryonic fibroblasts and transferred onto 6-well ultra-low attachment plates (Corning Incorporated, Corning, N.Y., USA), respectively.

To the human embryonic stem cells or human induced pluripotent stem cells in the 6-well ultra-low attachment plates was added a medium for inducing differentiation into eye field precursors [DMEM/F12, 10% KnockOut serum replacement, 1 mM L-glutamine, 0.1 mM nonessential amino acids, 0.1 mM mercaptoethanol, 1% B27 supplement (Invitrogen), 1 ng/mL recombinant Noggin (R&D Systems), 1 ng/mL recombinant Dkk-1 (recombinant Dickkopf-1, R&D Systems), and 5 ng/mL recombinant IGF-1 (recombinant insulin-like growth factor-1, R&D Systems)]. While the medium was aspirated at 3 days and then replaced with a fresh medium, the cells were cultured for 4 days to 5 days to generate eye field precursors in the form of floating aggregates in the medium (FIGS. 1B, 3).

EXAMPLE 3

Differentiation from Eye Field Precursors into Retinal Progenitor Cells

Figure 3:
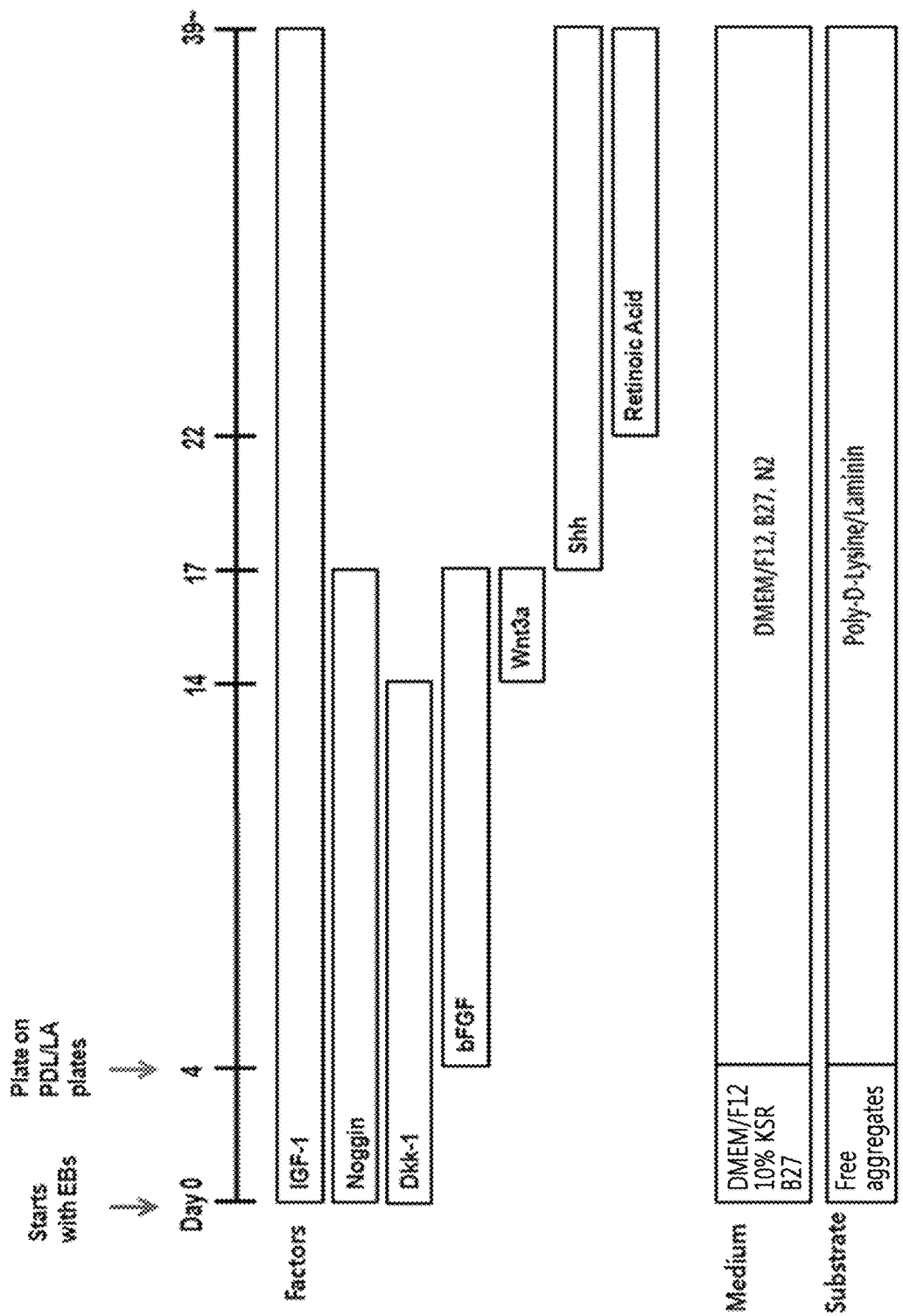
FIG. 3 is a schematic diagram showing the differentiation of retinal ganglion cells from human pluripotent stem cells according to the present invention. With reference to embryological development of retinal ganglion cells, chemically defined medium, adhesion of cells in vitro, and differentiation factors were considered at each stage. Stage and period of embryological development were planned based on those of mice.
Figure 4:
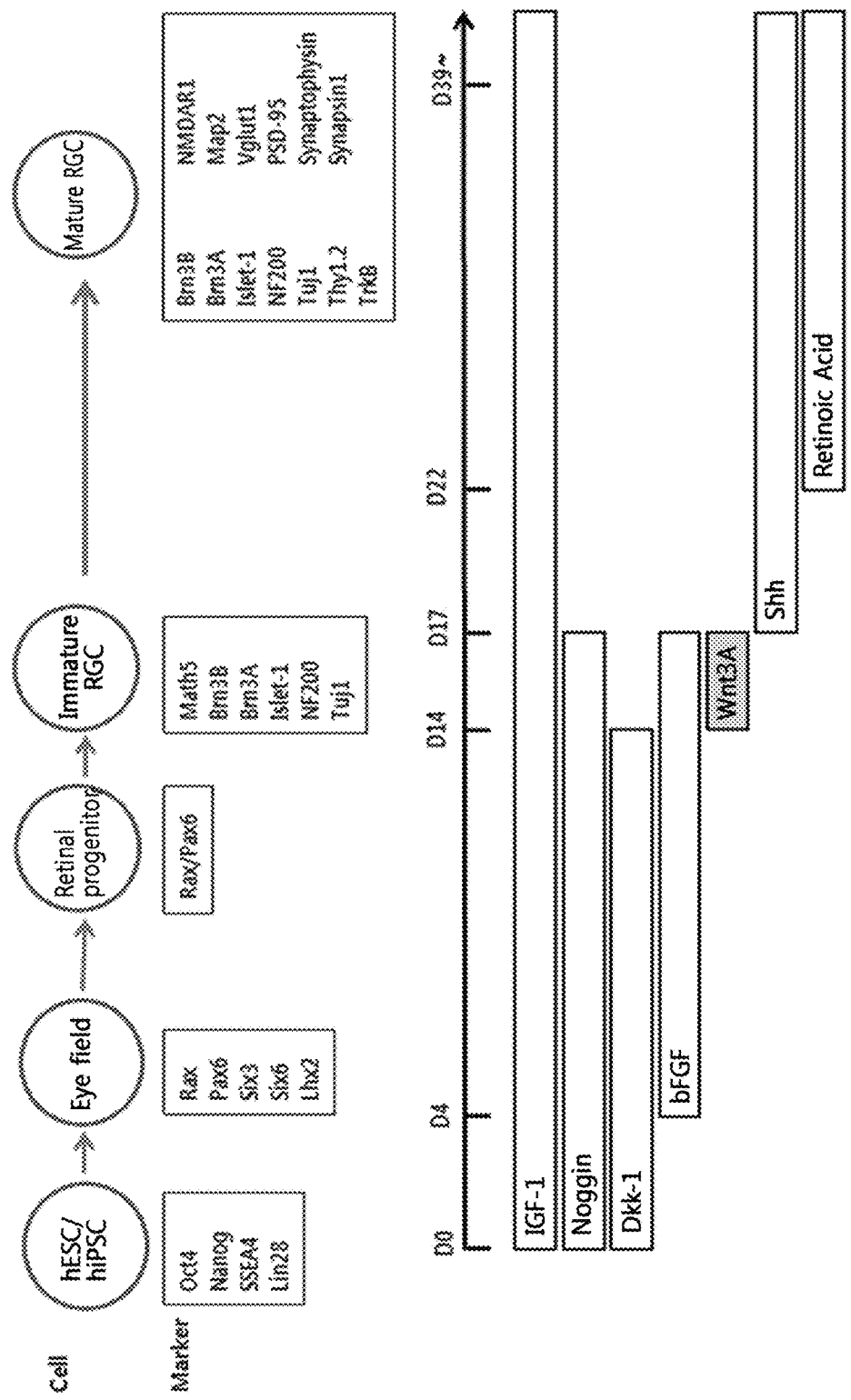
FIG. 4 is a schematic diagram showing the differentiation of retinal ganglion cells from human pluripotent stem cells according to the present invention, which was conducted according to a protocol of treating Wnt3a for 3 days from day 14 to day 17 after induction of the differentiation (referred to as Protocol A). This protocol is a prototype of the protocols of the present invention. The cell type and differentiation markers at respective differentiation stages are indicated, and photographs of the cells differentiated according to the protocol are given in FIG. 1A-1F.
Figure 5:
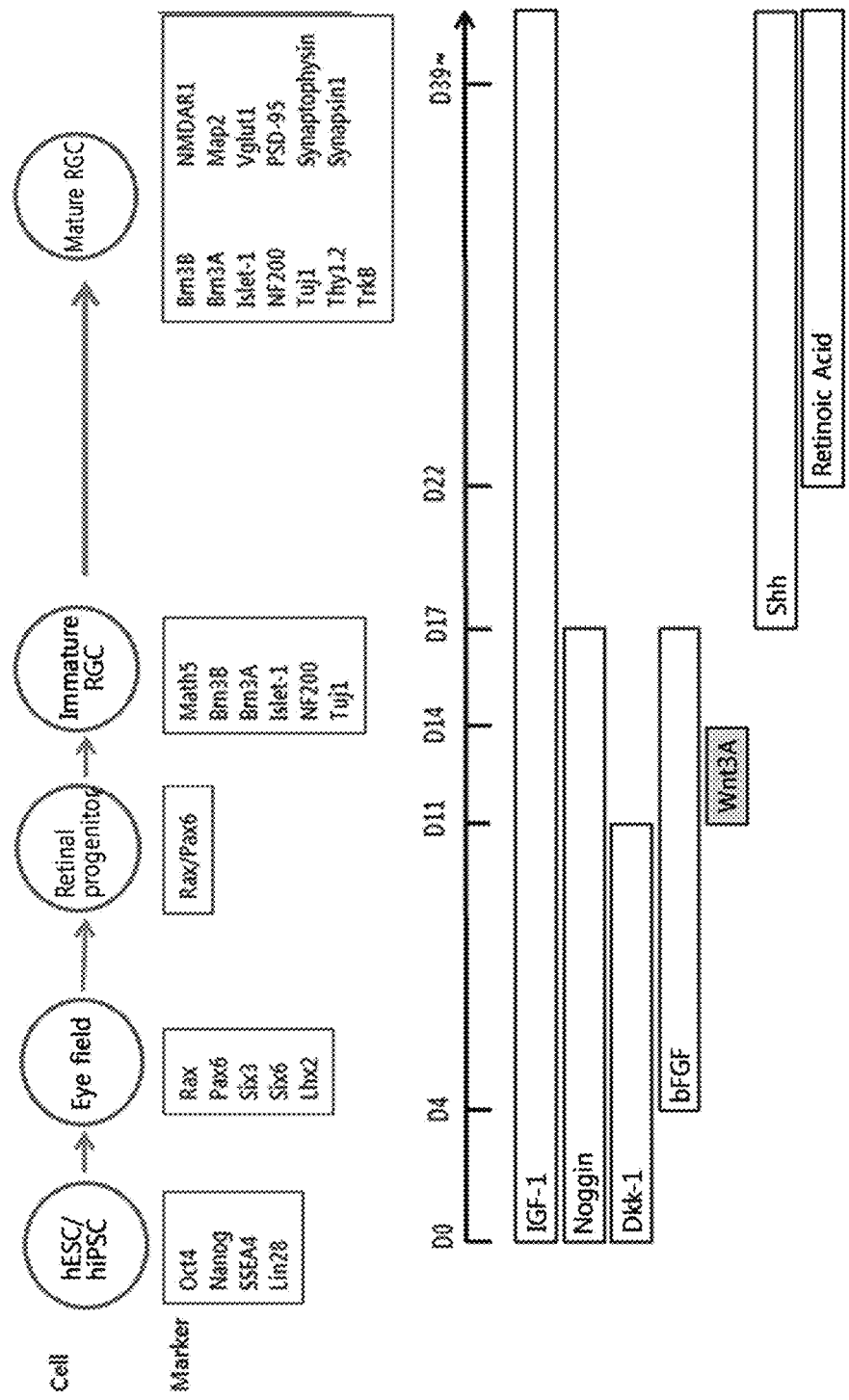
FIG. 5 is a schematic diagram showing the differentiation of retinal ganglion cells from human pluripotent stem cells according to the present invention, which was conducted according to a protocol of treating Wnt3a for 3 days from day 11 to day 14 after induction of the differentiation (referred to as Protocol B).

The eye field precursors (floating aggregates) generated in Example 2 were seeded at a density of 53±8 cells per well (292±53 cells/floating aggregate) into 6-well poly-D-lysine/laminin-coated plates (BD Biosciences), at a density of 30±5 cells per well on 12-well poly-D-lysine/laminin-coated plates, and at a density of 12±4 cells per well on 8-well poly-D-lysine/laminin-coated plates, and then cultured for 10 days to generate retinal progenitor cells (FIG. 1C), with the supply of a medium for inducing differentiation into retinal progenitor cells [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement, 1% N2 supplement (Invitrogen), 10 ng/mL Dkk-1, 10 ng/mL Noggin, 10 ng/mL IGF-1, and 5 ng/mL FGF2] (Protocol A) (FIGS. 3 and 4). Protocol B (FIG. 5) and C (FIG. 6) were performed by supplying the present medium for 7 days.

EXAMPLE 4

Differentiation from Retinal Progenitor Cells into Immature Retinal Ganglion Cells (RGCs)

Figure 6:
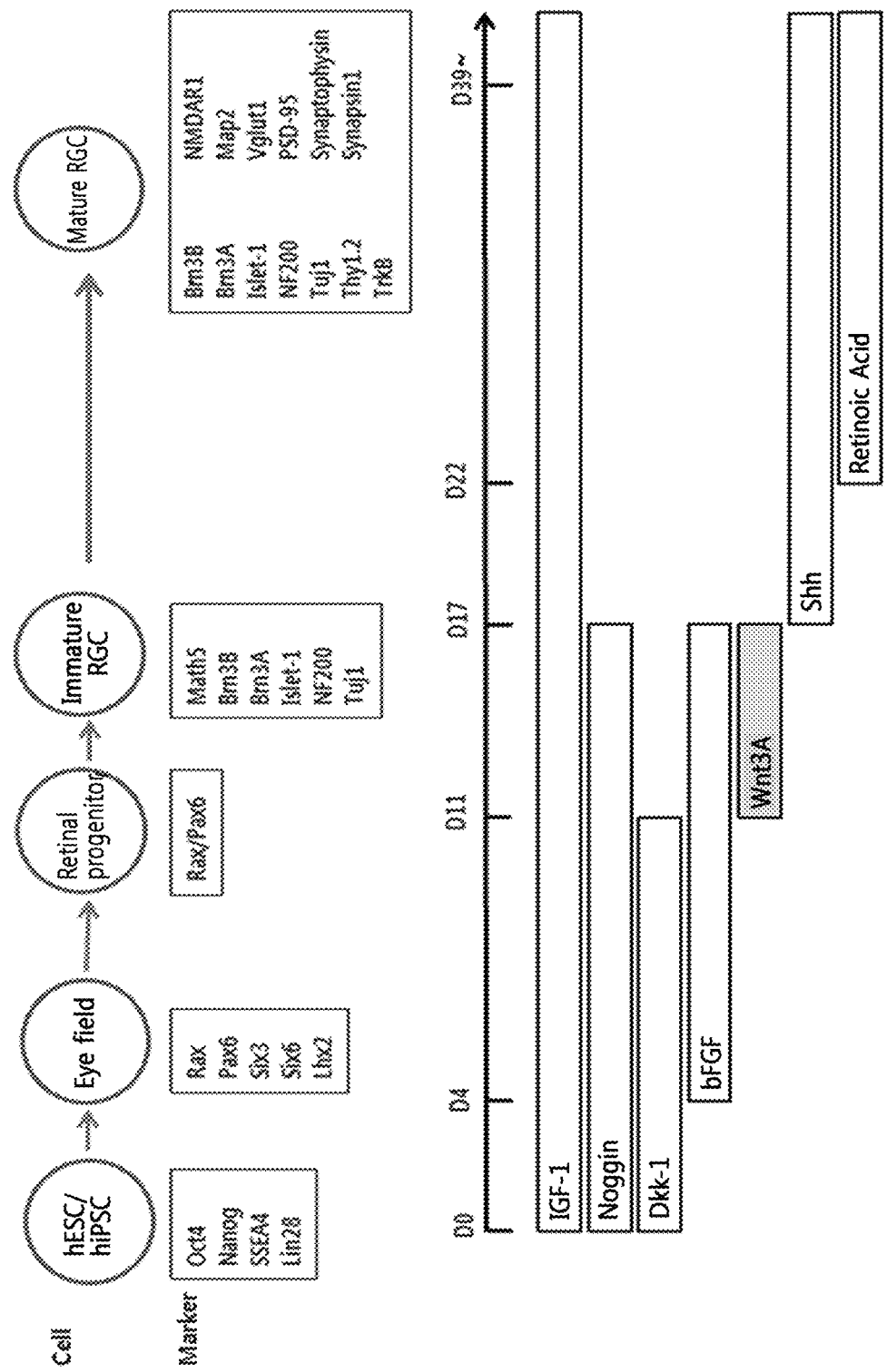
FIG. 6 is a schematic diagram showing the differentiation of retinal ganglion cells from human pluripotent stem cells according to the present invention, which was conducted according to a protocol of treating Wnt3a for 6 days from day 11 to day 17 after induction of the differentiation (referred to as Protocol C).

The retinal progenitor cells generated in Example 3 were cultured in a medium for inducing differentiation into immature retinal ganglion cells [DMEM/F12(Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/mL Noggin, 10 ng/mL IGF-1, 5 ng/mL FGF2, 50 ng/mL recombinant Wnt3a (recombinant Wnt3a, R&D Systems)] for 3 days, thus giving immature retinal ganglion cells (FIGS. 1D, 3 to 5). Protocol C was performed by supplying the present medium for 6 days (FIG. 6).

EXAMPLE 5

Differentiation from Immature Retinal Ganglion Cells into Mature Retinal Ganglion Cells: Step 1

The immature retinal ganglion cells generated in Example 4 were induced to differentiate into mature retinal ganglion cells by supplying a differentiation medium [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/mL IGF-1, 250 ng/mL recombinant Shh (recombinant Sonic Hedgehog amino terminal peptide, Shh, R&D Systems)] for 5 days (FIG. 1E, 3 to 6).

EXAMPLE 6

Differentiation from Immature Retinal Ganglion Cells into Mature Retinal Ganglion Cells: Step 2

The retinal ganglion cells generated in Example 5 were matured by supplying a differentiation medium [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/mL IGF-1, 250 ng/mL Shh, 500 nM all-trans retinoic acid (RA, Sigma-Aldrich)] for 17 days (FIG. 1E, 3 to 6). All the media of Examples 2 to 6 were replaced with fresh ones every two or three days, and the cells were cultured at 37° C. in a 5% $CO_2$ atmosphere (FIG. 1F, 3 to 6). The present medium for retinal ganglion cells was used to culture the cells until day 120 of differentiation.

EXAMPLE 7

Assay for Cellular Differentiation-Related Markers

<7-1> Immunochemical Staining and Identification of Cellular Differentiation-Related Marker Protein Expression The differentiation of the cells obtained in Examples 3 to 6 was examined using an immunochemical staining method as follows.

The eye field precursors (floating aggregates) were cultured in 8-well poly-D-lysine/laminin-coated slides (BD Biosciences, Bedford, Mass.) under the same conditions that were used for differentiation into the retinal progenitor cells, the immature retinal ganglion cells, and the mature retinal ganglion cells. The cells completely cultured in each step were fixed with 4% paraformaldehyde (Sigma-Aldrich), after which non-specific reactions were blocked with PBS containing 3% BSA (Jackson Immunoresearch Laboratory, Bar Harbor, Me., USA) and 0.25% Triton X-100 (Sigma-Aldrich).

After being blocked for 90 min, the slides in each differentiation step were incubated overnight at 4° C. with antibodies specific to cells of each differentiation step as given in Table 1. Before use, these antibodies were diluted in a PBS solution containing 1% BSA and 0.25% Triton X-100. The cells cultured on the slides in each step were washed three times for 5 min with PBS and incubated at room temperature for 2 hr with species-specific secondary antibody conjugated with Cy3 (1:800, Jackson Immunoresearch Laboratory) or Alexa488 (1:500, Invitrogen) (Table 1). A standard material suitable for the primary and the secondary antibodies was used to examine non-specific staining or interaction between the antibodies. Thereafter, the cells were washed three times for 5 min with PBS, counterstained with DAPI (4′,6-diamidino-2 phenylindole) and mounted in Vectashield (Vector Laboratories), followed by visualization under an epifluorescence microscope (Nikon Eclipse, E800, Tokyo, Japan) and a confocal microscope (Zeiss LSM510, Carl Zeiss, Inc, Thornwood, N.Y., USA). 500 cells were counted from 20 microscopic fields randomly selected at 400 magnification and evaluated for positive responses to each antibody. Positive responses to antibodies were determined after at least three evaluations.

<7-2> Flow Cytometry and Identification of Cellular Differentiation-Related Marker Protein Expression Cells were detached by 0.05% trypsin (Invitrogen) on days 17 and 39 after induction of differentiation. Cells were fixed with a Cytofix/Cytoperm buffer solution (Biosciences), and washed with a Perm/Wash buffer solution (BD Biosciences). Cells were reacted with primary antibody at 4° C. for 30 min, and secondary antibody at 4° C. for 20 min (Table 1). The reaction samples were analyzed by FACSCalibur (BD Biosciences) and FlowJo software (Treestar).

<7-3> Identification of Retinal Ganglion Cell-Specific Marker by Western Blotting The cultured cells were lysed on day 39 after induction of differentiation with a protein extraction buffer solution containing a protease inhibitor. Total protein concentration was measured using a Bradford protein assay kit. An equal amount of the protein was loaded on polyacrylamide gel (Any kD Mini-PROTEAN TGX precast polyacrylamide gels, Bio-Rad, Hercules, Calif.), and then transferred onto a polyvinylidene difluoride membrane (Milipore, Billerica, Mass.). This membrane was reacted with primary antibody (Table 1, Brn3B 1:1,000, Brn3A 1:1,000, Tuj1 1:1000, NF200 1:1,000, Actin 1:2,000) and secondary antibody (HRP-conjugated secondary antibody, Goat anti-mouse or anti-rabbit IgG, diluted 1:2,000, Santa Cruz, Calif.), and then the reacted proteins were detected using chemiluminescence detection kit (Amersham ECL, GE Healthcare Life technology, Piscataway, N.J.).

TABLE 1

Antibodies used in immunofluorescence assay

| Antibody | Species | Dilution for ICF* | Supplier | Catalogue No. |
|---|---|---|---|---|
| Brn3A | Rabbit | 1:500 | gift from Eric Turner | N/A |
| Brn3B | Rabbit | 1:500 | gift from Eric Turner | N/A |
| Islet-1 | Mouse | 1:10 | DSHB | 40.2D6 |
| KI67 | Mouse | 1:200 | Vector Laboratories | vp-k452 |
| Map2 | Mouse | 1:1,000 | Sigma-Aldrich | M1406 |
| Map2 | Rabbit | 1:500 | Milipore | AB5622 |
| Math5 | Rabbit | 1:500 | Abcam | ab78046 |
| Nanog | Rabbit | 1:500 | Abcam | ab80892 |
| Neurofilament-200 | Rabbit | 1:1,000 | Sigma-Aldrich | N4142 |
| NMDAR1 | Mouse | 1:250 | BD Biosciences | 556308 |
| Pax6 | Mouse | 1:1 | DSHB | PAX6 |
| PSD-95 | Mouse | 1:500 | NeuroMab | 75-028 |
| Rax | Rabbit | 1:250 | Abcam | ab23340 |
| SSEA4 | Mouse | 1:100 | Chemicon | MAB4304 |
| Synapsin1 | Rabbit | 1:500 | Stressgen | VAP-SV060E |
| Thy-1.2 | Mouse | 1:250 | eBioscience | 14-0903-81 |
| TrkB | Mouse | 1:100 | Santa Cruz | sc-136991 |
| β-tubulin (Tuj1) | Mouse | 1:1,000 | Covance | MMS-435P |
| Vgat | Rabbit | 1:1,000 | Synaptic Systems | 131 003 |
| Vglut1 | Rabbit | 1:1,000 | Synaptic Systems | 135 303 |
| Anti-mouse Alexa Fluor 488 | Goat | 1:500 | Molecular Probes | A11029 |
| Anti-rabbit Alexa Fluor 488 | Goat | 1:500 | Molecular Probes | A11034 |
| Anti-mouse Cy3 | Goat | 1:800 | Jackson Laboratory | 115-165-062 |
| Anti-rabbit Cy3 | Goat | 1:800 | Jackson Laboratory | 111-165-045 |
| Anti-mouse R-Phycoerythrin | Goat | 1:800 | Jackson Laboratory | 115-116-146 |
| Anti-rabbit R-Phycoerythrin | Goat | 1:800 | Jackson Laboratory | 115-116-144 |

*ICF: Immunocytofluorescence staining

As a result of identifying differentiation-related marker expression, flow cytometry results (Table 2A) of markers of cells obtained by Protocol A of Example 4 on day 17 after induction of differentiation showed that retinal progenitor cell markers, Rax- and Pax6-positive cells were 95.8±1.4% and 93.8±0.7%, respectively (FIG. 7A). Meanwhile, retinal ganglion cell-specific markers, Math5, Brn3B- and Brn3A-positive cells were 95.2±1.2%, 96.8±0.6%, and 97.5±0.9%, respectively. In mice, Math5, which is expressed at an early stage of retinal ganglion cells, is known to be detected from embryonic day (E) 11 to 1 day after birth, and Brn3B and Brn3A are known to be detected at a time of retinal ganglion cell generation during embryonic development and continue for their life. Further, these markers are co-expressed in most retinal ganglion cells. Islet-1, which is a marker of the subtype of retinal ganglion cells, was detected as 16.4±2.7%. On day 17 after induction of differentiation, the immunofluorescence staining results and positive rates are consistent with the results of flow cytometry. In nuclei of most cells, Math5 and Brn3B were strongly stained (FIGS. 7B and 7C). The cytoplasm of Brn3A (nuclear staining)-positive cells are positive to neuron-specific marker Tuj1 (98.2±0.4%) (Table 2A, FIG. 7D), indicating their differentiation into retinal ganglion cells, which are a type of neuron. About ⅕ of the cells positive to NF200 which is expressed in axons of retinal ganglion cells were positive to Islet-1, which is a marker of the subtype of retinal ganglion cells (Table 2A, FIG. 7E). ⅓ of the total retinal ganglion cells are reported to be Islet-1-positive retinal ganglion cells. Maturation characteristics of axonal and dendritic arbor, ring, and spiny process were not observed yet.

Flow cytometry results (Table 2B, FIG. 8) of markers of cells obtained by Protocol A of Example 6 on day 39 after induction of differentiation showed that Pax6-positive cells were 82.3±3.5%. Pax6 is known to be expressed in retinal progenitor cells and also to continue to be expressed after differentiation into retinal ganglion cells (FIG. 9A). Math5-, Brn3B (FIGS. 9B, 9F, 9G)-, and Brn3A (FIGS. 9C, 9D, 9H)-positive cells were 77.3±2.7%, 84.7±0.8%, 89.9±2.3%, respectively. It seems that Math5 was reduced with cell differentiation. Islet-1-positive cells were 16.4±2.7% on day 17 after induction of differentiation and increased to 32.8±7.1% on day 39 after induction of differentiation, indicating that ⅓ of the total retinal ganglion cells are Islet-1-positive (FIG. 9E). Meanwhile, cell proliferation marker KI67-positive cells were remarkably reduced from 81.0±3.5% to 18.4±3.5% on day 17 after induction of differentiation. The immunofluorescence staining results showed that axonal ring and spiny process, and dendritic arbor, ring, and spiny process were observed in retinal ganglion cells, indicating maturation (FIGS. 9F to 9I). This maturation further progressed on day 59 after induction of differentiation (FIG. 10).

Results of Western blot analysis also showed strong expressions of retinal ganglion cell-specific markers, Brn3B and Brn3A and neuron-specific markers, NF200 and Tuj1, as in the results of immunochemical staining and flow cytometry (FIG. 9J).

TABLE 2

Flow cytometry results of H9-derived RGC on days 17 and 39 after differentiation according to Protocol A

| | A) day 17 | | | B) day 39 | |
|---|---|---|---|---|---|
| Marker | Mean, %(n = 3) | SEM | Marker | Mean, %(n = 3) | SEM |
| Brn3A | 97.5 | 0.9 | Brn3A | 89.9 | 2.3 |
| Brn3B | 96.8 | 0.6 | Brn3B | 84.7 | 0.8 |
| Islet-1 | 16.4 | 2.7 | Islet-1 | 32.8 | 7.1 |
| KI67 | 81.0 | 3.5 | KI67 | 18.4 | 3.5 |
| Math5 | 95.2 | 1.2 | Math5 | 77.3 | 2.7 |
| NF200 | 98.3 | 0.4 | NF200 | 96.5 | 0.9 |
| Pax6 | 93.8 | 0.7 | Pax6 | 82.3 | 3.5 |
| Tuj1 | 98.2 | 0.4 | Tuj1 | 94.7 | 2.5 |
| Rax | 95.8 | 1.4 | | | |

On day 39 after induction of differentiation into retinal ganglion cells according to Protocol B (FIG. 5) and Protocol C (FIG. 6) of Examples 5 and 6, marker protein expressions were identified. The results of flow cytometry of cell markers (Tables 3A and 3B) showed that cells positive to retinal ganglion cell-specific markers, Math5, Brn3B and Brn3A and neuronal axon and dendrite markers, Tuj1 and NF200 were similar to those of the prototype Protocol A, but the subtype marker Islet-1-positive cells were reduced to 12.4±2.5% and 7.8±1.6% in Protocols B and C. On the other hand, cytomorphology was examined by immunofluorescence staining. As a result, cells differentiated according to Protocol B showed positive rates of axons and dendrites and maturity being similar to those of the cells according to Protocol A, but low positive rates of presynaptic and postsynaptic vesicles having electrical functions, compared to Protocol A (FIG. 11). Cells differentiated according to Protocol C showed active generation of presynaptic and postsynaptic vesicles, but relatively low maturity of axon and dendrites (FIG. 12).

TABLE 3

Flow cytometry results of H9-derived RGC on day 39 after differentiation according to Protocols B and C

| | A) Protocol B | | | B) Protocol C | |
|---|---|---|---|---|---|
| Marker | Mean, %(n = 3) | SEM | Marker | Mean, %(n = 3) | SEM |
| Brn3A | 89.8 | 5.0 | Brn3A | 91.6 | 1.0 |
| Brn3B | 83.3 | 1.5 | Brn3B | 86.0 | 2.4 |
| Islet-1 | 12.4 | 2.5 | Islet-1 | 7.8 | 1.6 |
| KI67 | 15.0 | 1.0 | KI67 | 15.9 | 4.7 |
| Math5 | 93.6 | 1.1 | Math5 | 91.0 | 1.9 |
| NF200 | 89.6 | 3.8 | NF200 | 94.1 | 1.7 |
| Pax6 | 80.1 | 4.7 | Pax6 | 75.7 | 3.9 |
| Tuj1 | 94.1 | 1.8 | Tuj1 | 95.6 | 0.5 |

Human embryonic stem cell line H7, other than H9, and human induced pluripotent stem cells were differentiated into retinal ganglion cells according to Protocol A of Example 6. On day 39 after induction of differentiation, immunofluorescence staining of the cell markers and flow cytometry were performed. As a result, percentages of Math5-, Brn3B- and Brn3A-positive human embryonic stem cell H7 were 95.0%, 90.2% and 94.4%, respectively, which are the same as in H9 cell line (Table 4A). Immunofluorescence staining results showed mature features of axons and dendrites and active generation of presynaptic and postsynaptic vesicles having electrical functions (FIG. 13).

Percentages of Math5-, Brn3B- and Brn3A-positive human induced pluripotent stem cell were 73.0%, 61.4% and 77.0%, respectively, which are relatively lower than in H9 cell line (Table 4B). Immunofluorescence staining results showed mature features of axons and dendrites and active generation of presynaptic and postsynaptic vesicles having electrical functions (FIG. 14).

TABLE 4

Flow cytometry results of H7 and iPSC-derived RGC on day 39 after differentiation according to Protocol A

| A) H7-derived RGCs | | B) iPSC-derived RGCs | |
|---|---|---|---|
| Marker | Mean, %(n = 2) | Marker | Mean, %(n = 2) |
| Brn3A | 94.4 | Brn3A | 77.0 |
| Brn3B | 90.2 | Brn3B | 61.4 |
| Islet-1 | 17.8 | Islet-1 | 12.0 |
| KI67 | 29.1 | KI67 | 25.4 |
| Math5 | 95.0 | Math5 | 73.0 |
| NF200 | 95.5 | NF200 | 87.5 |
| Pax6 | 87.8 | Pax6 | 56.2 |
| Tuj1 | 90.5 | Tuj1 | 89.0 |

EXAMPLE 8

Test of Electrophysiological Properties and Functions of Retinal Ganglion Cells Differentiated from Human Pluripotent Stem Cells Whole-cell voltage recordings and current-clamp recordings were performed at 32±1° C. by infusing a recording chamber with artificial cerebrospinal fluid at a rate of 1 mL/min to 1.5 mL/min. The artificial cerebrospinal fluid was composed of 125 mM NaCl, 25 mM NaHCO$_3$, 2.5 mM KCl, 1.25 mM NaH$_2$PO$_4$, 2 mM CaCl$_2$, 1 mM MgCl$_2$, 20 mM glucose, 1.2 mM pyruvate and 0.4 mM Na-ascorbate, and saturated at pH 7.4 with 95% O$_2$ and 5% CO$_2$. A patch pipette having a tip resistance of 3.5 MΩ to 4.5 MΩ was used. A series resistance after whole-cell configuration was between 10 MΩ and 15 MΩ. Recordings were performed using an EPC-10 amplifier (HEKA, Lambrecht-Pfalz, Germany), and upon recording, a pipette solution containing 143 mM K-gluconate, 7 mM KCl, 15 mM HEPES, 4 mM MgATP, 0.3 mM NaGTP, 4 mM Na-ascorbate and 0.1 mM EGTA was used, and pH was adjusted to 7.3 using KOH. Spontaneous excitatory postsynaptic currents (sEPSCs) were recorded at a holding potential of −70 mV. To identify the patterns of spontaneous postsynaptic current, 6-cyano-7-nitroquinoxaline-2,3-dione (CNQX, 50 µM), D-(−)-2-amino-5-phosphonopentanoic acid (AP5, 50 µM) and (+)-bicuculline (50 µM) were injected to a bath solution of the experimental chamber (Sigma-Aldrich). CNQX blocks AMPA receptor, AP5 blocks NMDA receptor, and bicuculline blocks GABA receptor. Na$^+$ currents were blocked by tetrodotoxin (TTX, 1 µM), and K$^+$ currents were blocked by 4-aminopyridine (4-AP, 1 mM) (Sigma-Aldrich).

<8-1> Test of Electrophysiological Properties of Retinal Ganglion Cells Differentiated from Human Pluripotent Stem Cells To test electrical properties of the human pluripotent stem cell-derived retinal ganglion cells differentiated according to the present invention, retinal ganglion cells differentiated according to Protocol A was first evaluated. In the evaluation of action potentials on day 39 after induction of differentiation, a robust regular-spiking train of action potentials was observed in response to step current injection (FIG. 15A). The results of whole-cell patch clamp recording showed the presence of voltage-gated sodium channel, which was blocked by tetrodotoxin (FIG. 15B). Therefore, it was confirmed that human pluripotent stem cell-derived retinal ganglion cells were differentiated into electrically excitable cells. In the evaluation of action potentials on day 59 after induction of differentiation, action potentials were found to be more mature in response to step current injection than those on day 39 after induction of differentiation (FIG. 16B). It was reported that during embryological development, neurons develop into mature firing cells over days. An identical process is found in vivo (Connors et al. 1982; McCormick & Prince, 1987). Similar results are also observed in retinal ganglion cells differentiated according to Protocols B (FIG. 17A) and C (FIG. 18A) and human induced pluripotent stem cells (FIG. 20). The retinal ganglion cells differentiated according to the protocol of the present invention showed increased electrical maturation and function over time.

<8-2> Test of Electrophysiological Functions of Retinal Ganglion Cells Differentiated from Human Pluripotent Stem Cells Retinal ganglion cells differentiated from human pluripotent stem cells according to the present invention form functional excitatory synapses. Synaptogenesis is a critical step in the development of neural networks. The formation of physical synapses among human pluripotent stem cell-derived retinal ganglion cells was detected using super-resolution microscopy to visualize presynaptic and postsynaptic protein localization. Synapses were defined as regions of hundreds of nanometers in diameter found near dendrites detected by MAP2 staining where proteins specific to the pre- and postsynaptic compartments were juxtaposed. Antibodies against presynaptic and postsynaptic proteins were used to identify synapses: Antibodies against the excitatory glutamatergic postsynaptic protein, PSD-95 (glutamatergic postsynaptic density 95) and the presynaptic protein, synapsin1 were used. Foci of PSD-95 generated from pluripotent stem cell-derived retinal ganglion cells were abundant along dendrites or in the 100 nm size range thereof, and juxtaposed, but non-overlapping, with presynaptic vesicle, synapsin1 (FIGS. 10G and 10H). These are also found in retinal ganglion cells derived from another human embryonic stem cell line H7 (FIGS. 13G and 13H) and human induced pluripotent stem cells (FIGS. 14K and 14L), indicating formation of physical synapses among human pluripotent stem cell-derived retinal ganglion cells.

Meanwhile, physical synapses formed among the cells were electrophysiologically evaluated. Spontaneous excitatory postsynaptic currents (sEPSCs) were detected without co-culture with other retinal tissues on day 39 after induction of differentiation from human embryonic stem cell-derived retinal ganglion cells (FIG. 15C), indicating formation of functional excitatory synapses among human embryonic stem cell-derived retinal ganglion cells. Further, frequency of sEPSCs and depth of spiking were increased when evaluated on day 59 after induction of differentiation (FIG. 16E), implying that neuronal maturation progressed over time. The sEPSCs were found to be blocked by CNQX, suggesting that they are one of AMPA-mediated excitatory glutamatergic neurons. Similar results are also observed in the retinal ganglion cells differentiated according to Protocols B (FIG. 17B) and C (FIG. 18B).

EXAMPLE 9

Comparison Between Protocols for Differentiation from Human Embryonic Stem Cells or Human Induced Pluripotent Stem Cells into Retinal Photoreceptor Cells and Retinal Ganglion Cells The present inventors disclosed a method of differentiating retinal cells from stem cells in the previous patents (Korean Patent NO. 10-1268741 (2013 May 22) and WO2011/043591 (2011 Apr. 14)).

According to the methods disclosed in the above documents, differentiation of photoreceptor cells from retinal progenitor cells was maximized to about 80%. However, their differentiation into retinal ganglion cells was partially progressed to only about 6%.

<9-1> Differentiation from Human Embryonic Stem Cells or Human Induced Pluripotent Stem Cells into Retinal Photoreceptor Cells Differentiation from human embryonic stem cells or human induced pluripotent stem cells into eye field precursors and retinal progenitor cells was performed in the same manner as in Examples 1 to 3.

On day 13 after induction of differentiation, retinal progenitor cells generated in Example 3 were differentiated into photoreceptor cell precursors by supplying a differentiation medium for photoreceptor cell precursors [DMEM/F12(Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/mL Noggin, 10 ng/mL IGF-1, 5 ng/mL FGF2, 50 ng/mL recombinant Wnt3a (recombinant Wnt3a, R&D Systems)] for 5 days. On day 18 after induction of differentiation, 250 ng/mL recombinant Shh (recombinant Sonic Hedgehog amino terminal peptide, Shh, R&D Systems) was added to the differentiation medium for photoreceptor cell precursors and the cells were differentiated for 5 days into photoreceptor cells. On day 21 after induction of differentiation, 500 nM retinoic acid (RA) was added to the medium for photoreceptor cells, and cultured for 29 days to mature the generated photoreceptor cells. In the case where culture of the photoreceptor cells was to continue after 29 days, the medium containing Wnt3a, Shh and RA was continuously supplied. In the immunofluorescence results of the cells generated by this method, photoreceptor cells were 80% or more and retinal ganglion cells were about 6%.

<9-2> Differentiation from Human Embryonic Stem Cells or Human Induced Pluripotent Stem Cells into Retinal Ganglion Cells Differentiation from human embryonic stem cells or human induced pluripotent stem cells into retinal ganglion cells was performed in the same manner as in differentiation into eye field precursors, and differentiation into retinal progenitor cells was performed in the same manner as in differentiation into photoreceptor cells, except that 50 ng/mL recombinant Wnt3a was supplied from day 14 after induction of differentiation for 3 days, and then removed. Shh and RA were supplied after removal of Wnt3a. That is, after initiation of differentiation into retinal ganglion cells, when retinal ganglion cells are differentiated and matured, a medium from which Wnt3a is removed and to which Shh and RA are added at each stage is needed.

In the immunofluorescence results of the cells generated by this method, photoreceptor cell-related markers, Crx and Ret-P1, were not observed.

EXAMPLE 10

Differentiation from Immature Retinal Ganglion Cells into Mature Retinal Ganglion Cells: Step 2

The mature retinal ganglion cells obtained in Example 6 can be matured using the differentiation method of Example 6, but they can be also matured using a medium prepared by removing IGF-1, Shh, and retinoic acid form the above differentiation medium on day 39 after induction of the differentiation. Electrophysiological analysis was performed on day 96 after induction of the differentiation to evaluate maturity (FIG. 19). In addition, retinal ganglion cells were matured on day 32 after induction of the differentiation in the same manner, and as a result, they showed similar maturity to those cultured in a medium containing all of IGF-1, Shh and retinoic acid.

EXAMPLE 11

Differentiation of Human Embryonic Stem Cell-Derived Retinal Ganglion Cells by Wnt Signaling Pathway Activator and Shh Receptor Activator Differentiation from human embryonic stem cells or human induced pluripotent stem cells into eye field precursors or retinal progenitor cells was performed in the same manner as in Examples 1 to 3.

On day 14 after induction of differentiation, retinal progenitor cells generated in Example 3 were cultured and differentiated into immature retinal ganglion cells for 3 days in a differentiation medium [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/mL Noggin, 10 ng/mL IGF-1, 5 ng/mL FGF2, 50 ng/mL recombinant Wnt3a (R&D Systems)] containing 2 µM BIO (6-bromoindirubin-3'-oxime) or 50 ng/mL Norrin as the Wnt signaling pathway activator instead of 50 ng/mL recombinant Wnt3a. On day 17 after induction of differentiation, immature retinal ganglion cells thus generated were cultured and differentiated into mature retinal ganglion cells for 5 days in a differentiation medium [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/mL IGF-1, 250 ng/mL recombinant Shh (R&D Systems)] containing 1 µM purmorphamine as the Shh receptor activator instead of 250 ng/mL Shh. On day 22 after induction of differentiation, the mature retinal ganglion cells were matured for 39 days using a medium prepared by adding 500 nM retinoic acid (RA) to the above differentiation medium.

The immunofluorescence assay of the cells generated by this method was performed using retinal ganglion cell markers, Islet-1 and NF200, and the results were consistent with the results of using Wnt3a and Shh (FIG. 21).

EXAMPLE 12

Effects of Wnt3a, Shh, and RA Used in Protocol a Differentiation Method

To examine effects of each of Wnt3a, Shh and RA used in the Protocol A differentiation method during production of retinal ganglion cells, respective factors were treated according to a differentiation schedule of Protocol A, and on day 39 after induction of differentiation, an immunofluorescence assay was performed using retinal ganglion cell-specific markers (FIG. 22).

1 µg/mL of a Wnt3a antagonist, Dkk1 was treated instead of Wnt3a on days 14 to 17 after induction of differentiation, and Shh and RA were treated according to the differentiation schedule, followed by immunofluorescence assay. As a result, retinal ganglion cells were hardly produced, because no Wnt3a was added and intrinsic Wnt3a of retinal progenitor cells was inhibited by Dkk1 (all marker-positive rates: less than 2%) (FIG. 22 (A)).

When Shh and RA were treated according to the respective differentiation schedules without treatment of Wnt3a, a small number of retinal ganglion cells was produced by the effect of intrinsic Wnt3a of retinal progenitor cells (all marker-positive rates: about 10% to 15%) (FIG. 22 (B)).

When Wnt3a was only treated without treatment of Shh and RA, 80% or more of retinal ganglion cells were produced due to the effect of Wnt3a. However, caliber growth and fasciculation of axons of retinal ganglion cells were delayed due to absence of shh (see NF200 staining). Further, no synaptogenesis and dendritic spine development of retinal ganglion cells were observed due to absence of RA (see TUJ1 staining) (FIG. 22 (C)).

When Wnt3a and Shh were treated without treatment of RA, 80% or more of retinal ganglion cells were produced due to the effect of Wnt3a, and the effect of Shh was also observed. However, synaptogenesis and dendritic spine development of retinal ganglion cells were inhibited due to absence of RA (see TUJ1 staining) (FIG. 22 (D)).

When Wnt3a and RA were treated without treatment of Shh, 80% or more of retinal ganglion cells were produced due to the effect of Wnt3a, but caliber growth and fasciculation of NF200-positive axons were delayed due to absence of shh (see NF200 staining).

These results suggest that treatment of Wnt3a plays a critical role in differentiation of retinal ganglion cells. It was also confirmed that retinal ganglion cells can be well-differentiated when RA and Shh are properly treated according to the schedule.

EXAMPLE 13

Cell Line of Human Pluripotent Stem Cell-Derived Retinal Ganglion Cells

Differentiation from stem cells into mature cells of organs requires a long period of time, and relies on an expert's time and efforts, and many reagents are needed. If cells at a final or intermediate stage of differentiation are established as cell lines, such differentiation time can be greatly reduced. That is, if mature cells are needed, differentiation is induced not from stem cells but from established cell lines, thereby preparing mature cells for a short period of time. With respect to this purpose, the present inventors have attempted to establish cell lines from mature cells at a final stage of differentiation, and finally they succeeded. Differentiation of stem cells progresses with asymmetric division. That is, two daughter cells generated after cell division have different cellular fates: one copy of the original stem cell as well as a second daughter programmed to differentiate into a non-stem cell fate. The present invention is characterized in that secondary culture of differentiated mature cells is performed to make mature differentiated cells die due to environmental change and to proliferate cells having stem cell features, leading to establishment of a cell line. In particular, it is an important point to establish an intermediate-stage cell line having both features of the original differentiated cells and stem cells.

Cells were detached by 0.05% trypsin (Invitrogen) on day 32 or 39 after induction of differentiation. The obtained cells were seeded on a culture flask, dish, or plate containing one of the following media at a density of $1.5 \times 10^4$ to $1.6 \times 10^4$/ $cm^2$. The following two media (Medium 1 and Medium 2) were the same as each other in terms of cell proliferation capacity, number and period of passage. Cells were cultured at 5% carbon dioxide ($CO_2$) and 37° C. while the following media were replaced every 2 days to 3 days. The proliferated cells were passaged at a ratio of 1:6 to 1:10 every 3 days to 4 days with 0.05% trypsin treatment.

Medium 1: [IMDM (Invitrogen), 15% FBS, 1 mM L-glutamine (Invitrogen), 0.1 mM mercaptoethanol (Sigma-Aldrich), 1% Insulin/Transferrin/Selenium-X (Invitrogen)].

Medium 2: [IMDM (Invitrogen), 15% FBS, 1 mM L-glutamine (Invitrogen), 0.1 mM mercaptoethanol (Sigma-Aldrich), 5 ng/mL FGF2, 10 ng/mL IGF-1, 5 ng/mL human recombinant EGF (human recombinant epidermal growth factor Peprotech, Rocky Hill, N.J.)].

Cells were cultured to passage number 20 (p20), and all cells passaged in Medium 1 and Medium 2 showed neuronal morphology in vitro (FIG. 23). Human pluripotent stem cell-derived retinal ganglion cell lines at passage number 15 to 17 (p15 to p17) were used to evaluate their cellular characteristics and neuronal functions. Immunofluorescence assay using antibodies against retinal ganglion cell-specific markers was performed by the method of Example 7, and neuronal functions were evaluated by Live Cell $Ca^{2+}$ imaging.

For calcium imaging, cells cultured on 18 mm coverslip were washed with Tyrode's solution (119 mM NaCl, 2.5 mM KCl, 2 mM $CaCl_2$, 2 mM $MgCl_2$, 25 mM HEPES, 30 mM glucose, pH 7.4) twice or three times, and then cultured at 37° C. with addition of 1 µM Fluo-4-AM (Life technologies, Carlsbad, Calif., USA). After culturing for 15 min, cells were washed with Tyrode's solution for 10 min. Time differential images were obtained by using an Olympus IX-71 inverted microscope (Olympus, Tokyo, Japan) equipped with 40×(1.0 NA) oil lens and EMCCD (iXon887, Andor Technologies, Belfast, Northern Ireland) every 0.5 sec for 30 min. From the $10^{th}$ image frame, cells were stimulated with 1 mM glutamate. After stimulation, cells were infused with Tyrode's solution.

The results of immunofluorescence assay showed that ganglion cell-specific markers Math5 (98.9%), Brn3B (52.4%), and Brn3A (99.7%) were expressed, and functional markers Thy1.2 (86.1%), TrkB (44.0%), and NMDAR-1 (97.0%) were also expressed. A neuronal marker Tuj1 (100%), and a retinal ganglion cell axon marker NF200 (98.5%) were also strongly expressed. Meanwhile, a cell proliferation marker KI67 (49.2%) was also observed, indicating that the cell line has cell proliferation capacity (FIG. 24).

Neuronal functions of the retinal ganglion cell line were tested by intracellular calcium images. The passaged cells were treated with 1 µM fluor-4 and stimulated with 1 mM glutamate. As a result, the majority of live cells showed a considerable increase in cytoplasmic calcium levels in response to glutamate stimulation, indicating that the retinal ganglion cell line has neuronal functions (FIG. 25).

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A method of preparing mature retinal ganglion cells by differentiation of retinal progenitor cells into mature retinal ganglion cells, comprising:
   (a) culturing the retinal progenitor cells in a first medium comprising an IGF1R (insulin-like growth factor-1receptor) activator and a Wnt signaling pathway activator to differentiate the retinal progenitor cells into immature retinal ganglion cells; and
   (b)(i) removing the Wnt signaling pathway activator from the first medium to generate a second medium lacking the Wnt signaling pathway activator, and further culturing the differentiated immature retinal ganglion cells of step (a) in the second medium lacking the Wnt signaling pathway activator, wherein the further culturing induces differentiation of the immature retinal ganglion cells into mature retinal ganglion cells, or
   (b)(ii) removing the differentiated immature retinal ganglion cells of step (a) to a second medium whose composition does not comprise Wnt signaling pathway activator, and culturing the differentiated immature retinal ganglion cells in the second medium, wherein the culturing induces differentiation of the immature retinal ganglion cells into mature retinal ganglion cells, wherein the differentiated mature retinal ganglion cells of (b)(i) or (b)(ii) express one or more genes selected from the group consisting of Thy1.2, TrkB, NMDAR1, Map2, Vglut1, PSD-95, Synaptophysin, and Synapsin1.

2. The method of claim 1, wherein the first medium further comprises:
   a BMP (bone morphogenetic protein) signaling pathway inhibitor, or an FGF (fibroblast growth factor) signaling pathway activator; or
   a BMP (bone morphogenetic protein) signaling pathway inhibitor and an FGF (fibroblast growth factor) signaling pathway activator.

3. The method of claim 2, wherein the second medium of (b)(i) or (b)(ii) does not comprise a BMP signaling pathway inhibitor and a FGF signaling pathway activator; and does comprise a Shh (sonic hedgehog) signaling pathway activator.

4. The method of claim 3, further comprising:
   (c)(i) culturing the mature retinal ganglion cells in a third medium comprising RA (retinoic acid); or
   (c)(ii) adding a retinoic acid (RA) to the second medium of (b)(i) or (b)(ii) to generate a third medium and culturing the mature retinal ganglion cells in the third medium.

5. The method of claim 4, further comprising:
   (d) removing the IGF1R activator, the Shh signaling pathway activator or the retinoic acid (RA) from the third medium and culturing the mature retinal ganglion cells.

6. The method of claim 1, wherein the retinal progenitor cells of (a) are obtained by a method comprising:
   (1) culturing stem cells in a medium comprising an IGF1R activator, a Wnt signaling pathway inhibitor, and a BMP signaling pathway inhibitor to differentiate the stem cells into eye field precursors in the form of floating aggregates; and
   (2) culturing the eye field precursors of (1) in a medium whose composition comprises an FGF signaling pathway activator to differentiate the eye field precursors in the form of floating aggregates into retinal progenitor cells.

7. The method of claim 6, wherein (1) is performed for about 1 day to 30 days, and (2) is performed for about 5 days to 15 days.

8. The method of claim 6, wherein the stem cells are selected from the group consisting of bone marrow stem cells (BMS), cord blood stem cells, amniotic fluid stem cells, fat stem cells, retinal stem cells (RSCs), intraretinal Muller glial cells, embryonic stem cells (ESCs), induced pluripotent stem cells (iPSCs), and somatic cell nuclear transfer cells (SCNTCs).

9. The method of claim 1, wherein (a) is performed for about 1 day to 10 days, and (b)(i) or (b)(ii) is performed for about 1 day to 120 days.

10. The method of claim 1, wherein the IGF1R activator is IGF-1 or IGF-2.

11. The method of claim 1, wherein a concentration of IGF1R activator in the first medium and the second medium of (b)(i) or (b)(ii) is about 0.01 ng/mL to about 100 ng/mL.

12. The method of claim 1, wherein the Wnt signaling pathway activator is one or more selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16b, substance increasing p3-catenin levels; lithium, LiCl, bivalent zinc, BIO (6-bromoindirubin-3'-oxime), SB216763, SB415286, CHIR99021, QS11 hydrate, TWS119, Kenpaullone, alsterpaullone, indirubin-3'-oxime, TDZD-8 and Ro 318220 methanesulfonate salt; Axin inhibitors; APC (adenomatous polyposis coli) inhibitors; norrin and R-spondin 2.

13. The method of claim 1, wherein the Wnt signaling pathway activator is Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, or Wnt16b, and is present in the first medium at a concentration of about 0.01ng/mL to about 500ng/mL; the Wnt signaling pathway activator is LiCl and is present in the first medium at a concentration of about 0.1mM to 50mM; the Wnt signaling pathway activator is BIO (6-bromoindirubin-3'-oxime),and is present in the first medium at a concentration of about 0.1µM to 50µM; or the Wnt signaling pathway activator is SB415286 , and is present in the first medium at a concentration of about 0.1µM to 500µM.

14. The method of claim 2, wherein the BMP signaling pathway inhibitor is one or more selected from the group consisting of Noggin, chordin, twisted gastrulation (Tsg), cerberus, coco, gremlin, PRDC (protein related to DAN and Cerberus), DAN (differential screening-selected gene aberrative in neuroblastoma), dante, follistatin, USAG-1(uterine sensitization-associated gene 1), dorsomorphin and sclerostin.

15. The method of claim 2, wherein a concentration of BMP signaling pathway inhibitor in the first medium is about 0.01ng/mL to about 10ng/mL.

16. The method of claim 2, wherein the FGF signaling pathway activator is one or more selected from the group consisting of FGF1, FGF2, FGF4, FGF8, FGF9, FGF17 and FGF19.

17. The method of claim 2, wherein a concentration of FGF signaling pathway activator in the first medium is about 0.01ng/mL to about 100ng/mL.

18. The method of claim 3, wherein the Shh signaling pathway activator is one or more selected from the group consisting of Shh, Smo (smoothened) receptor activators, inhibitors of Smo inhibition by Ptc (Patched), substances increasing Ci/Gli family levels, inhibitors of the intracellular degradation of Ci/Gli proteins, and Shh receptor activator Hg-Ag and purmorphamine.

19. The method of claim 3, wherein a concentration of the Shh signaling pathway activator in the second medium is about 0.1ng/mL to about 5000ng/mL.

20. The method of claim 4, wherein a concentration of RA in the third medium of (c)(i) or (c)(ii) is about 0.5nM to about 10,000nM.

21. The method of claim 6, wherein the Wnt signaling pathway inhibitor is one or more selected from the group consisting of Dkk-1, Dkk-2, Dkk-3 and Dkk-4.

22. The method of claim 6, wherein a concentration of the Wnt signaling pathway inhibitor in the medium of (1) is about 0.01ng/mL to about 10,000ng/mL.

23. The method of claim 1, further comprising the step of determining whether the retinal progenitor cells are differentiated into the mature retinal ganglion cells.

24. The method of claim 23, wherein the step of determining whether the retinal progenitor cells are differentiated into the mature retinal ganglion cells is performed by measuring mRNA or protein expression levels of one or more genes selected from the group consisting of Thy1.2, TrkB, NMDAR1, Map2, Vglut1, PSD-95, Synaptophysin, and Synapsin1.

25. The method of claim 6, wherein the eye field precursors in the form of floating aggregates are cultured in (2) by adhering to a plate coated with an extracellular matrix selected from the group consisting of poly-D-lysine, laminin, poly-L-lysine, matrigel, agar, polyornithine, gelatin, collagen, fibronectin and vitronectin.

26. The method of claim 6, wherein the medium of (1) further comprises DMEM/F12, 10% KnockOut serum replacement, and 1% B27 supplement; and the medium of (2) further comprises DMEM/F12, about 1% B27 supplement, and about 1% N2 supplement.

27. The method of claim 1, wherein the first medium further comprises DMEM/F12, about 1% B27 supplement, and about 1% N2 supplement.

28. The method of claim 1, wherein the immature retinal ganglion cells express:
one or more genes selected from the group consisting of Brn3B, Brn3A, Islet-1, NF200 and Tuj1; and
Math5.

29. The method of claim 1, wherein the mature retinal ganglion cells are present at from about 60% to about 95% or more of total cells after the culturing of (b)(i) or (b)(ii).

30. The method of claim 6, wherein the BMP signaling pathway inhibitor is one or more selected from the group consisting of Noggin, chordin, twisted gastrulation (Tsg), cerberus, coco, gremlin, PRDC (protein related to DAN and Cerberus), DAN (differential screening-selected gene aberrative in neuroblastoma), dante, follistatin, USAG-1(uterine sensitization-associated gene 1), dorsomorphin and sclerostin.

31. The method of claim 6, wherein a concentration of the BMP signaling pathway inhibitor in the medium of (1) is 0.01ng/mL to 100ng/mL.

32. The method of claim 6, wherein the FGF signaling pathway activator is one or more selected from the group consisting of FGF1,FGF2, FGF4, FGF8, FGF9, FGF17 and FGF19.

33. The method of claim 6, wherein a concentration of the FGF signaling pathway activator in the medium of (2) is 0.01ng/mL to 100ng/mL.

* * * * *